(12) United States Patent
Alcaraz et al.

(10) Patent No.: US 9,573,955 B2
(45) Date of Patent: *Feb. 21, 2017

(54) COMPOUNDS

(71) Applicant: CHIESI FARMACEUTICI S.p.A., Parma (IT)

(72) Inventors: Lilian Alcaraz, Harlow (GB); Jonathan Mark Sutton, Harlow (GB); Elisabetta Armani, Parma (IT); Carmelida Capaldi, Parma (IT)

(73) Assignee: Chiese Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/571,755

(22) Filed: Dec. 16, 2014

(65) Prior Publication Data

US 2015/0166548 A1 Jun. 18, 2015

(30) Foreign Application Priority Data

Dec. 16, 2013 (EP) ..................................... 13197370
Jun. 12, 2014 (EP) ..................................... 14172174

(51) Int. Cl.
*C07D 487/04* (2006.01)

(52) U.S. Cl.
CPC .................. *C07D 487/04* (2013.01)

(58) Field of Classification Search
CPC .................................................. C07D 487/04
See application file for complete search history.

(56) References Cited

U.S. PATENT DOCUMENTS

| 6,187,797 | B1 * | 2/2001 | Pruitt | ............... | C07D 261/18 |
| | | | | | 514/340 |
| 8,198,288 | B2 | 6/2012 | Ray et al. | | |
| 8,691,826 | B2 | 4/2014 | Blench et al. | | |
| 8,957,082 | B2 | 2/2015 | Ray et al. | | |
| 2013/0123278 | A1 | 5/2013 | Edwards et al. | | |
| 2013/0150380 | A1 | 6/2013 | Edwards et al. | | |
| 2014/0018345 | A1 | 1/2014 | Capaldi et al. | | |
| 2014/0171414 | A1 * | 6/2014 | Alcaraz | ............... | C07D 487/04 |
| | | | | | 514/211.15 |
| 2014/0179714 | A1 | 6/2014 | Blench et al. | | |

FOREIGN PATENT DOCUMENTS

| DE | 10 2006 031314 | 1/2008 |
| WO | 2011/0110858 | 9/2011 |
| WO | 2011/0110859 | 9/2011 |
| WO | 2013/0037809 | 3/2013 |

OTHER PUBLICATIONS

Gaikwad et al.; "The Use of Bioisosterism in Drug Design and Molecular Modification"; 2012; Am. J. Pharm. Tech. Res.; 2(4); ISSN: 2249-3387; pp. 1-23.*
DeBernardis et al.; "Evaluation of the Side Arm of (Naphthylvinyl) pyridinium Inhibitors of Choline Acetyltransferase"; 1988; J. Med. Chem; 31: 117-121.*
Stockley et al.; "Phase II study of a neutrophil elastase inhibitor (AZD9668) in patients with bronchiectasis"; 2013; Respiratory Medicine; 107, 524-533.*
Extended European Search Report in Application No. 13197370.3 issued Feb. 20, 2014.
U.S. Appl. No. 14/731,786, filed Jun. 5, 2015, Armani, et al.

* cited by examiner

*Primary Examiner* — Timothy Thomas
(74) *Attorney, Agent, or Firm* — Oblon, McClelland, Maier & Neustadt, L.L.P.

(57) ABSTRACT

Heterocyclic compounds and salts according to formula (I), which are pyrimidinone derivatives, described herein exhibit human neutrophil elastase inhibitory properties, and useful for treating diseases or conditions in which HNE is implicated.

14 Claims, No Drawings

COMPOUNDS

CROSS REFERENCES TO RELATED APPLICATIONS

This application claims priority to European Patent Applications No. 13197370.3 filed on Dec. 16, 2013 and European Patent Applications No. 14172174.6 filed on Jun. 12, 2014, both of which are incorporated herein by reference in their entireties.

BACKGROUND OF THE INVENTION

Field of the Invention

The present invention relates to heterocyclic compounds, which are pyrimidinone derivatives having human neutrophil elastase inhibitory properties, and their use in therapy.

Discussion of the Background

Human neutrophil elastase (FINE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (Bieth, G. In *Regulation of Matrix accumulation,* Mecham, R. P. (Eds), Academic Press, NY, USA 1986, 217-306). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (Wright, J. L. et al. *Am. J. Respir. Crit. Care Med.* 2002, 166, 954-960; and Churg, A. et al. *Am. J. Respir. Crit. Care Med.* 2003, 168, 199-207). Thus, FINE can play a role both in matrix destruction and in amplifying inflammatory responses in chronic respiratory diseases where neutrophil influx is a characteristic feature. Indeed, FINE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodelling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three can be due to neutrophil-mediated inflammation, as supported by the increased number of neutrophils observed in bronchoalveolar leakage (BAL) fluids of COPD patients (Thompson, A. B.; Daughton, D.; et al. *Am. Rev. Respir. Dis.* 1989, 140, 1527-1537). The major pathogenic determinant in COPD has long been considered to be the protease-anti-protease balance (also known as the "elastase:anti-elastase hypothesis"), in which an imbalance of HNE and endogenous antiproteases such as a1-antitrypsin ($\alpha_1$-AT), secretory leukocyte protease inhibitor (SLPI) and pre-elafin leads to the various inflammatory disorders of COPD. Individuals that have a genetic deficiency of the protease inhibitor α1-antitrypsin develop emphysema that increases in severity over time (Laurrell, C. B.; Erikkson, S *Scand. J. Clin. Invest.* 1963 15, 132-140). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Several human neutrophil inhibitors have been disclosed so far in the art. In particular, International Patent Applications no. WO2011/110858 and no. WO2011/110859 describe some pyrimidine derivatives having human neutrophil elastase inhibitory properties and their use in therapy.

Although several HNE inhibitors have been disclosed so far as above reported, there is still a need for further HNE inhibitors. Particularly, there is still a need for further HNE inhibitors endowed with a high potency for HNE enzyme inhibition. Particularly advantageous would also be the identification of further HNE inhibitors endowed with a high potency for HNE enzyme inhibition and which would show an appropriate developability profile as an inhalation treatment.

The present invention addresses the above mentioned need by providing the compounds of the invention.

SUMMARY OF THE INVENTION

Accordingly, it is one object of the present invention to provide novel FINE inhibitors.

It is another object of the present invention to provide novel HNE inhibitors endowed with a high potency for HNE enzyme inhibition.

It is another object of the present invention to provide novel HNE inhibitors endowed with a high potency for FINE enzyme inhibition and which exhibit an appropriate developability profile as an inhalation treatment.

It is another object of the present invention to provide novel compositions which contain such a HNE inhibitor.

It is another object of the present invention to provide novel methods of treating and/or preventing certain diseases and conditions by administering such a HNE inhibitor.

These and other objects, which will become apparent during the following detailed description, have been achieved by the inventors' discovery of the compounds of formula (I) described below.

DETAILED DESCRIPTION OF THE PREFERRED EMBODIMENTS

Thus, the present provides novel compounds which are inhibitors of HNE, and are useful in the treatment of diseases or conditions in which FINE activity plays a part.

In one aspect the invention provides a compound of formula (I), or a pharmaceutically acceptable salt thereof

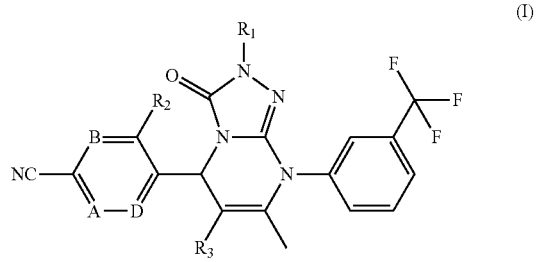

wherein

A, B and D are independently CH or N;

$R_1$ is selected from the group consisting of:
hydrogen;
$(C_1-C_6)$alkyl;
$NR_7R_8(C_1-C_6)$alkyl-;
$(C_2-C_4)$alkenyl;
phenyl$(C_1-C_6)$alkyl- wherein such phenyl ring is optionally substituted by a group $NR_{15}R_{16}(C_1-C_6)$alkyl- or by $N^+R_{15}R_{16}R_{17}(C_1-C_6)$alkyl-;
—$CH_2(CH_2)_n$OH;
—$(CH_2)_n$CONR_5R_6$;
—$(CH_2)_n$SO_2NR_5R_6$;
a group —$CH_2$—$(CH_2)_n$NR_5SO_2R_6$;
—$(CH_2)_t$—$(C_6H_4)$—$SO_2(C_1-C_4)$alkyl;
—$(CH_2)_r$SO_2(C_1-C_4)$alkyl wherein such $(C_1-C_4)$alkyl is optionally substituted by a group —$NR_{15}R_{16}$ or —$N^+R_{15}R_{16}R_{17}$;
—$SO_2$-phenyl wherein such phenyl ring is optionally substituted by $NR_7R_8(C_1-C_6)$alkyl-; and
a group —$(CH_2)_n$—W wherein W is a 5-6-membered heteroaryl ring which is optionally substituted by a group —$SO_2(C_1-C_4)$alkyl;

n is 1, 2 or 3;
t is 0, 1, 2 or 3;
r is 0, 1, 2, 3 or 4;
$R_5$ is selected in the group consisting of hydrogen, $(C_1-C_6)$alkyl, $NR_{16}R_{15}(C_1-C_6)$alkyl- and $N^+R_{17}R_{15}R_{16}(C_1-C_6)$alkyl-;
$R_6$ is hydrogen or $(C_1-C_6)$alkyl;
$R_7$ is selected in the group consisting of hydrogen, $(C_1-C_6)$alkyl, $(C_1-C_6)$alkylcarbonyl-, —$SO_2(C_1-C_4)$alkyl and $NR_{16}R_{15}(C_1-C_6)$alkyl-;
$R_8$ is hydrogen or $(C_1-C_6)$alkyl;
alternatively, $R_7$ and $R_8$ with the nitrogen atom they are linked to can form a $(C_5-C_7)$heterocycloalkyl ring system optionally substituted by one or more $(C_1-C_6)$alkyl or oxo groups;
$R_{16}$ is hydrogen or $(C_1-C_6)$alkyl;
$R_{15}$ is hydrogen or $(C_1-C_6)$alkyl;
$R_{17}$ is hydrogen or $(C_1-C_6)$alkyl;
$R_3$ is a group cyano or a group —C(O)—$XR_4$;
X is a divalent group selected from —O—, —$(CH_2)$— and —NH—;
$R_4$ is a group selected in the list consisting of
hydrogen;
$(C_1-C_6)$alkyl;
a group of formula -[Alk$^1$]-Z wherein Alk$^1$ is a $(C_1-C_4)$ alkylene radical and Z is:
(i) —$NR_9R_{10}$ wherein $R_9$ and $R_{10}$ are independently hydrogen, $(C_1-C_6)$alkyl or $(C_3-C_6)$cycloalkyl, wherein $(C_1-C_6)$alkyl or $(C_3-C_6)$cycloalkyl groups are optionally substituted by one to four groups $R_{35}$ independently selected in the group consisting of $(C_1-C_6)$alkyl, $(C_1-C_6)$alkoxyl, hydroxyl, hydroxyl-$(C_1-C_6)$alkyl, halo, trifluoromethyl, trifluoromethoxy; or, $R_9$ and $R_{10}$ taken together with the nitrogen they are linked to, form a monocyclic $(C_5-C_7)$ heterocyclic ring which can contain a further heteroatom selected from N, O and S and which is optionally substituted by one to four groups $R_{35}$ independently selected in the group consisting of: $(C_1-C_6)$alkyl, $(C_1-C_6)$alkoxyl, hydroxyl, hydroxyl-$(C_1-C_6)$alkyl, halo, trifluoromethyl, trifluoromethoxy; or
(ii) —$N^+R_{11}R_{12}R_{13}$ wherein $R_{11}$, $R_{12}$ and $R_{13}$ are each independently $(C_1-C_6)$alkyl or $(C_3-C_6)$cycloalkyl, wherein such $(C_1-C_6)$alkyl or $(C_3-C_6)$cycloalkyl groups are optionally substituted by one to four groups $R_{36}$ independently selected in the group consisting of $(C_1-C_6)$alkyl, $(C_1-C_6)$alkoxyl, hydroxyl, hydroxyl-$(C_1-C_6)$alkyl, halo, trifluoromethyl and trifluoromethoxy; or any two of $R_{11}$, $R_{12}$ and $R_{13}$, taken together with the nitrogen they are linked to, form a monocyclic $(C_5-C_7)$heterocyclic ring which can contain a further heteroatom selected from N, O and S and the other of $R_{11}$, $R_{12}$ and $R_{13}$ is a $(C_1-C_6)$alkyl or an optionally substituted $(C_3-C_6)$cycloalkyl, wherein such monocyclic $(C_5-C_7)$heterocyclic, $(C_1-C_6)$alkyl or $(C_3-C_6)$cycloalkyl groups are optionally substituted by one to four groups $R_{36}$ independently selected in the group consisting of $(C_1-C_6)$alkyl, $(C_1-C_6)$alkoxyl, hydroxyl, hydroxyl-$(C_1-C_6)$alkyl, halo, trifluoromethyl and trifluoromethoxy;

a radical of formula —$(CH_2)_q$-[Q]-$(CH_2)_p$ Z wherein Z is as above defined, q is 0 or an integer from 1 to 3, p is 0 or an integer from 1 to 3 and Q is a divalent group selected from —O—, phenylene, $(C_5-C_7)$heterocycloalkylene, $(C_3-C_6)$cycloalkyl and pyridinylene, wherein such phenylene, $(C_5-C_7)$heterocycloalkylene, $(C_3-C_6)$cycloalkyl and pyridinylene are optionally substituted by one to four groups $R_{37}$ independently selected in the group consisting of $(C_1-C_6)$alkyl, $(C_1-C_6)$alkoxyl, hydroxyl, hydroxyl-$(C_1-C_6)$alkyl, halo, trifluoromethyl and trifluoromethoxy;

$R_2$ is selected from the group consisting of

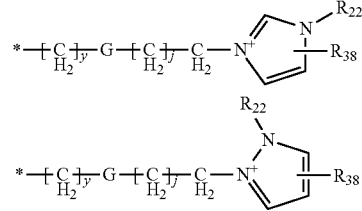

[OR ISOMERS THEROF]

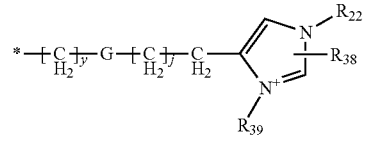

[OR ISOMERS THEROF]

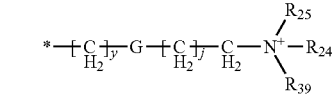

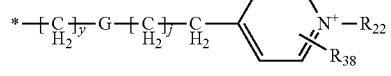

[OR C-LINKED ISOMERS THEROF]

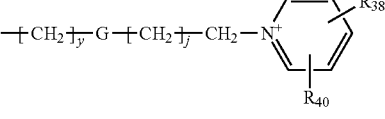

[OR C-LINKED ISOMERS THEROF]

-continued

*—(CH₂)ᵧ—G—(CH₂)ⱼ—N⁺
[pyrrolo ring with R₂₄]

[OR C-LINKED ISOMERS THEROF]

j is 0 or an integer from 1 to 4; y is 0 or an integer from 1 to 4;

G is a divalent linker selected from the group consisting of —O—, —(SO₂)—, NR₂₅, a bond, $C_2$-$C_6$-alkenylene, $C_2$-$C_6$-alkynylene, ($C_3$-$C_6$)cycloalkylene, mono or bicyclic heterocycloalkylene, —[CONR₂₅]— and —[NR₂₅CO]—;

$R_{24}$ is hydrogen or ($C_1$-$C_6$)alkyl which is optionally substituted by one or more groups selected from —OR₃₁, —SO₂R₃₁, —CO₂R₃₁, —CONR₃₁R₃₂ and —SO₂NR₃₁R₃₂;

$R_{25}$ is hydrogen or ($C_1$-$C_6$)alkyl;

$R_{22}$ is selected in the group consisting of ($C_1$-$C_6$)alkyl which is optionally substituted by one or more groups ($C_3$-$C_6$) cycloalkyl, phenyl, benzyl, CN, —OR₂₆, —SO₂R₂₆, —CO₂R₂₆, —CONR₂₆R₂₇ or —SO₂NR₂₆R₂₇; ($C_3$-$C_{10}$)cycloalkyl optionally substituted by one or more groups —OR₂₆, —SO₂R₂₆, —CO₂R₂₆, —CONR₂₆R₂₇ or —SO₂NR₂₆R₂₇; ($C_4$-$C_7$)heterocycloalkyl which is optionally substituted by one or more groups —OR₂₆, —SO₂R₂₆, —CO₂R₂₆, —CONR₂₆R₂₇ or —SO₂NR₂₆R₂₇; aryl optionally substituted with —OH; and heteroaryl optionally substituted with —OH;

$R_{26}$ and $R_{27}$ are independently hydrogen or ($C_1$-$C_6$)alkyl; alternatively, $R_{22}$ and $R_{38}$ with the nitrogen atom they are linked to can form a 5-11-membered saturated monocyclic or bicyclic heterocyclic or heteroaromatic ring system which is optionally substituted by one or more groups ($C_1$-$C_6$) alkyl, ($C_1$-$C_6$)alkoxyl, hydroxyl, hydroxyl-($C_1$-$C_6$)alkyl, —OR₂₈, halo, —SO₂R₃₃, —CO₂R₃₃, —CONR₃₃R₃₄, —SO₂NR₃₃R₃₄, nitro, amino, acetamido, trifluoromethyl and trifluoromethoxy;

$R_{28}$, $R_{29}$, $R_{30}$, $R_{31}$, $R_{32}$, $R_{33}$ and $R_{34}$ are independently hydrogen or ($C_1$-$C_6$)alkyl;

$R_{38}$ is —H or one or two substituents selected in the list consisting of ($C_1$-$C_6$)alkyl, ($C_1$-$C_6$)alkoxyl, hydroxyl, hydroxyl-($C_1$-$C_6$)alkyl, halo, trifluoromethyl and trifluoromethoxy; alternatively $R_{38}$ and $R_{40}$, when they are —($C_1$-$C_6$)alkyl, are linked to form a 6-membered aryl ring;

$R_{39}$ is —($C_1$-$C_6$)alkyl-heteroaryl, wherein the heteroaryl portion is optionally substituted with one or more substituents selected from —CN, —C(=O), ($C_1$-$C_6$)alkyl, ($C_1$-$C_6$) alkoxyl, hydroxyl, hydroxyl-($C_1$-$C_6$)alkyl, —OR₂₈, halo, —SO₂R₃₃, —CO₂R₃₃, —CONR₃₃R₃₄, —SO₂NR₃₃R₃₄, nitro, amino, acetamido, trifluoromethyl and trifluoromethoxy;

$R_{40}$ is selected from the group consisting of —CN, —($C_1$-$C_6$)alkyl, —SO₂($C_1$-$C_6$)alkyl and —SO₂NR₂₄R₂₅ wherein only two of A, B and D can be at the same time a nitrogen atom;

wherein if one or more groups N⁺R₁₁R₁₂R₁₃— or N⁺R₁₅R₁₆R₁₇— are present, they form quaternary salts with a pharmaceutically acceptable counter ion;

wherein groups $R_5$ to $R_{38}$, and n can have the same or different meanings, if present in more than one group and with the proviso that when $R_{40}$ is —($C_1$-$C_6$)alkyl, then the two $R_{38}$ substituents are both —($C_1$-$C_6$)alkyl.

Compounds of formula (I) can be prepared in the form of salts, particularly pharmaceutically acceptable salts, N-oxides, hydrates, solvates and polymorphs thereof. Any reference to a compound herein, or reference to "compounds of the present invention", "compounds of formula (I)", and the like includes such compounds whether or not in salt, N-oxide, hydrate, solvate or polymorphic form.

Compounds of the present invention can be used in the treatment or prevention of diseases in which HNE is implicated, for example chronic obstructive pulmonary disease (COPD), bronchiectasis, chronic bronchitis, lung fibrosis, pneumonia, acute respiratory distress syndrome (ARDS), pulmonary emphysema, smoking-induced emphysema and cystic fibrosis.

Hence other aspects of the invention are (i) a pharmaceutical composition comprising a compound of the invention and a pharmaceutically acceptable carrier or excipient; and (ii) the use of a compound of the invention for the manufacture of a medicament for the treatment or prevention of a disease or condition in which HNE is implicated.

In one embodiment, the invention provides a compound of formula (TB), or a pharmaceutically acceptable salt thereof (IB)

[chemical structure]

wherein

A is CH or N;

B is CH or N;

D is CH or N;

$R_1$ is selected from the group consisting of
  hydrogen;
  ($C_1$-$C_6$)alkyl;
  NR₇R₈($C_1$-$C_6$)alkyl;
  ($C_2$-$C_4$)alkenyl;
  phenyl($C_1$-$C_6$)alkyl- wherein such phenyl ring is optionally substituted by a group NR₁₅R₁₆($C_1$-$C_6$)alkyl- or by N⁺R₁₅R₁₆R₁₇($C_1$-$C_6$)alkyl-;
  —CH₂(CH₂)ₙOH;
  —(CH₂)ₙCONR₅R₆;
  —(CH₂)ₙSO₂NR₅R₆;
  —CH₂—(CH₂)ₙNR₅SO₂R₆;
  —(CH₂)ₜ—($C_6H_4$)—SO₂($C_1$-$C_4$)alkyl;
  —(CH₂)ₙSO₂($C_1$-$C_4$)alkyl wherein such ($C_1$-$C_4$)alkyl is optionally substituted by a group —NR₁₅R₁₆ or —N⁺R₁₅R₁₆R₁₇;
  —SO₂-phenyl wherein such phenyl ring is optionally substituted by NR₇R₈($C_1$-$C_6$)alkyl; and
  —(CH₂)ₙ—W wherein W is a 5-6-membered heteroaryl ring which is optionally substituted by a group —SO₂($C_1$-$C_4$)alkyl;

n is 1, 2 or 3;

t is 0, 1, 2 or 3;

r is 0, 1, 2, 3 or 4;

$R_5$ is selected in the group consisting of hydrogen, ($C_1$-$C_6$) alkyl, NR₁₆R₁₅($C_1$-$C_6$)alkyl and N⁺R₁₇R₁₅R₁₆($C_1$-$C_6$)alkyl;

$R_6$ is hydrogen or ($C_1$-$C_6$)alkyl;

$R_7$ is selected in the group consisting of hydrogen, ($C_1$-$C_6$) alkyl, ($C_1$-$C_6$)alkylcarbonyl, —

$SO_2(C_1-C_4)$alkyl and $NR_{16}R_{15}(C_1-C_6)$alkyl;
$R_8$ is hydrogen or $(C_1-C_6)$alkyl;
alternatively, $R_7$ and $R_8$ with the nitrogen atom they are linked to can form a $(C_5-C_7)$heterocycloalkyl ring system which is optionally substituted by one or more groups $(C_1-C_6)$alkyl and oxo;
$R_{15}$, $R_{16}$ and $R_{17}$ are independently hydrogen or $(C_1-C_6)$alkyl;
$R_3$ is cyano or —C(O)—$XR_4$;
X is a divalent group selected from —O—, —(CH$_2$)— and —NH—;
$R_4$ is a group selected from the group consisting of
  hydrogen;
  —$(C_1-C_6)$alkyl;
  a group of formula -[Alk$^1$]-Z wherein Alk$^1$ represents a $(C_1-C_4)$alkylene radical and Z is:
(i) —$NR_9R_{10}$ wherein $R_9$ and $R_{10}$ are independently hydrogen, $(C_1-C_6)$alkyl or $(C_3-C_6)$cycloalkyl group, wherein such $(C_1-C_6)$alkyl or $(C_3-C_6)$cycloalkyl group are optionally substituted by one to four group $R_{35}$ independently selected in the group consisting of: $(C_1-C_6)$alkyl, $(C_1-C_6)$alkoxyl, hydroxyl, hydroxyl-$(C_1-C_6)$alkyl, halo, trifluoromethyl, trifluoromethoxy; or, taken together with the nitrogen they are linked to, form a monocyclic $(C_5-C_7)$heterocyclic ring which can contain a further heteroatom selected from N, O and S and which is optionally substituted by one to four group $R_{35}$ independently selected in the group consisting of: $(C_1-C_6)$alkyl, $(C_1-C_6)$alkoxyl, hydroxyl, hydroxyl-$(C_1-C_6)$alkyl, halo, trifluoromethyl, trifluoromethoxy;
or
(ii) —$N^+R_{11}R_{12}R_{13}$ wherein $R_{11}$, $R_{12}$ and $R_{13}$ are each independently $(C_1-C_6)$alkyl or $(C_3-C_6)$cycloalkyl group, wherein such $(C_1-C_6)$alkyl or $(C_3-C_6)$cycloalkyl group are optionally substituted by one to four group $R_{36}$ independently selected in the group consisting of: $(C_1-C_6)$alkyl, $(C_1-C_6)$alkoxyl, hydroxyl, hydroxyl-$(C_1-C_6)$alkyl, halo, trifluoromethyl, trifluoromethoxy; or any two of $R_{11}$, $R_{12}$ and $R_{13}$ taken together with the nitrogen they are linked to form a monocyclic $(C_5-C_7)$heterocyclic ring which can contain a further heteroatom selected from N, O and S and the other of $R_{11}$, $R_{12}$ and $R_{13}$ is a $(C_1-C_6)$alkyl or an optionally substituted $(C_3-C_6)$cycloalkyl group, wherein such monocyclic $(C_5-C_7)$heterocyclic, $(C_1-C_6)$alkyl or $(C_3-C_6)$cycloalkyl group are optionally substituted by one to four group $R_{36}$ independently selected in the group consisting of: $(C_1-C_6)$alkyl, $(C_1-C_6)$alkoxyl, hydroxyl, hydroxyl-$(C_1-C_6)$alkyl, halo, trifluoromethyl, trifluoromethoxy;
  a radical of formula —(CH$_2$)$_q$-[Q]-(CH$_2$)$_p$ Z wherein Z is as above defined, q is 0 or an integer from 1 to 3, p is 0 or an integer from 1 to 3 and Q is a divalent group selected from —O—, phenylene, $(C_5-C_7)$heterocycloalkylene, $(C_3-C_6)$cycloalkyl and pyridinylene, wherein such phenylene, $(C_5-C_7)$heterocycloalkylene, $(C_3-C_6)$cycloalkyl and pyridinylene are optionally substituted by one to four groups $R_{37}$ independently selected in the group consisting of $(C_1-C_6)$alkyl, $(C_1-C_6)$alkoxyl, hydroxyl, hydroxyl-$(C_1-C_6)$alkyl, halo, trifluoromethyl and trifluoromethoxy;
$R_2$ is selected from the group consisting of:

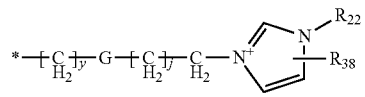

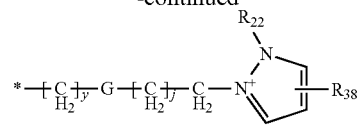

[OR ISOMERS THEROF]

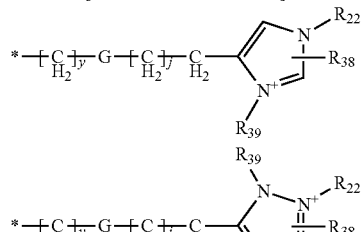

[OR ISOMERS THEROF]

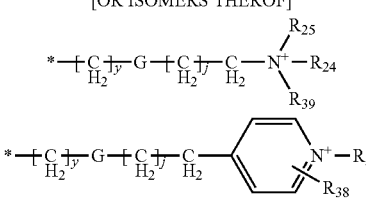

[OR C-LINKED ISOMERS THEROF]

j is 0 or an integer from 1 to 4;
y is 0 or an integer from 1 to 4;
G is a divalent linker selected from the group consisting of —O—, —(SO$_2$)—, $NR_{25}$, a bond, $C_2-C_6$-alkenylene, $C_2-C_6$-alkynylene, $(C_3-C_6)$cycloalkylene, mono or bicyclic heterocycloalkylene, —[CONR$_{25}$]— and —[NR$_{25}$CO]—;
$R_{24}$ is hydrogen or $(C_1-C_6)$alkyl, which $(C_1-C_6)$alkyl is optionally substituted by one or more groups —$OR_{31}$, —$SO_2R_{31}$, —$CO_2R_{31}$, —$CONR_{31}R_{32}$ or —$SO_2NR_{31}R_{32}$;
$R_{25}$ is hydrogen or $(C_1-C_6)$alkyl;
$R_{22}$ is selected in the group consisting of: $(C_1-C_6)$alkyl, which $(C_1-C_6)$alkyl is optionally substituted by one or more groups $(C_3-C_6)$cycloalkyl, phenyl, benzyl, CN, —$OR_{26}$, —$SO_2R_{26}$, —$CO_2R_{26}$, —$CONR_{26}R_{27}$ or —$SO_2NR_{26}R_{27}$; $(C_3-C_{10})$cycloalkyl which is optionally substituted by one or more groups —$OR_{26}$, —$SO_2R_{26}$, —$CO_2R_{26}$, —$CONR_{26}R_{27}$ or —$SO_2NR_{26}R_{27}$; and $(C_4-C_7)$heterocycloalkyl which is optionally substituted by one or more groups —$OR_{26}$, —$SO_2R_{26}$, —$CO_2R_{26}$, —$CONR_{26}R_{27}$ or —$SO_2NR_{26}R_{27}$;
$R_{26}$ is hydrogen or $(C_1-C_6)$alkyl;
$R_{27}$ is hydrogen or $(C_1-C_6)$alkyl;
Alternatively, $R_{22}$ and $R_{38}$ with the nitrogen atom they are linked to can form a 5-11-membered saturated monocyclic or bicyclic heterocyclic or heteroaromatic ring system which is optionally substituted by one or more groups $(C_1-C_6)$alkyl, $(C_1-C_6)$alkoxyl, hydroxyl, hydroxyl-$(C_1-C_6)$alkyl, —$OR_{28}$, halo, —$SO_2R_{33}$, —$CO_2R_{33}$, —$CONR_{33}R_{34}$, —$SO_2NR_{33}R_{34}$, nitro, amino, acetamido, trifluoromethyl and trifluoromethoxy;
$R_{28}$ is hydrogen or $(C_1-C_6)$alkyl;
$R_{29}$ is hydrogen or $(C_1-C_6)$alkyl;
$R_{30}$ is hydrogen or $(C_1-C_6)$alkyl;
$R_{31}$ is hydrogen or $(C_1-C_6)$alkyl;
$R_{32}$ is hydrogen or $(C_1-C_6)$alkyl;
$R_{33}$ is hydrogen or $(C_1-C_6)$alkyl;
$R_{34}$ is hydrogen or $(C_1-C_6)$alkyl;
$R_{38}$ represents one or two optional substituents selected in the list consisting of $(C_1-C_6)$alkyl, $(C_1-C_6)$alkoxyl, hydroxyl, hydroxyl-$(C_1-C_6)$alkyl, halo, trifluoromethyl, trifluoromethoxy;

$R_{39}$ is —$(C_1-C_6)$alkyl-heteroaryl, wherein the heteroaryl portion is optionally substituted by one or more substituents selected from $(C_1-C_6)$alkyl, $(C_1-C_6)$alkoxyl, hydroxyl, hydroxyl-$(C_1-C_6)$alkyl, —$OR_{28}$, halo, —$SO_2R_{33}$, —$CO_2R_{33}$, —$CONR_{33}R_{34}$, —$SO_2NR_{33}R_{34}$, nitro, amino, acetamido, trifluoromethyl and trifluoromethoxy;

alternatively, $R_{39}$ is selected in the group consisting of: —$(C_1-C_6)$alkyl-bicyclic-heteroaryl, where bicyclic-heteroaryl groups can consist of, but not exhaustively: quinolones, isoquinolines, indole, isoindole, indolizine, benzimidazole, azabenzimidazole, benzoxazole and benzothiazole. The bicyclic-heteroaryl groups can be further substituted with optional substituents selected in the list consisting of $(C_1-C_6)$alkyl, $(C_1-C_6)$alkoxyl, hydroxyl, hydroxyl-$(C_1-C_6)$alkyl, —$OR_{28}$, halo, —$SO_2R_{33}$, —$CO_2R_{33}$, —$CONR_{33}R_{34}$, —$SO_2NR_{33}R_{34}$, nitro, amino, acetamido, trifluoromethyl and trifluoromethoxy;

wherein only two of A, B and D can be at the same time a nitrogen atom;

wherein if one or more groups $N^+R_{11}R_{12}R_{13}$— or $N^+R_{15}R_{16}R_{17}$— are present, they form quaternary salts with a pharmaceutically acceptable counter ion;

and wherein groups $R_5$ to $R_{38}$, and n can have the same or different meanings, if present in more than one group.

The term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl, and n-hexyl.

The term "$(C_d-C_b)$alkenyl" wherein a and b are integers refers to a straight or branched chain alkenyl moiety having from d to b carbon atoms having at least one double bond of either E or Z stereochemistry where applicable. Thus when d is 2 and b is 6, for example, the term includes, for example, vinyl, allyl, 1- and 2-butenyl and 2-methyl-2-propenyl.

By analogy, the expression "$(C_d-C_b)$alkenylene" refers to a divalent "$(C_d-C_b)$alkenyl" radical as above defined.

The term "$(C_d-C_b)$alkynyl" refers to straight or branched carbon chains with one or more triple bonds wherein the number atoms is in the range 2 to 6.

By analogy, the expression "$(C_d-C_b)$alkynylene" refers to a divalent "$(C_d-C_b)$alkynyl" radical as above defined.

The expressions "$NR_{15}R_{16}(C_a-C_b)$alkyl", "$NR_{24}R_{39}(C_a-C_b)$alkyl" or "$NR_7R_8(C_d-C_b)$alkyl", wherein a and b are as above defined, refer to the above defined "$(C_d-C_b)$alkyl" groups wherein one hydrogen atom is replaced by a group —$NR_{15}R_{16}$, —$NR_{24}R_{39}$ or —$NR_7R_8$ respectively.

The expressions "$N^+R_{15}R_{16}R_{17}(C_a-C_b)$alkyl" or "$N^+R_{11}R_{12}R_{13}(C_a-C_b)$alkyl" wherein a and b are as above defined, refer to the above defined "$(C_a-C_b)$alkyl" groups wherein one hydrogen atom is replaced by a group —$N^+R_{15}R_{16}R_{17}$ or $N^+R_{11}R_{12}R_{13}$ respectively.

The expressions "mono$(C_a-C_b)$alkyl" or "di$(C_a-C_b)$alkyl amino", wherein a and b are integers, refer to an amino group wherein, respectively, one or both hydrogen atoms are replaced by a group $(C_a-C_b)$alkyl.

The expression "phenyl$(C_a-C_b)$alkyl" refers to the above defined "$(C_a-C_b)$alkyl" radicals wherein one hydrogen atom is replaced by one a phenyl group.

The term "divalent $(C_a-C_b)$alkylene radical" wherein a and b are integers refers to a saturated hydrocarbon chain having from a to b carbon atoms as above defined and two unsatisfied valences.

The term "$(C_a-C_b)$cycloalkyl", wherein a and b are integers, refers to saturated monocyclic, bicyclic or tricyclic hydrocarbon groups containing from a to b ring carbon atoms, as appropriate. Examples include cyclopropyl, cyclobutyl, cyclopentyl, cyclohexyl and cycloheptyl, adamantyl.

As used herein, the unqualified term "heterocyclyl" or "heterocyclic" and relates to a saturated mono-, bi- or tri-cyclic non-aromatic radical containing one or more heteroatoms selected from S, N and O. In the case of bicyclic heterocyclic systems, included within the scope of the term are fused, Spiro and bridged bicyclic systems, such as for example a quinuclidine ring. In particular, the term "$C_a-C_b$heterocycloalkyl" refers to monocyclic $(C_a-C_b)$cycloalkyl groups, in which at least one ring carbon atom is replaced by a heteroatom (e.g. N, NH, S or O). Examples of $(C_a-C_b)$ heterocycloalkyl include pyrrolidinyl, thiazolidinyl, piperazinyl, piperidinyl, morpholinyl, thiomorpholinyl.

By analogy, the expression "heterocycloalkylene" refers to a divalent heterocyclic radical as above defined. In particular, the expression "$(C_a-C_b)$heterocycloalkylene" refers to a divalent $(C_a-C_b)$heterocycloalkyl radical (such as for example pyrrolidinene) wherein "$(C_a-C_b)$heterocycloalkyl group is as above defined.

The expression "heteroaryl" refers to mono or bi-cyclic ring systems with 5 to 11 ring atoms, in which at least one ring is aromatic and in which at least one ring atom is a heteroatom (e.g. N, NH, S or O).

Examples of suitable 5,6-membered heteroaryl monocyclic systems include, for instance thiophene, pyrrole, pyrazole, imidazole, isoxazole, oxazole, isothiazole, thiazole, pyridine, pyrimidine, pyridazine and furan radicals and the like.

Examples of suitable bi-cyclic heteroaryl ring systems include quinolones, isoquinolines, indole, isoindole, indolizine, benzimidazole, azabenzimidazole, benzoxazole and benzothiazole radicals and the like.

The term "$(C_a-C_b)$alkoxyl" wherein a and b are integers, refers to straight-chained and branched alkoxy groups wherein the number of constituent carbon atoms is in the range from a to b. Particular alkyl groups are methoxyl, ethoxyl, n-propoxyl, isopropoxyl and t-butoxyl.

The symbol "—$C_6H_4$—" indicates a divalent phenylene ring radical.

The expression "$(C_a-C_b)$alkylcarbonyl" refers to —CO $(C_a-C_b)$alkyl groups wherein the group "$(C_a-C_b)$alkyl" has the meaning above defined.

The expressions "$(C_a-C_b)$alkylhydroxyl" refer to the above defined "$(C_a-C_b)$alkyl" radicals wherein one hydrogen atom is replaced by a group —OH.

Unless otherwise specified, the term "substituted" as applied to any moiety herein means substituted with up to four compatible substituents, each of which independently can be, for example, $(C_1-C_6)$alkyl, $(C_1-C_6)$alkoxyl, hydroxyl, hydroxyl-$(C_1-C_6)$alkyl, halo (including fluoro, bromo and chloro), trifluoromethyl, trifluoromethoxy. An "optional substituent" can be one of the foregoing substituent groups.

The term "salt" includes base addition and acid addition salts.

The term "Pharmaceutically acceptable salts" refers to derivatives of compounds of formula (I) wherein the parent compound is suitably modified by converting any of the free acid or basic group, if present, into the corresponding addition salt with any base or acid conventionally intended as being pharmaceutically acceptable.

Compounds of the present invention which are acidic can form salts, including pharmaceutically acceptable salts, with bases such as alkali metal hydroxides, e.g. sodium and potassium hydroxides; alkaline earth metal hydroxides e.g.

calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds which have quaternary nitrogen can also form quaternary salts with a pharmaceutically acceptable counter-ion such as chloride, bromide, acetate, formate, phenylsulfonate, p-toluenesulfonate, succinate, hemi-succinate, naphthalene-bis sulfonate, methanesulfonate, xinafoate, isoethionate and the like.

Where the compounds of the invention have at least one stereogenic center, they can exist as enantiomers. When the compounds according to the invention possess two or more stereogenic centers, they can additionally exist as diastereoisomers. It is to be understood that all such isomers and mixtures thereof in any proportion are encompassed within the scope of the present invention.

It will be apparent that compounds of general formula (I) at least contain one stereogenic center, namely represented by the carbon atom (1) with an asterisk below, and therefore exist as optical stereoisomers.

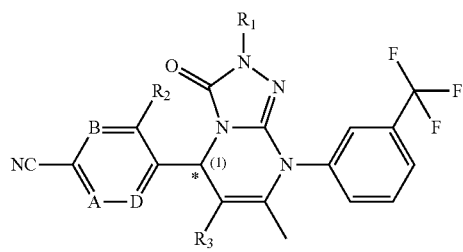

In one embodiment, the present invention is directed to compounds of formula (I)', which are compounds of formula (I) as above defined where the absolute configuration of carbon (1) is that shown here below:

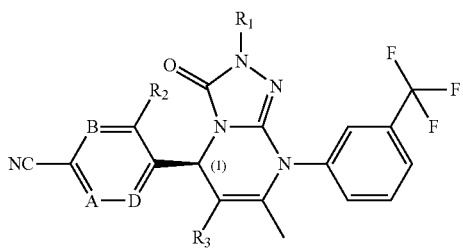

In another embodiment, the present invention is directed to compounds of formula (I)", which are compounds of formula (I) as above defined where the absolute configuration of carbon (1) is that shown herebelow:

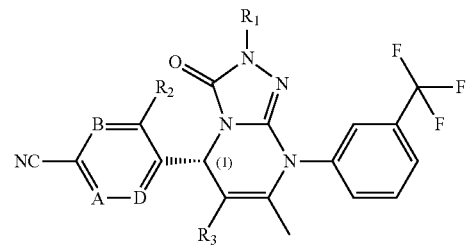

The absolute configuration for carbon (1) is assigned on the basis of Cahn-Ingold-Prelog nomenclature based on groups' priorities.

It is to be understood that all preferred groups or embodiments described here below for compounds of formula (I) can be combined among each other and apply as well to compounds of formula (I)', (I)", (IA) and (IB), mutatis mutandis.

In one embodiment, for compounds of formula (I) A is CH, B is CH and D is CH.

In another embodiment, for compounds of formula (I) A is N, B is CH and D is CH.

In a still another embodiment, for compounds of formula (I) A is CH, B is CH and D is N.

In a further another embodiment, for compounds of formula (I) A is CH, B is N and D is CH.

In a still further embodiment, for compounds of formula (I) A is N, B is N and D is CH.

In an additional embodiment, for compounds of formula (I) A is N, B is CH and D is N.

In one embodiment, for compounds of formula (I) when G is —(SO$_2$)—, y is 1.

In one embodiment, R$_2$ is a group

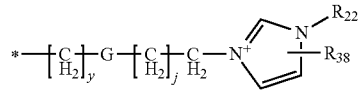

In another embodiment, R$_2$ is a group —[CH$_2$]$_y$-G-[CH$_2$]$_j$—CH$_2$—N$^+$R$_{24}$R$_{25}$R$_{39}$.

In one embodiment, R$_3$ is a group cyano or a group —C(O)—XR$_4$. In another embodiment, R$_3$ is a group —C(O)—XR$_4$.

In one embodiment, R$_4$ is optionally substituted (C$_1$-C$_6$) alkyl. In another embodiment, R$_4$ is (C$_1$-C$_6$)alkyl.

In one embodiment, X is a divalent group —O— or —NH—. In another embodiment, X is a divalent —O—.

In one embodiment, for compounds of formula (I), R$_1$ is hydrogen or a group —(CH$_2$)$_r$SO$_2$(C$_1$-C$_4$)alkyl. In another embodiment, R$_1$ is hydrogen.

In one embodiment, for compounds of formula (I), R$_2$ is a group

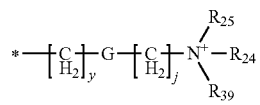

wherein R$_{39}$ is —(C$_1$-C$_6$)alkyl-heteroaryl.

In one embodiment, a compound of formula (IA) is provided

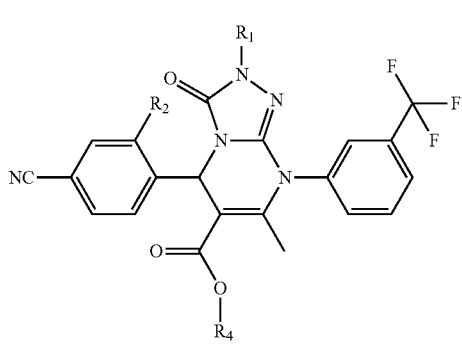

(IA)

wherein X is —O— and the other groups R$_4$, R$_2$ and R$_1$ are as above defined. In one embodiment, for compounds of formula (IA) R$_1$ is hydrogen.

In another embodiment, a compound of the invention is selected in the group consisting of:

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-methyl-3H-imidazol-1-ium formate;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-ethyl-3H-imidazol-1-ium formate;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]phenyl}-ethyl)-3-(2-hydroxy-ethyl)-3H-imidazol-1-ium formate;

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-thiazol-4-ylmethyl-ammonium formate;

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(1-methyl-1H-imidazol-4-ylmethyl)-ammonium formate;

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-pyridin-2-ylmethyl-ammonium formate;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-pyridin-2-ylmethyl-ammonium bromide;

4-Cyano-1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridinium bromide;

(2-{5-Cyano-2-[(R)-6-methoxycarbonyl-7-methyl-3-oxo-8-(3-trifluoromethyl-phenyl)-2,3,5,8-tetrahydro[1,2,4]triazolo[4,3a]pyrimidin-5-yl]-phenyl}-ethyl)dimethyl-pyridin-3-ylmethyl-ammonium bromide;

(2-{5-Cyano-2-[(R)-6-methoxycarbonyl-7-methyl-3-oxo-8-(3-trifluoromethyl-phenyl)-2,3,5,8-tetrahydro[1,2,4]triazolo[4,3a]pyrimidin-5-yl]-phenyl}-ethyl)dimethyl-(5-methyl-[1,3,4]oxadiazol-2-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro[1,2,4]tri-azolo[4,3a]pyrimidin-5-yl]-phenyl}-ethyl)-dimethyl-(1-methyl-1H-pyrazol-3-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-dimethyl-pyrimidin-2-ylmethyl-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-dimethyl-pyrazin-2-ylmethyl-ammonium chloride;

(2-{5-Cyano-2-[(R)-6-methoxycarbonyl-7-methyl-3-oxo-8-(3-trifluoromethyl-phenyl)-2,3,5,8-tetrahydro[1,2,4]tri-azolo[4,3a]pyrimidin-5-yl]-phenyl}-ethyl)-dimethyl-(1H-tetrazol-5-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3-a]pyrimidin-5-yl]-phenyl}-ethyl)dimethyl[1,3,4]oxadiazol-2-ylmethyl-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-dimethyl-(2-methyl-2H pyrazol-3-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-dimethyl-(1-methyl-1H-imidazol-2-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3-a]pyrimidin-5-yl]-phenyl}-ethyl)dimethyl[1,2,4]oxadiazol-3-ylmethyl-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-(2,5-dimethyl-2H-pyrazol-3-ylmethyl)-dimethyl-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)dimethyl-(2-methyl-oxazol-4-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-dimethyl-(5-methyl[1,3,4]thiadiazol-2-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-dimethyl-(2-methyl-thiazol-5-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-dimethyl-thiazol-2-ylmethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-(6-cyano-pyridin-3-ylmethyl)-dimethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-dimethyl-quinolin-8-ylmethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-[1,2,4]tri-azolo[4,3a]pyrimidin-5-yl]-phenyl}-ethyl)-isoquinolin-1-ylmethyl-dimethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-quinolin-5-ylmethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-(2-methyl-2-[1,2,4]triazol-3-ylmethyl)-ammonium chloride;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2,3-dimethyl-3H-imidazol-1-ium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-(3-hydroxy-propyl)-3H-imidazol-1-ium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-hydroxymethyl-3-methyl-3H-imidazol-1-ium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)imidazo[1,2-a]pyridin-1-ium bromide;

3-Benzyl-1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-3H-imidazol-1-ium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-phenyl-bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-3-(4-hydroxy-phenyl)-3H-imidazol-1-ium bromide;

2-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-isoquinolinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-quinolinium bromide;

and pharmaceutically acceptable salts thereof.

The therapeutic utility of the present compounds is pertinent to any disease that is known to be at least partially mediated by the action of human neutrophil elastase. For example, the present compounds can be beneficial in the treatment of chronic obstructive pulmonary disease (COPD), cystic fibrosis (CF), bronchiectasis, acute respiratory distress syndrome (ARDS), pulmonary emphysema, pneumonia and lung fibrosis.

Compounds of the invention are useful for treatment of inflammatory respiratory disorders, for example asthma (mild, moderate or severe), steroid resistant asthma, bronchitis, chronic obstructive pulmonary disease (COPD), cystic fibrosis (CF), pulmonary edema, pulmonary embolism, pneumonia, pulmonary sarcoidosis, pulmonary emphysema, silicosis, pulmonary fibrosis, pulmonary hypertension, respiratory failure, acute respiratory distress syndrome (ARDS), emphysema, chronic bronchitis, tuberculosis, aspergillosis and other fungal infections, hypersensitivity pneumonitis, vasculitic and thrombotic disorders of the lung vasculature, antitussive activity including treatment of chronic cough associated with inflammatory and secretory conditions of the airways, infection due to respiratory syncytial virus, influenza, coronavirus (including severe acute respiratory syndrome, SARS) and adenovirus, bronchiectasis and lung cancer.

The present invention is also concerned with pharmaceutical formulations comprising, as an active ingredient, a compound of the invention. Other compounds can be combined with compounds of this invention for the prevention and treatment of inflammatory diseases of the lung. Thus the present invention is also concerned with pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example budesonide, beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocortisone, desoxycorticosterone, rofleponide, etiprednol dicloacetate and the like. Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126). Steroid drugs can also additionally include next generation molecules in development with reduced side effect profiles such as selective glucocorticoid receptor agonists (SEGRAs), including ZK-216348 and AZD5423; (2) a β2-adrenoreceptor agonist, such as albuterol, bambuterol, terbutaline, fenoterol, formoterol, formoterol fumarate, salmeterol, salmeterol xinafoate, arformoterol, arfomoterol tartrate, indacaterol (QAB-149), carmoterol, BI 1744 CL, GSK159797 (milveterol), GSK59790, GSK159802, GSK642444 (vilanterol), GSK678007, GSK96108, clenbuterol, procaterol, bitolterol, LAS100977 (abediterol), BI1744CL (olodaterol) and brodxaterol; (3) a leukotriene modulator, for example montelukast, zafirlukast or pranlukast; (4) anticholinergic agents, for example selective muscarinic-3 (M3) receptor antagonists such as ipratropium bromide, tiotropium, tiotropium bromide (Spiriva®), glycopyrronium bromide, aclidinium bromide, LAS34273, GSK656398, GSK233705, GSK 573719 (umeclidinium), LAS35201, QAT370 and oxytropium bromide; (5) phosphodiesterase-IV (PDE-IV) inhibitors, for example roflumilast, cilomilast or theophylline; (6) an antitussive agent, such as codeine or dextramorphan; and (7) a non-steroidal anti-inflammatory agent (NSAID), for example ibuprofen or ketoprofen; (8) a mucolytic, for example N acetyl cysteine or fudostein; (9) an expectorant/mucokinetic modulator, for example ambroxol, hypertonic solutions (e.g. saline or mannitol) or surfactant; (10) a peptide mucolytic, for example recombinant human deoxyribonuclease I (dornase-alfa and rhDNase) or helicidin; (11) antibiotics, for example azithromycin, tobramycin and aztreonam; and (12) p38 Mitogen Activated Protein (MAP) kinase inhibitors, such as GSK 856553 and GSK 681323; (12) inhibitors of Janus Kinases (JAK) such as CP-690550 or GLPG0634; (13) Spleen Tyrosine Kinase (SYK) inhibitors such as R406, R343 or PRT062607; (14) inhibitors of delta and/or gamma isoforms of Phosphatidylinositol 3-kinase (PI3K); (15) anti-retroviral agents such as ribavirin, zanamivir or laninamivir; (16) PPAR-γ agonists such as pioglitazone and rosiglitazone.

In one aspect, the present invention provides for the use of inhaled administration of compounds of the invention in combination with other anti-inflammatory drugs and bronchodilator drug combinations (i.e. triple combination product), including but not limited to salmeterol xinafoate/fluticasone propionate (ADVAIR/SERETIDE®), vilanterol/fluticasone furoate (BREO ELLIPTA™), formoterol fumarate/budesonide (SYMBICORT®), formoterol fumarate/mometasone furoate, formoterol fumarate/beclometasone dipropionate (FOSTER®), formoterol fumarate/fluticasone propionate (FLUTIFORM®), Indacaterol/mometasone furoate, Indacaterol/QAE-397, GSK159797/GSK 685698, GSK159802/GSK 685698, GSK642444/GSK 685698, formoterol fumarate/ciclesonide, arformoterol tartrate/ciclesonide.

In another aspect, the present invention provides for the use of inhaled administration of compounds of the invention in combination with other bronchodilator drug combinations, particularly $\beta_2$ agonist/$M_3$ antagonist combinations (i.e. triple combination product), including but not limited to salmeterol xinafoate/tiotropium bromide, formoterol fumarate/tiotropium bromide, formoterol fumarate/glycopyrrolate (PT003), BI 1744 CL/tiotropium bromide, indacaterol/NVA237, indacterol/QAT-370, formoterol/LAS34273, umeclidinium/vilanterol (ANORO™), GSK159797/GSK 573719, GSK159802/GSK 573719, GSK642444/GSK 573719, GSK159797/GSK 233705, GSK159802/GSK 233705, GSK642444/GSK 233705.

The weight ratio of the first and second active ingredients can be varied and will depend upon the effective dose of each ingredient. Generally, an effective dose of each will be used.

The magnitude of prophylactic or therapeutic dose of a compound of the invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will from about 0.001 mg to about 100 mg per kg body weight of a mammal, preferably 0.01 mg to about 50 mg per kg, and most preferably 0.1 to 10 mg per kg, in single or divided doses. On the other hand, it can be necessary to use dosages outside these limits in some cases.

Another aspect of the present invention provides pharmaceutical compositions which comprise a compound of the invention and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the invention encompass any composition made by admixing a compound of the invention, additional active ingredient(s), and pharmaceutically acceptable excipients.

The pharmaceutical compositions of the present invention comprise a compound of the present invention as an active ingredient or a pharmaceutically acceptable salt thereof, and can also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Any suitable route of administration can be employed for providing a mammal, especially a human, with an effective dosage of a compound of the present invention. In therapeutic use, the active compound can be administered by any convenient, suitable or effective route. Suitable routes of administration are known, and include oral, intravenous, rectal, parenteral, topical, ocular, nasal, buccal and pulmonary (by inhalation).

Compositions suitable for administration by inhalation are known, and can include carriers and/or diluents that are known for use in such compositions. The composition can contain 0.01-99% by weight of active compound. Preferably, a unit dose comprises the active compound in an amount of 1 μs to 10 mg.

The most suitable dosage level can be determined by any known suitable method. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease to be treated.

For delivery by inhalation, the active compound is preferably in the form of microparticles. They can be prepared by a variety of techniques, including spray-drying, freeze-drying and micronisation.

By way of example, a composition of the invention can be prepared as a suspension for delivery from a nebulizer or as an aerosol in a liquid propellant, for example for use in a pressurized metered dose inhaler (PMDI). Propellants suitable for use in a PMDI are known to the skilled person, and include CFC-12, HFA-134a, HFA-227, HCFC-22 (CCl2F2) and HFA-152 (CH4F2 and isobutane).

In a preferred embodiment of the invention, a composition of the invention is in dry powder form, for delivery using a dry powder inhaler (DPI). Many types of DPI are known.

Microparticles for delivery by administration can be formulated with excipients that aid delivery and release. For example, in a dry powder formulation, microparticles can be formulated with large carrier particles that aid flow from the DPI into the lung. Suitable carrier particles are known, and include lactose particles; they can have a mass median aerodynamic diameter of greater than 90 μm.

In the case of an aerosol-based formulation, a preferred composition is:

| | |
|---|---:|
| Compound of the present invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

Compounds of the present invention can be used in combination with other drugs that are used in the treatment/prevention/suppression or amelioration of the diseases or conditions for which present compounds are useful. Such other drugs can be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the invention is preferred. Accordingly, the pharmaceutical compositions of the present invention include those that also contain one or more other active ingredients, in addition to a compound of the invention.

The agents of the present invention can be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds can be dosed as described depending on the inhaler system used. In addition to the active compounds, the administration forms can additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. NEBULATOR®, VOLUMATIC®), and automatic devices emitting a puffer spray (AUTO-HALER®), for metered aerosols, in particular in the case of powder inhalers, a number of technical solutions are available (e.g. DISKHALER®, ROTADISK®, TURBO-HALER® or the inhalers for example as described EP-A-0505321).

Methods of Synthesis.

In one aspect of the present invention, a process for the preparation of compounds of the invention (Ia), i.e. compounds of formula (I) wherein $R_1$ is hydrogen and $R_3$ is —$COXR_4$, and of compounds of the invention of formula (Ib), i.e. compounds of formula (I) wherein $R_1$ is not hydrogen and $R_3$ is —$COXR_4$, is provided, according to general synthetic routes reported in Scheme A here below.

Scheme A

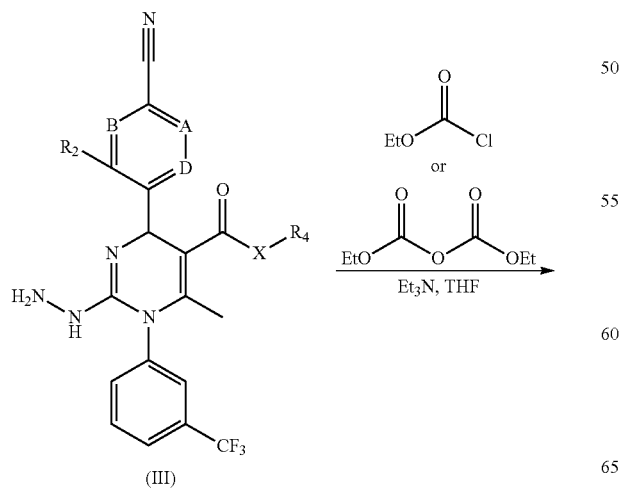

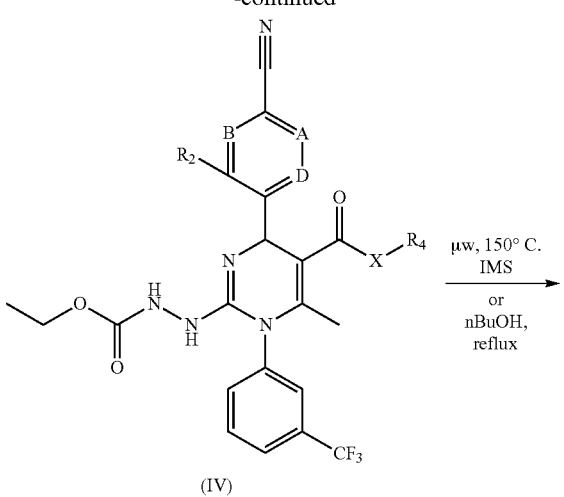

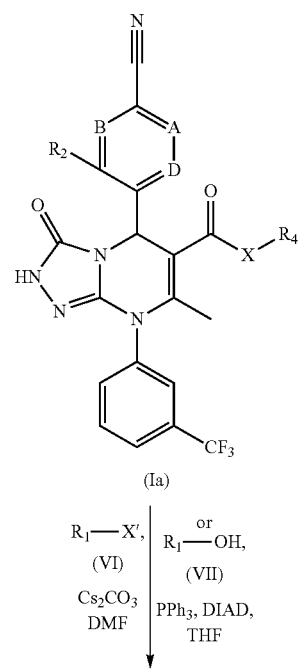

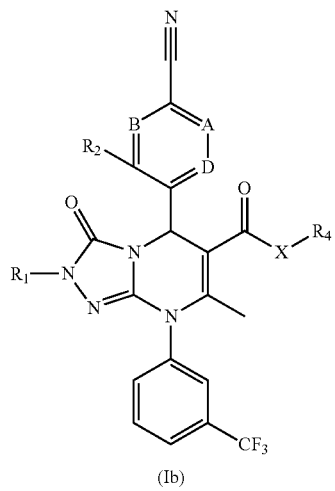

(Ib)

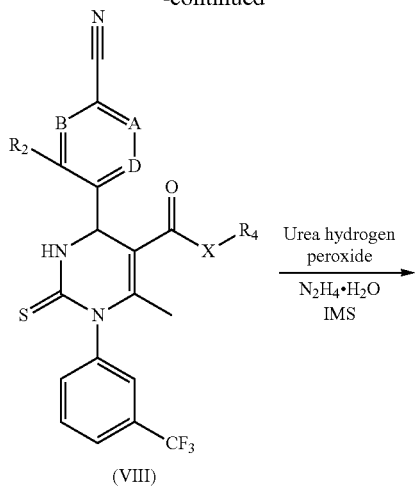

(VIII)

Compounds of formula (IV) can be prepared from compounds of formula (III) by reaction with ethyl chloroformate (or ethyl pyrocarbonate) in the presence of a base such as triethylamine in a solvent such as THF at a temperature of from 0° C. to reflux. Compounds of formula (IV) can be transformed into compounds of formula (Ia) by heating in an appropriate solvent. Suitable conditions include the use of a solvent such as IMS and heating using microwave irradiation at a temperature of up to 150° C. or conventional heating in a solvent such as n-butanol at reflux. Compounds of formula (Ia), as above defined, can be converted into compounds of formula (Ib), as above defined, by reaction with an alkyl halide (VI) of formula $R_1$—X' wherein X' is an appropriate leaving group (X'=Cl, Br, I, Tosylate etc.) in a solvent such as DMF in the presence of a base such as cesium carbonate at a temperature of from RT to 100° C. Alternatively, the transformation can be achieved by Mitsunobu reaction with an alcohol (VII) of formula $R_1OH$. Typical reagents employed are triphenyl phosphine and DIAD in a solvent such as THF.

Compounds of formula (III) wherein $R_4$ is $(C_1-C_6)$alkyl, can be prepared according to Scheme B:

Scheme B

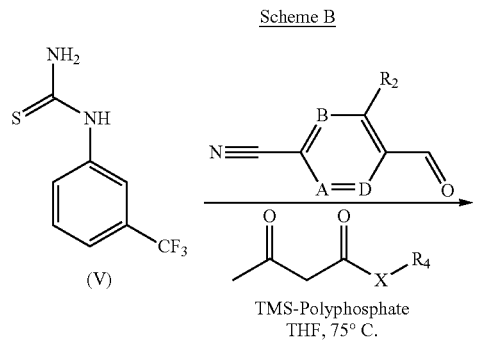

TMS-Polyphosphate
THF, 75° C.

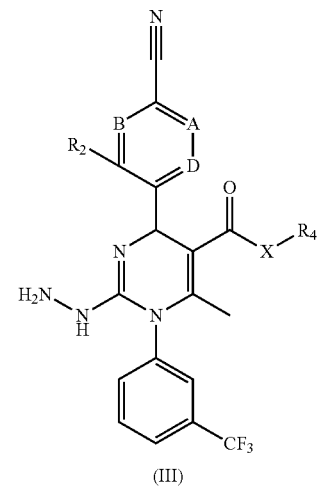

(III)

Compounds of formula (V) can be reacted with a benzaldehyde such as 3-bromo-4-formyl-benzonitrile and an acetoacetate such as ethyl acetoacetate in the presence of an acid such as TMS-polyphosphate in a solvent such as THF at a temperature of from RT to reflux to give compounds of formula (VIII), wherein $R_4$ is $(C_1-C_6)$alkyl and the other groups are as defined for compounds of formula (I). Compounds of formula (III) can be prepared from compounds of formula (VIII) by reaction with an oxidizing agent such as urea hydrogen peroxide followed by in-situ treatment with hydrazine hydrate in IMS. Furthermore compounds of formula (I)', which are compounds of formula (I) as above defined where the absolute configuration of carbon (1) is that shown herebelow can be prepared according to Scheme C.

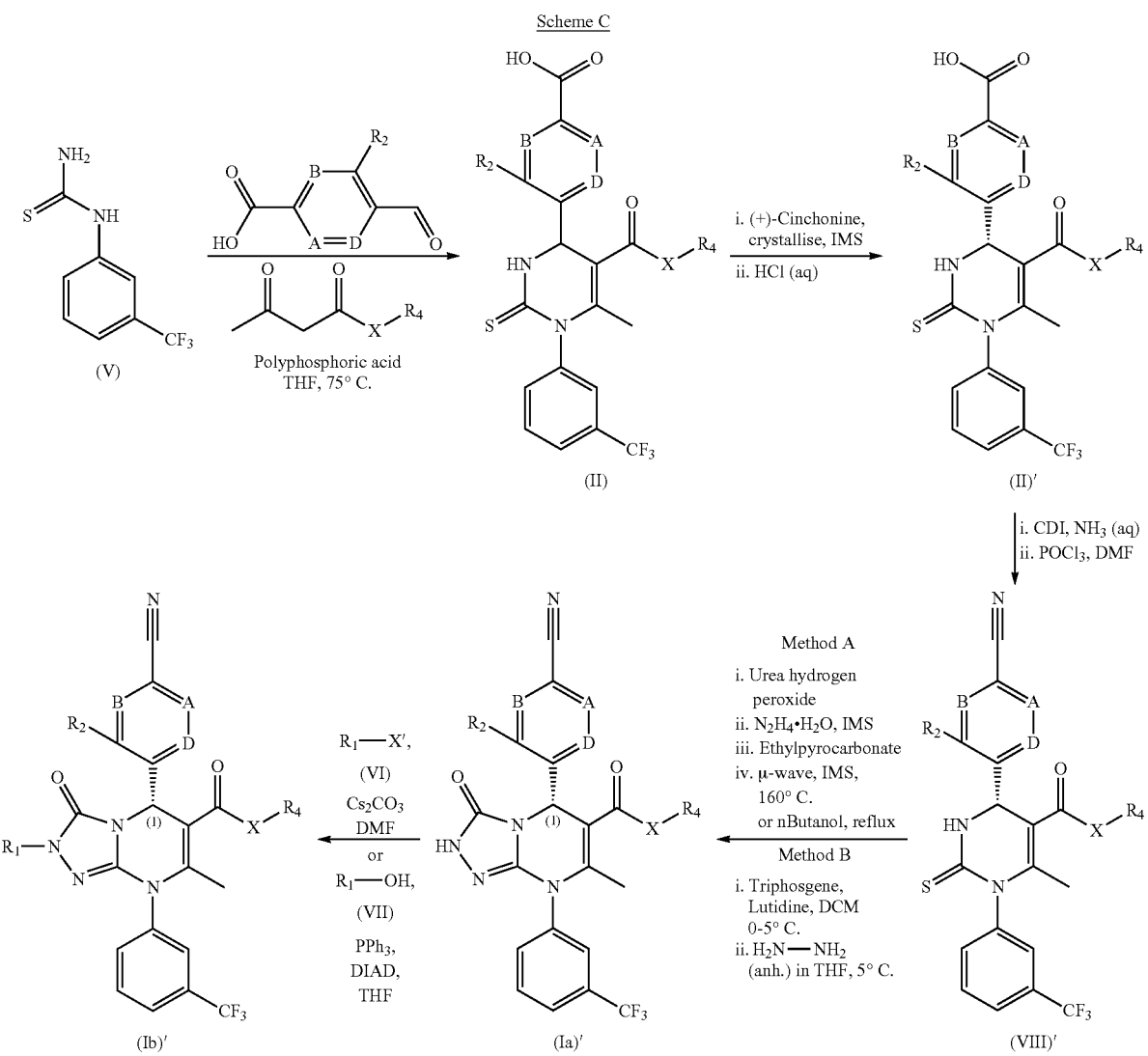

Scheme C

Compounds of formula (II) can be obtained from compounds of formula (V) by reacting with 3-bromo-4-formylbenzoic acid using a similar method described for the transformation of compounds of formula (V) to compounds of formula (VIII) in Scheme B. Compounds of formula (II)', which are compounds of formula (II) wherein the absolute configuration at stereogenic center (1) is as reported in Scheme C, can be obtained from compounds of formula (II) by forming a chiral diastereomeric salt with a suitable chiral amine such as (+)-Cinchonine in a suitable solvent such as dioxane, followed by treatment of the salt with an acid such as hydrochloric acid to give the enantiomerically pure compounds of formula (II)'. Compounds of formula (VIII)', which are compounds of formula (VIII) wherein the absolute configuration at stereogenic center (1) is as reported in Scheme C, can be prepared from compounds of formula (II)' by reaction with aqueous ammonia in the presence of a coupling agent such as carbonyl diimidazole in a solvent such as THF at a temperature of from 0° C. to RT to give the intermediate primary amide. Conversion of the amide to compounds of formula (VIII)' can be undertaken using a dehydrating agent. Suitable conditions include the use of a solvent such as DMF and a dehydrating agent such as phosphorus oxychloride at a temperature from 0° C. to RT.

Compounds of formula (Ia)' and (Ib)', which are compounds of formula (Ib) and (Ia) as above defined and wherein the absolute configuration of carbon (1) is that shown in Scheme C (Method A), can be obtained from compounds of formula (VIII)' using similar methods described for the transformation of compounds of formula (VIII) to compounds of formula of formula (Ia) and (Ib) in Schemes B and A. Alternatively, compounds of formula (Ia)' and (Ib)', which are compounds of formula (Ib) and (Ia) as above defined and wherein the absolute configuration of carbon (1) is that shown in Scheme C can be also be obtained from compounds of formula (VIII)' using method B; wherein compounds of formula (VIII)' can be reacted with a chlorocarbonyl-containing/releasing compound such as phosgene or triphosgene and anhydrous hydrazine in the presence of a base such as 2,6-lutidine in a solvent such as dichloromethane at a temperature of from 0 to 5° C. to give compounds of formula (Ia)' wherein $R_1$ is H, $R_4$ is ($C_1$-$C_6$) alkyl and the other groups are as defined for compounds of formula (I).

The skilled person would understand that by selecting the appropriate chiral amine and its absolute configuration, derivatives of formula (II)", (VIII)", Pr and (Ia)" [which are compounds of formula (II), (VIII), (Ib) and (Ia) respectively wherein the absolute configuration at stereogenic center (1) is opposite to that reported in Scheme C] can be obtained.

The skilled person can introduce, where appropriate, suitable variations to the conditions specifically described in the experimentals in order to adapt the synthetic routes to the provision of further compounds of the invention. Such variations can include, but are not limited to, use of appropriate starting materials to generate different compounds, changes in the solvent and temperature of reactions, replacement of reactives with analogous chemical role, introduction or removal of protection/de-protection stages of functional groups sensitive to reaction conditions and reagents, as well as introduction or removal of specific synthetic steps oriented to further functionalisation of the chemical scaffold.

Processes which can be used and are described and reported in Examples should not be viewed as limiting the scope of the synthetic methods available for the preparation of the compounds of the invention.

Compounds used as starting materials or intermediates can be commercially available, their preparation can be specifically described in the literature or they can be prepared according to methods available in the literature and well known to the person skilled in the art.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups can be present as such or in any properly protected form. In particular, functional groups present in the Intermediates and Examples and which could generate unwanted side reaction and by-products, need to be properly protected before the alkylation, acylation, coupling or sulfonylation takes place. Likewise, subsequent deprotection of those same protected groups can follow upon completion of the said reactions. In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups can thus include, for example, benzyl, benzyloxycarbonyl, t-butoxycarbonyl, alkyl or benzyl esters or the like, which are well known to those skilled in the art [see, for a general reference, T. W. Green; Protective Groups in Organic Synthesis (Wiley, N.Y. 1981), which is incorporated herein by reference in its entirety].

Likewise, selective protection and de-protection of any of the said groups, for instance including carbonyl, hydroxyl or amino groups, can be accomplished according to very well-known methods commonly employed in organic synthetic chemistry.

Optional salt formation of the compounds of formula (I) can be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

The diastereoisomers of compounds of formula (I), where available, can be obtained according to methods well known in the art, such as for example by preparative HPLC or by chromatographic purifications. A racemic mixture of compounds of formula (I) can as well be separated using preparative HPLC and a column with a chiral stationary phase, or resolved to yield individual enantiomers using methods well-known in the art. Furthermore, chiral intermediates can be resolved and used to prepare chiral compounds of the invention.

From all of the above, it should be clear to the skilled person that the above process, comprehensive of any variant thereof for the preparation of suitable compounds of the invention, can be conveniently modified so as to adapt the reaction conditions to the specific needs, for instance by choosing appropriate condensing agents, solvents and protective groups, as the case can be.

Compounds of formula (XII), wherein $R_3$ is a group —$COXR_4$, $R_1$ is as defined above, A, B and D are CH and $R_2$ is bromine or other suitable activating group taken from the group, but not exclusively, Cl, I, OTf, can be prepared from compounds of formula (IX) according to Scheme D here below reported:

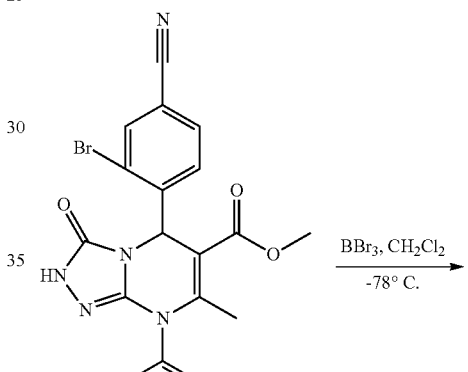

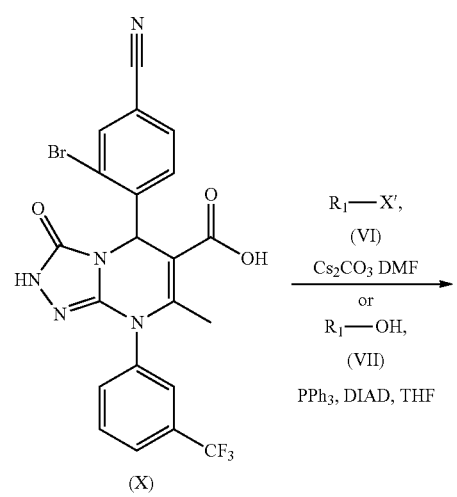

27

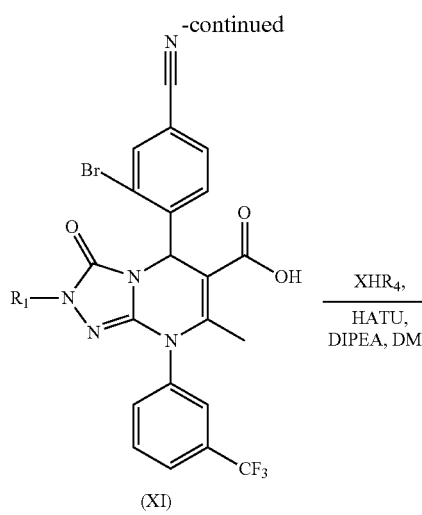

(XI)

→ XHR₄, HATU, DIPEA, DMF

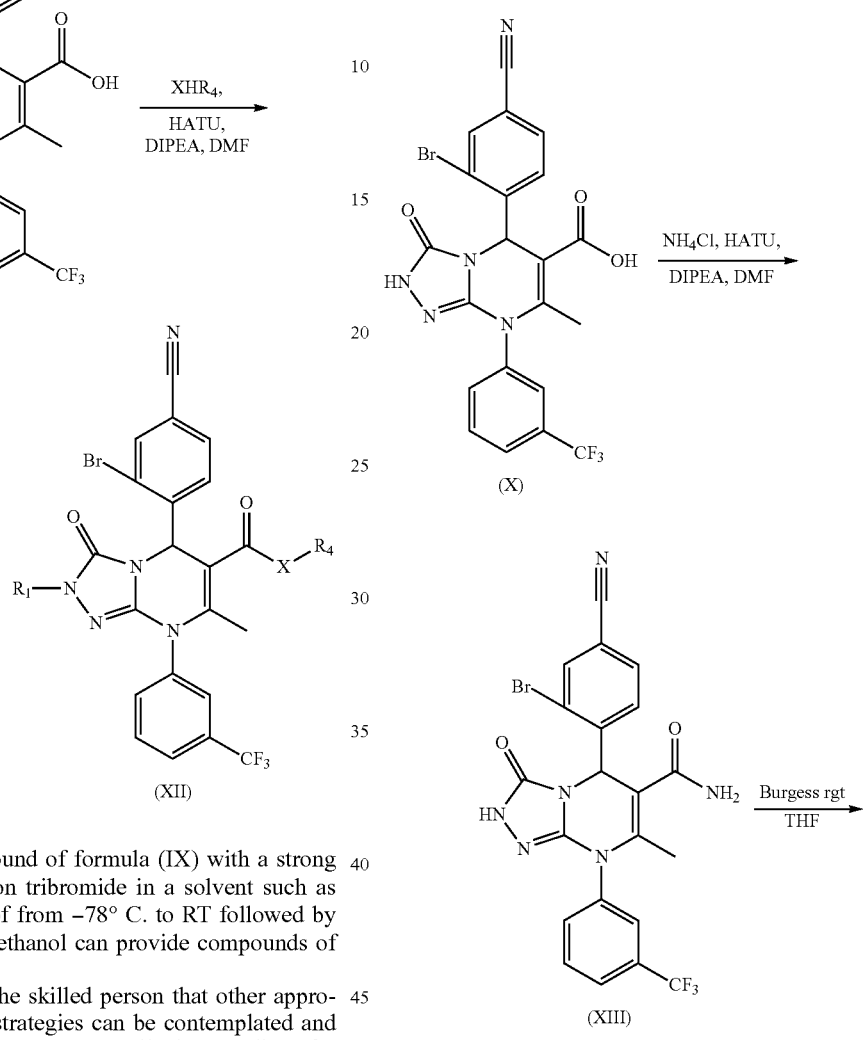

28

DMF in the presence of a base such as triethylamine at a temperature of from RT to 80° C. The synthetic route shown in Scheme D would be of benefit in introducing —XR₄ substituents at a late stage.

Scheme E (X) → NH₄Cl, HATU, DIPEA, DMF (XIII) → Burgess rgt, THF

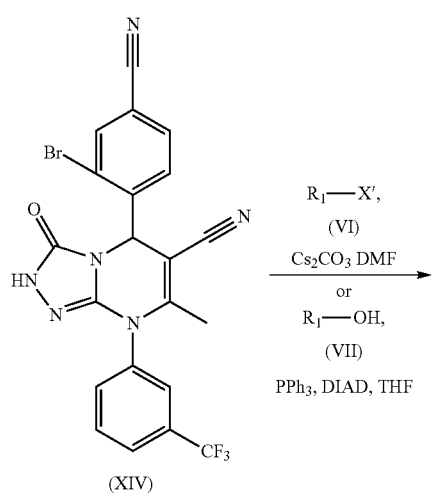

(XII)

Treatment of a compound of formula (IX) with a strong Lewis acid such as boron tribromide in a solvent such as DCM at a temperature of from −78° C. to RT followed by quench with water or methanol can provide compounds of formula (X).

It should be clear to the skilled person that other appropriate protecting group strategies can be contemplated and that the acid (X) represents a versatile intermediate for further functionalisation as well as for preparation of compounds of formula (XII).

It is in fact to be underlined that many of the synthetic routes herebelow described starting from compounds of formula (IX) (i.e. in Schemes F, G and H) can be applicable, as the skilled person would understand, to compounds of formula (X) and (XII) also, to get to additional compounds of formula (I), (Ia) and (Ib).

By way of example, by appropriate derivatisation of a compound of formula (X), as above defined, into a compound of formula (XI) wherein $R_1$ is not hydrogen, corresponding compounds of formula (XII) wherein $R_1$ is not hydrogen can be obtained. Compounds of formula (XI) can be obtained from compounds of formula (X) using the methods described for the transformation of compounds of formula (Ia) to compounds of formula (Ib) in Scheme A.

Compounds of formula (XII) can be prepared from compounds of formula (XI) by reaction with an alcohol or amine XHR₄ such as ammonia or 2-methoxy-ethanol in the presence of a coupling agent such as HATU in a solvent such as (XIV) → $R_1$—X′, (VI) Cs₂CO₃ DMF or $R_1$—OH, (VII) PPh₃, DIAD, THF -continued

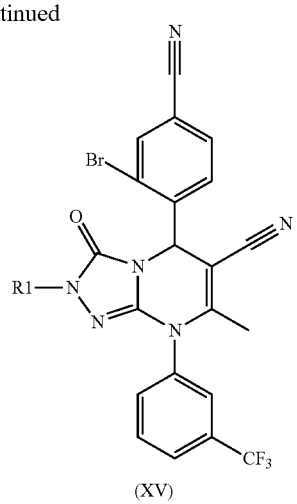

(XV)

Compounds of formula (XIV) and (XV), i.e. compounds of formula (XII) wherein $R_3$ is a group —CN, can be prepared according to Scheme E from compounds of formula (X). Compounds of formula (XIII), which are compounds of formula (XII) wherein $R_1$ is H and $XR_4$ is $NH_2$, can be prepared by reaction with ammonia, in the presence of a coupling agent such as HATU, in a solvent such as DMF, in the presence of a base such as triethylamine, at a temperature of from RT to 80° C.

Compounds of formula (XIV) can be prepared from compounds of formula (XIII) by reaction with a dehydrating agent such as Burgess reagent in a solvent such as THF at a temperature of from RT to reflux. Compounds of formula (XV) can be obtained from compounds of formula (XIV) using the methods described for the transformation of compounds of formula (Ia) to compounds of formula (Ib) in Scheme A.

It will then be apparent to the skilled person that by adaptation of synthetic routes herebelow described in schemes F or G and starting from compounds of formula (XIV) or (XV), compounds of formula (Im), i.e. compounds of formula (I) wherein $R_3$ is a group cyano, can be prepared.

Compounds of formula (Ic), (Id), (Ie) and (If) i.e. compounds of formula (I) wherein $R_3$ is a group —$COXR_4$, X is oxygen, $R_4$ is a methyl group, $R_1$ is as defined above, A, B and D are CH and $R_2$ is respectively a group as reported in Scheme F where $R_y$ can have different meanings according to those described for compounds of formula (I), can be prepared from compounds of formula (IX) according to Scheme F here below reported:

Scheme F

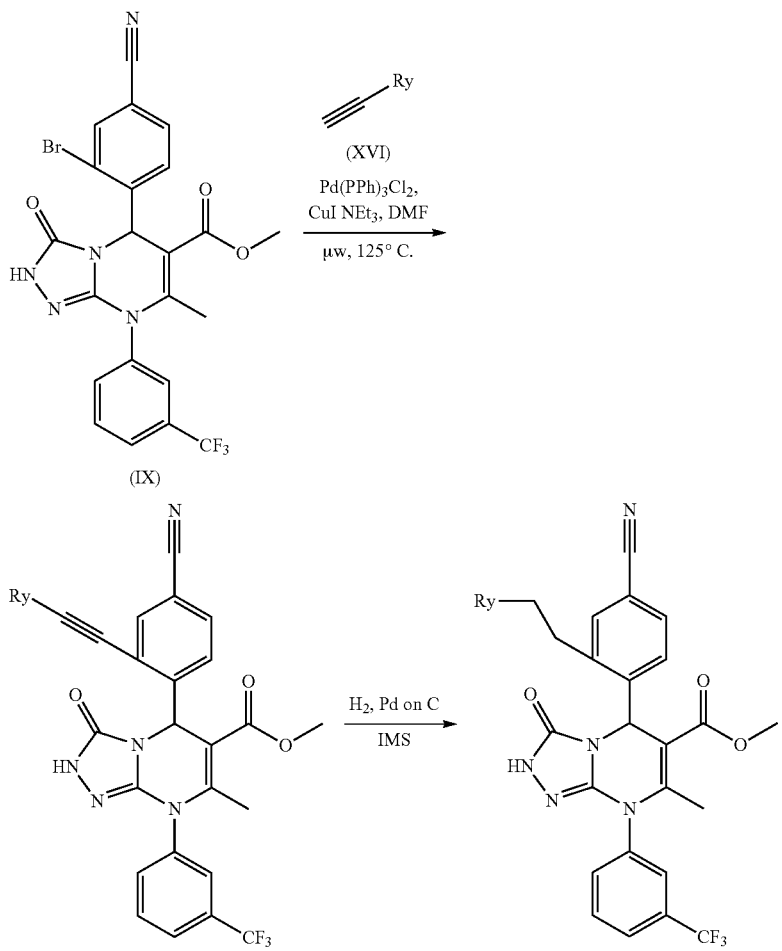

-continued (Ic)

R₁—X',
(VI)
Cs₂CO₃ DMF
or
R₁—OH,
(VII)
PPh₃, DIAD, THF (Id)

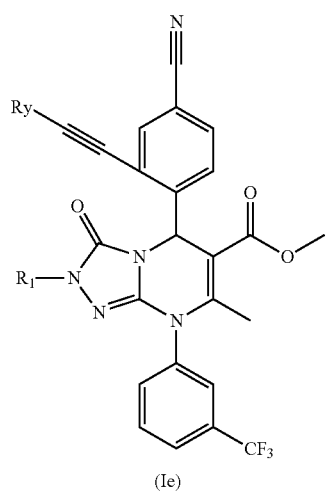

(Ie)

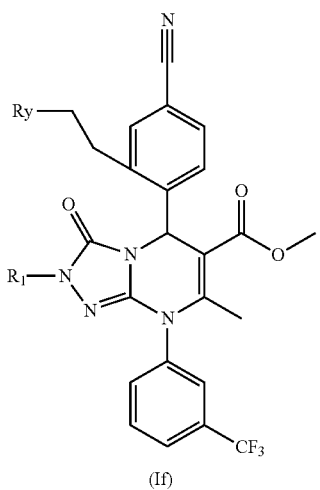

(If)

The transformation of compounds of formula (IX) into compounds of formula (Ic) can be achieved by reaction with a suitably unsubstituted acetylene compound (XVI) in the presence of a catalytic mixture such as bis(triphenylphosphine) palladium(II) dichloride and copper (I) iodide with a base such as triethylamine in a solvent such as DMF at a temperature of up to 120° C., typically using microwave irradiation. Compounds of formula (Id) can be prepared from compounds of formula (Ic) by hydrogenation using a catalyst such as Pd/C in a solvent such as IMS.

Furthermore, compounds of the formula (Ie) and (If) can be obtained from compounds of formula (Ic) and (Id), respectively, using the methods described for the transformation of compounds of formula (Ia) to compounds of formula (Ib) in Scheme A.

Compounds of formula (Ig) i.e. compounds of formula (I) wherein $R_3$ is a group —$COXR_4$, $R_1$ is as defined above, X is oxygen, $R_4$ is a methyl group, A, B and D are CH and $R_2$ is a methylene linked tertiary amine $NR_{24}R_{39}$, quaternary amine $N^+R_{24}R_{25}R_{39}$ or imidazolium ($R_{22}R_{38}$) can be prepared from compounds of formula (IX) according to Scheme G below:

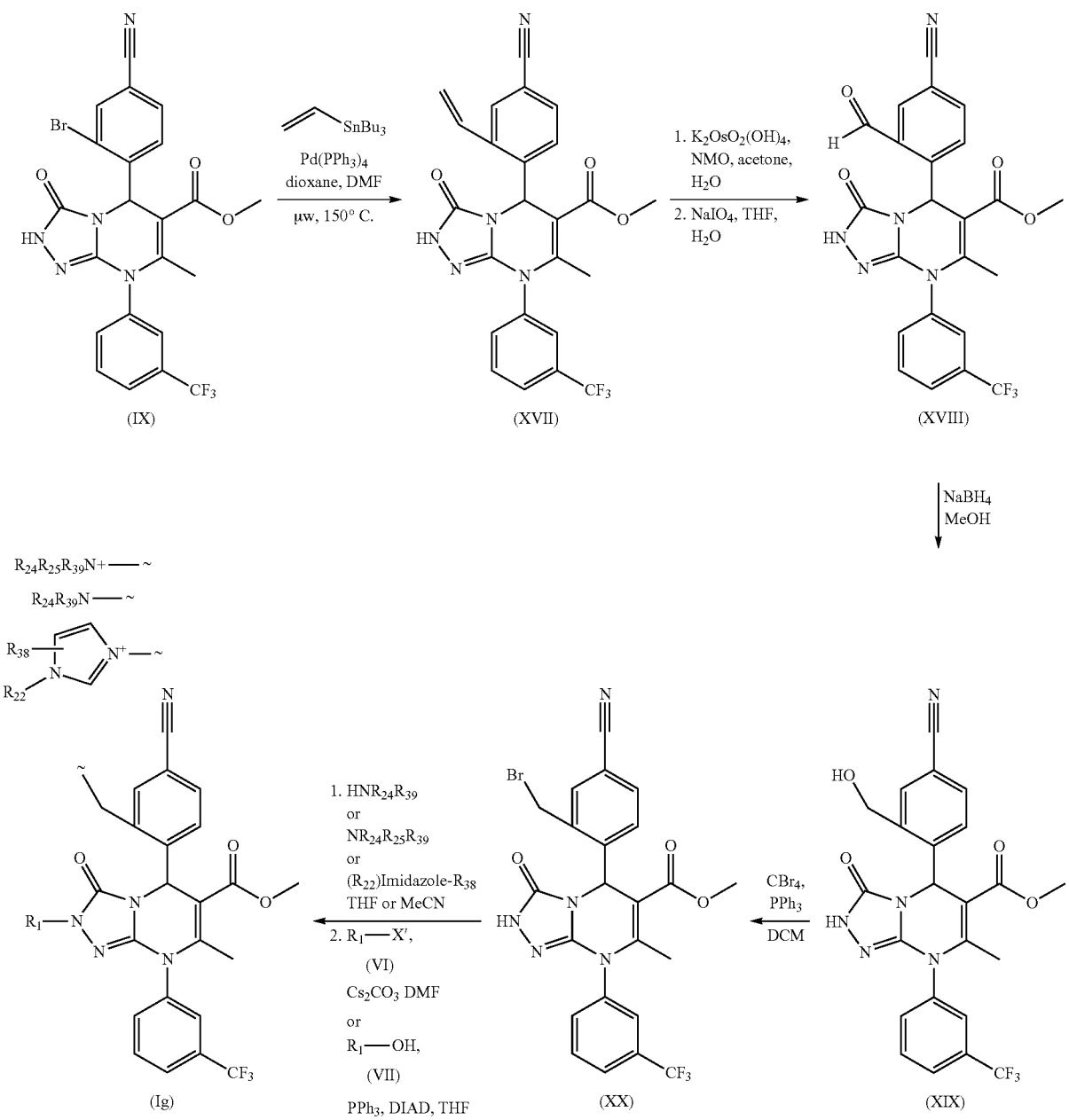

Scheme G

The transformation of compounds of formula (IX) into compounds of formula (XVII) can be achieved by reaction with a suitable nucleophile such as vinyltributyl stannane in the presence of a catalyst such tetrakis(triphenylphosphine) palladium(0) in a solvent such as dioxane or DMF at a temperature of up to 150° C., typically using microwave irradiation. Compounds of formula (XVIII) can be prepared from compounds of formula (XVII) following a 2 step procedure starting with oxidation using a catalyst such as potassium osmate dihydrate with a co-oxidant such as N-methylmorpholine-N-oxide in a solvent mixture such as acetone/water at RT. Compounds of formula (XVIII) are thus obtained following cleavage of the intermediate diol using a suitable reagent such as sodium periodate in an appropriate solvent mixture such as THF/water. Compounds of formula (XIX) can be obtained from compounds of formula (XVIII) by reduction, typically using a reducing agent such as sodium borohydride in a solvent such as MeOH. Compounds of formula (XX) can be obtained from compounds of formula (XIX) by bromination. Suitable conditions involve reaction with an appropriate brominating agent such as carbon tetrabromide with triphenyl phosphine in a solvent such as dichloromethane at a temperature of from 0° C. to RT. Conversion of compounds of formula (XX) to either tertiary or quaternary amines of formula (Ig) can be achieved by reaction with a suitable secondary amine of formula $NHR_{24}R_{39}$ or tertiary amine of formula $NR_{24}R_{25}R_{39}$, respectively, in a suitable solvent such as THF or MeCN. Alternatively, quaternary amines of the formula (Ig) can be obtained sequentially from tertiary amines of formula (Ig) followed by reaction with a suitable electrophile such as methyl bromide in a suitable solvent such as MeCN at RT. Furthermore, conversion of compounds of formula (XX) to imidazolium compounds of formula (Ig) can be achieved by reaction with a suitably substituted imidazole-containing compound, imidazole $R_{22}R_{38}$.

It should be clear to the skilled person that the aldehyde (XVIII) represents a versatile intermediate for further functionalisation as well as for preparation of compounds of formula (Ig).

Compounds of formula (Ih), i.e. compounds of formula (I) wherein $R_3$ is a group —$COXR_4$, $R_1$ is as defined above, A, B and D are CH, X is oxygen, $R_4$ is a methyl group, and $R_2$ is an amide-linked group as reported in Scheme H where $R_x$ can have different meanings according to those described for compounds of formula (I), can be prepared from compounds of formula (XVIII) according to Scheme H below:

Scheme H

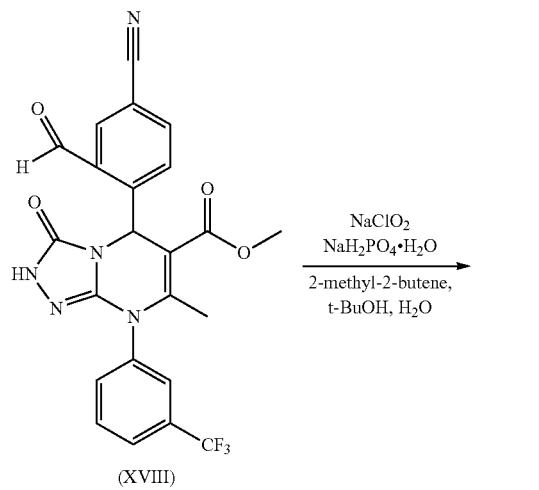

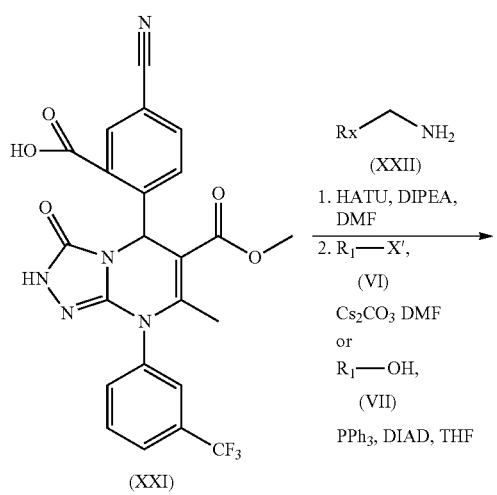

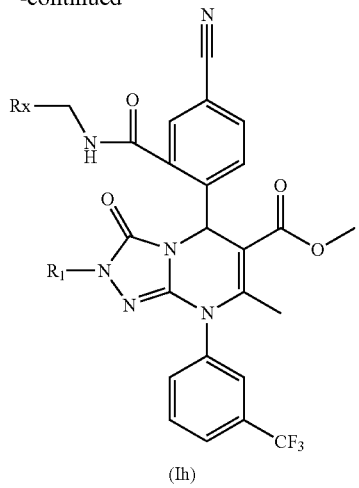

Compounds of formula (XXI) can be prepared from compounds of formula (XVIII) using suitable oxidizing reagent agent such as sodium chlorite and an appropriate co-reductant such as 2-methyl-2-butene in a suitable solvent mixture such as tert-butanol/water and using an appropriate base such as sodium dihydrogenphosphate at RT. Typically, compounds of formula (Ih) where $R_1$=H can be obtained from compounds of formula (XXI) by reaction with an amine (XXII) in the presence of a coupling agent such as HATU in a solvent such as DMF in the presence of a base such as triethylamine at a temperature of from RT to 80° C.

Furthermore, compounds of the formula (Ig) and (Ih) where $R_1 \neq H$ can be obtained from compounds of formula (Ig) and (Ih) where $R_1$=H, using the methods described for the transformation of compounds of formula (Ia) to compounds of formula (Ib) in Scheme A. It should be clear to the skilled person that other appropriate protecting group strategies can be contemplated at R1 and that the incorporation of R1 (where $R_1 \neq H$) can be possible at any intervening step in the synthesis of compounds of the invention, (Ig) and (Ih).

A compound of formula (XXVI) can be prepared according to Scheme J from a compound of formula (IX). A compound of formula (XXIV) can be prepared using Heck coupling chemistry by reaction with an appropriately substituted vinyl compound (XXIII) in the presence of an appropriate catalyst/ligand system such as Herrmann-Beller catalyst/tributylphosphine tetrafluoroborate in a solvent such as tetraethylene glycol or dimethoxyethane in the presence of a base such as pentamethylpiperidine at a temperature of from RT to 160° C. A compound of formula (XXV) can be prepared from compounds of formula (XXIV) following hydrolysis and reduction steps using an acid such as trifluoroacetic acid in a solvent such as DCM at −10° C. to give the intermediate aldehyde, and a reducing agent such as sodium borohydride in a solvent such as MeOH at a temperature of from 0° C. to RT to give a compound of formula (XXV). A compound of formula (XXVI) can be prepared from a compound of formula (XXV) using a mixture of carbon tetrabromide/triphenyl phosphine in a solvent such as DCM at a temperature of from 0° C. to 50° C.

Scheme J

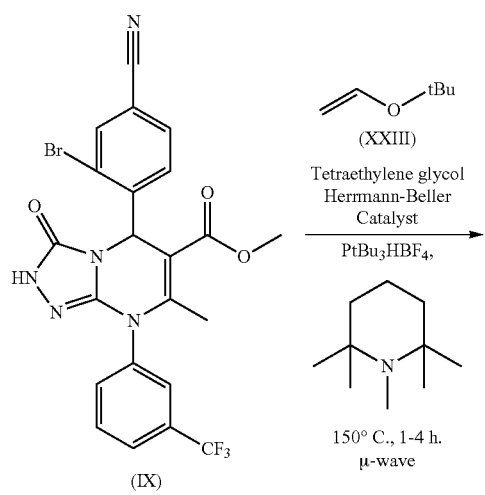

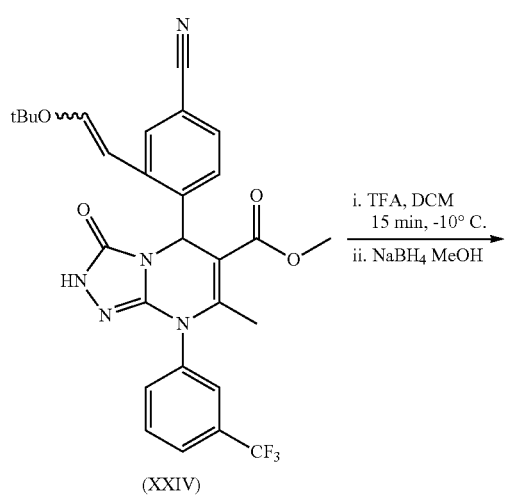

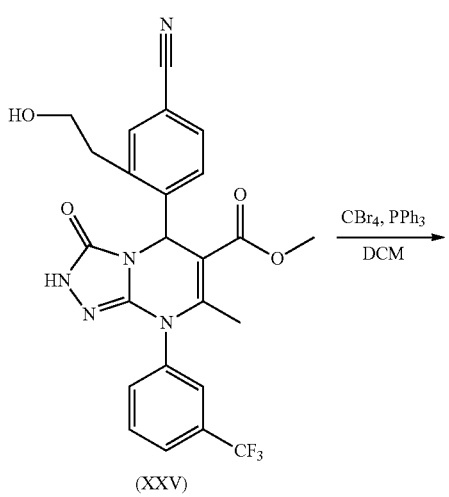

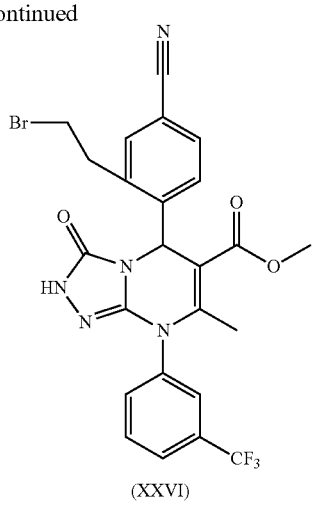

Compounds of formula (Ij), (Ik) or (In), i.e. compounds of formula (I) where $R_2$ is defined as $(C_1\text{-}C_4)$alkyleneN$^+$ $R_{24}R_{25}R_{39}$, a group $(C_1\text{-}C_4)$alkyleneNR$_{24}$R$_{39}$, a group $[CH_2]_y G[CH_2]_j CH_2$-imidazolium$(R_{22}R_{38})$, respectively as substituents, can be prepared according to Scheme K. Similarly, compounds of formula (Ij), (Ik) or (In), i.e. compounds of formula (I) where $R_2$ is defined as a group alkyne-Ry or $C(O)NHCH_2Rx$ can be prepared according to Scheme K. Compounds of formula (Ij), (Ik) or (In) can also be prepared similarly from compounds of formula (XXVII) or (XXVI).

Scheme K

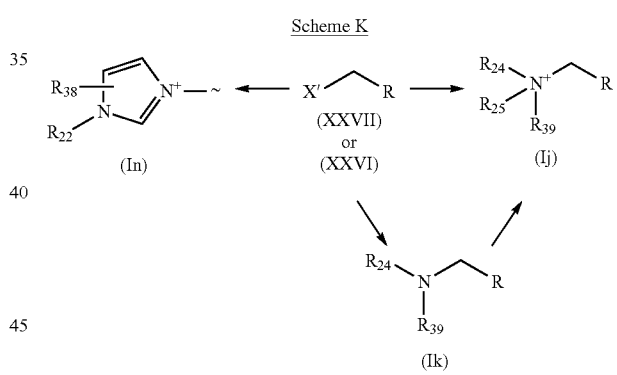

Compounds of formula (Ij) can be obtained directly by alkylation reaction of an appropriate tertiary amine $R_{24}R_{25}R_{39}N$, such as dimethyl-(1-methyl)-1H-imidazol-4-ylmethyl)-amine or dimethyl-thiazol-4-ylmethylamine, with compounds of formula (XXVII) wherein X' is an appropriate leaving group (X'=Cl, Br, I, Tosylate etc.) and group —CH$_2$R represents the portion of a compound of formula (Ij) remaining out of its substitution by a group $(C_1\text{-}C_4)$ alkyleneN$^+$R$_{24}$R$_{25}$R$_{39}$. Typical conditions could involve heating a tertiary amine in a solvent such as ethanol or THF at elevated temperatures of between 60° C. and 150° C., using microwave irradiation.

Alternatively, the transformation of compounds of formula (XXVII) to compounds of formula (Ij) can be achieved via the tertiary amine (Ik) where $R_{24}$ and $R_{39} \neq H$. Tertiary amine compounds of formula (Ik) can be prepared from compounds of formula (XXVII) by reaction with a secondary amine $R_{24}R_{39}NH$. Typical reaction conditions include the use of a base such as cesium carbonate or potassium carbonate in a solvent such as DMF at RT. The conversion of compounds of formula (Ik), where $R_{24}$ and $R_{39}\neq H$, to compounds of formula (Ij) can be obtained using methylating agents such as methyl bromide, methyl iodide or methyl benzenesulfonate. Typical reaction conditions consist of the use of a solvent such as MeCN or acetone at a temperature of between RT to 60° C. under conventional or microwave heating.

Furthermore, secondary amine compounds of formula (Ik) ($R_{24}$ is H) can also be prepared from compounds of formula (XXVII) by reaction with a suitable primary amine $R_{39}NH_2$, to give a secondary amine.

Compounds of formula (In) can be obtained directly by alkylation reaction of an appropriate imidazole-containing compound such as 1-methyl-1H-imidazole with compounds of formula (XXVII), wherein X' is an appropriate leaving group (X'=Cl, Br, I, Tosylate etc.) and group —CH$_2$R represents the portion of a compounds of formula (In) remaining out of its substitution by a group or a group $[CH_2]_yG[CH_2]_jCH_2$—N$^+$imidazolium($R_{22}R_{38}$). Typical conditions could involve heating compounds of formula (XXVII), with 1-methyl-1H-imidazole in a solvent such as MeCN or THF at elevated temperatures of between 50° C. and 100° C., using microwave irradiation.

Compounds of formula (Ij), (Ik) or (In), i.e. compounds of formula (I) which incorporate a group $R_y$ or $R_x$ (see Scheme F/H) defined as $(C_1-C_4)$alkyleneN$^+R_{24}R_{25}R_{39}$, a group $(C_1-C_4)$alkyleneNR$_{24}R_{39}$, or a group:

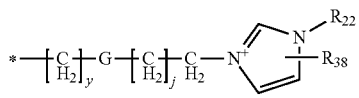

respectively as substituents, can be also be prepared according to Scheme K from compounds of formula (XXVI).

Other features of the invention will become apparent in the course of the following descriptions of exemplary embodiments which are given for illustration of the invention and are not intended to be limiting thereof.

EXAMPLES

General Experimental Details

Reactions were not carried out under an inert atmosphere unless specified and all solvents and commercial reagents were used as received.

Purification by chromatography refers to purification using the CombiFlash® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 μm and nominal 60 Å porosity. Fractions containing the required product (identified by TLC and/or LCMS analysis) were pooled, the organic fraction removed by evaporation, and the remaining aqueous fraction lyophilized, to give the final product. Where thin layer chromatography (TLC) has been used, it refers to silica gel TLC using plates, typically 3×6 cm silica gel on aluminium foil plates with a fluorescent indicator (254 nm), (e.g. Fluka 60778). Microwave experiments were carried out using a Biotage Initiator 60™ which uses a single-mode resonator and dynamic field tuning. Temperature from 40-250° C. can be achieved, and pressures of up to 30 bar can be reached.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Compound names were generated using the Autonom 2000 feature in MDL ISIS™/Draw 2.5 SP2 software.

Analytical LC-MS Conditions.

LC-MS Method 1.

The Waters ZQ quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 μL/min split to the ESI source with in-line HP1100 PDA detector)

MS ionization method—Electrospray (positive and negative ion)

LC-MS Method 2.

Waters Micromass ZMD quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (100 μL split to MS with in-line UV detector)

MS ionisation method—Electrospray (positive and negative ion)

LC-MS Method 3.

Waters Micromass ZQ2000 mass spectrometer with a C18-reverse-phase column (100×2.1 mm Acquity BEH with 1.7 μm particle size) maintained at 40° C., elution with A: water+0.1% formic acid; B: MeCN+0.1% formic acid. Alternatively, where specified, a C18-reverse-phase (100× 2.1 mm Acquity UPLC BEH Shield 1.7 μm particle size) column was used. Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |

-continued

| Gradient - Time | flow (mL/min) | % A | % B |
|---|---|---|---|
| 7.00 | 0.4 | 95 | 5 |
| 8.00 | 0.4 | 95 | 5 |

Detection—MS, UV PDA
MS ionization method—Electrospray (positive/negative ion).
LC-MS Method 4.

Waters Platform LC quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (Split—200 μL/min split to the ESI source with in-line HP1100 DAD detection)
MS ionization method—Electrospray (positive and negative ion).
LC-MS Method 5.

Waters VG Platform II quadrupole spectrometer with a C18-reverse-phase column (30×4.6 mm Luna 3 μm particle size), elution with A: water+0.1% formic acid; B: MeCN+0.1% formic acid.
Gradient:

| Gradient - Time | flow (mL/min) | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (Split—200 μL/min split to the ESI source with in-line HP1050 DAD detection)
MS ionization method—Electrospray (positive and negative ion)
MDAP System:
Instrumentation: Agilent 1260 infinity purifications system.
Agilent 6100 series single Quadrupole LC/MS
Column: XSELECT CSH Prep C18 5 μm OBD, 30×150 mm, RT
Mobile Phase A: 0.1% aqueous formic acid
Mobile Phase B: 0.1% formic acid in acetonitrile
Flow: 60 ml/min
Gradient Program: 10%-95%, 22 min, centred around a specific focused gradient Sample Injection of a 20-60 mg/mL solution in DMSO (+optional formic acid and water).
Abbreviations Used in the Experimental Section:
DCM Dichloromethane
DMF N,N-dimethylformamide
DMSO Dimethylsulphoxide
Et$_2$O Diethyl ether
EtOAc Ethyl acetate
HPLC High performance liquid chromatography
LC-MS Liquid chromatography-mass spectrometry
MeCN Acetonitrile
MDAP Mass Directed Automatic Purification
NBS N-Bromosuccinimide
NMO N-Methylmorpholine-N-Oxide
Rt Retention time
RT Room temperature
THF Tetrahydrofuran In the procedures that follow, some of the starting materials are identified through an "Intermediate" or "Example" number. This is provided merely for assistance to the skilled chemist. The starting material may not necessarily have been prepared from the batch referred to.

When reference is made to the use of a "similar" or "analogous" procedure, as will be appreciated by those skilled in the art, such a procedure can involve minor variations, for example reaction temperature, reagent/solvent amount, reaction time, work-up conditions or chromatographic purification conditions.

Example 1

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-thiazol-4-ylmethyl-ammonium formate

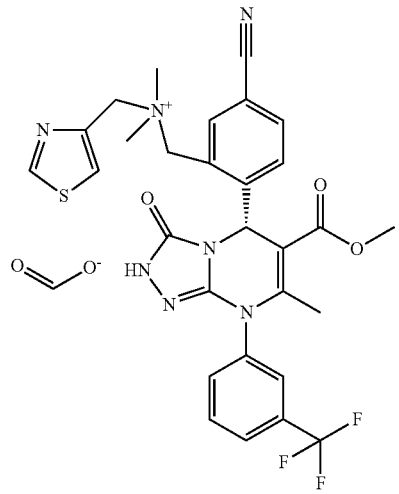

Intermediate 1

3-Bromo-4-dibromomethylbenzoic acid

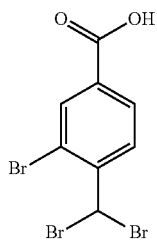

3-Bromo-4-methylbenzoic acid (910 g, 4.23 mol, 1.0 eq.) and NBS (2010 g, 11.29 mol, 2.67 eq.) were dissolved in DCM (8.5 L) in a 20 L flange flask fitted with a mechanical stirrer. A slurry of AIBN (50 g, 0.3 mol, 0.07 eq.) in DCM (1 L) was then added, and the mixture irradiated under strong light (500 W) under a reflux condenser under an $N_2$ atmosphere. The internal temperature of the reaction rose from 17° C. to 41° C. and the initial white suspension became a pale orange suspension as it reached gentle reflux. After a total of 72 h the reaction was complete and water (5 L) was added to the cloudy orange solution, which was stirred at RT for 1 h. The orange biphasic mixture was then left to stand overnight and was then concentrated in vacuo to give an orange distillate and a tan suspended solid. The solid was then collected by filtration, washed with water (2 L) and suction dried for 2 h to give the title compound as a tan colored damp solid (1860 g).

LCMS (Method 1): Rt=3.39 min, m/z 369, 371, 373, 375 [M–H]

$^1$H NMR (300 MHz, DMSO): δ 8.14-8.03 (3H, m), 7.36 (1H, s).

Intermediate 2

3-Bromo-4-formylbenzoic acid

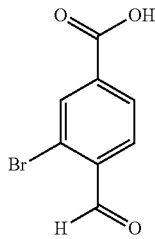

Intermediate 1 (1860 g, 4.23 mol, 1.0 eq.) was suspended in water (5 L) and the slurry was heated to an internal temperature of 40° C. Solid $Na_2CO_3$ (1460 g, 13.77 mol, 3.25 eq.) was then added in small portions over a period of 20 min. Foaming resulted on initial addition, so EtOAc (0.2 L) was added to collapse the foam and suppress any further foaming. Once addition was complete, the brown suspension was heated to 90° C. over 40 min, then stirred at 90° C. for 90 min, then cooled to 40° C. over 90 min. EtOAc (1.5 L) was added, followed by addition of aqueous concentrated HCl via dropping funnel (0.7 L), resulting in vigorous evolution of $CO_2$ gas and evaporation of most of the EtOAc. Further EtOAc (1 L) was added to wash the foaming product from the condenser and the walls of the reactor, then additional EtOAc (0.3 L) was added and the thick slurry was stirred at RT overnight. The slurry was then heated to 40° C. and further aqueous concentrated HCl was added via dropping funnel with vigorous stirring over 45 min, resulting in $CO_2$ gas evolution, evaporation of most of the EtOAc and formation of a solid. Stirring was ceased, and the solid floated to the top of the aqueous mixture (pH 1). The majority of the aqueous layer was separated (ca. 5 L) and then 2-MeTHF (5 L) was added. The clear aqueous layer was then removed, and the organic layer diluted to 10 L with additional 2-MeTHF, and warmed to 50° C. to give a dark orange solution. The organic layer was then washed with 1 M HCl (0.5 L), evaporated, and azeotroped with toluene to afford the title compound as a tan coloured solid (960.3 g).

LCMS (Method 4): Rt 2.73 min, m/z 227, 229 [M–H]

$^1$H NMR (300 MHz, DMSO): δ 10.26 (1H, d, J=0.8 Hz), 8.20 (1H, d, J=1.5 Hz), 8.08-8.04 (1H, m), 7.95 (1H, d, J=8.0 Hz).

Intermediate 3

4-(2-Bromo-4-carboxyphenyl)-6-methyl-2-thioxo-1-(3-trifluoromethylphenyl)-1,2,3,4-tetrahydropyrimidine-5-carboxylic acid methyl ester

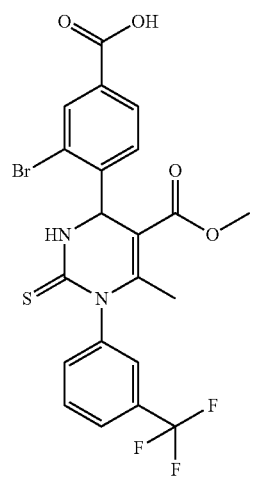 [SMILES: COC(=O)C1=C(C)N(c2cccc(C(F)(F)F)c2)C(=S)N[C@@H]1c1ccc(C(=O)O)cc1Br]

Intermediate 2 (458 g, 2 mol, 1.0 eq.), methyl acetoacetate (274.4 g, 255 mL, 2.36 mol, 1.18 eq.) and 3-trifluoromethylphenyl thiourea (519 g, 2.36 mol, 1.18 eq.), were charged to a 10 L jacketed reactor under a $N_2$ atmosphere, and suspended in THF (4.6 L) and while stirring, was cooled to –10° C. (internal temperature –3° C.). Polyphosphoric acid (1650 g, 3.6 wt eq.), was prewarmed in a water bath at 50° C., then added in one portion, resulting in an immediate exotherm, and the internal temperature rose to 19° C. The resulting orange mixture was then warmed to 75° C. in 10° C. increments to a gentle reflux, and the reaction stirred at this temperature for 20 h. The reaction was then cooled to 20° C. and the bulk of THF removed in vacuo to give a dark orange viscous oil, which was then diluted with water (5 L) and $Et_2O$ (5 L). The aqueous layer was separated and extracted again with $Et_2O$ (2×2 L) and the combined organics were subsequently washed with water (1 L), brine (1 L) and dried ($Na_2SO_4$) and filtered through Celite to remove any fine particulates. The filtered solution was then concentrated in vacuo to give a viscous orange gum which was resuspended in $Et_2O$ (ca. 1.5 L) and left to stand overnight. The resulting suspension was filtered and the solid collected was rinsed with $Et_2O$ (0.5 L) and dried in a vacuum oven at 50° C. (8 mbar) for 4 days to afford the title compound (754 g).

LCMS (Method 1): Rt 3.52 min, m/z 529, 531 [M+H]$^+$ $^1$H NMR (300 MHz, DMSO): δ 10.15 (1H, d, J=3.5 Hz), 8.11 (1H, d, J=1.6 Hz), 8.05 (1H, dd, J=8.1, 1.7 Hz), 7.92-7.64 (5H, m), 5.80 (1H, d, J=2.9 Hz), 3.53 (3H, s), 2.07 (3H, s).

Intermediate 4

(S)-4-(2-Bromo-4-carboxy-phenyl)-6-methyl-2-thioxo-1-(3-trifluoromethyl-phenyl)-1,2,3,4-tetrahydro-pyrimidine-5-carboxylic acid methyl ester

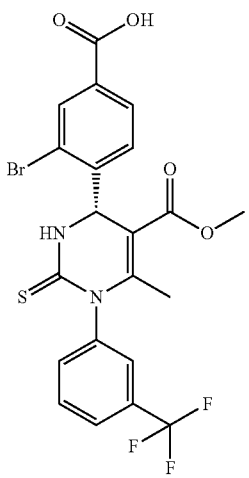

Intermediate 3 (151.7 g, 0.29 mol, 1.0 eq.) was dissolved in dioxane (2 L) and heated to 80° C. The resulting suspension was filtered to remove any inorganic residues and the clear solution was again heated to 80° C. and (+)-Cinchonine (88 g, 0.29 mol, 1.0 eq,) was added, resulting in a clear solution. The resultant mixture was allowed to cool slowly and crystallize. After 3 h, the resulting solid was filtered and washed with cold dioxane. The solid was resuspended in hot dioxane (85° C.) and allowed to cool and crystallise overnight. The resulting crystals were filtered off, washed with cold dioxane, and the solid recrystallized again from hot dioxane. The final recrystallization solids were filtered off and air-dried to give the intermediate (+)-Cinchonine salt as a white solid 83.2 g (68%).

The optical purity of the resolved (+)-Cinchonine salt was determined by partitioning between 1 M HCl and EtOAc; the organic layer was separated, concentrated in vacuo and then redissolved in 20% IPA/n-heptane with 0.1% TFA and subjected to chiral analytical HPLC (ChiralPak IA, 5 μM 4.6×250 mm), eluting with 20% IPA/n-heptane (+0.1% TFA) at 1 mL/min and a wavelength of 254 nm. The racemic product was also checked by chiral HPLC; Retention times of 14.8 and 42.5 mins were observed for a racemic sample and the desired enantiomer was eluted at 42.5 mins and was found to be greater than 99.5 ee %.

The intermediate (+)-Cinchonine salt (83.2 g, 101.75 mmol) was liberated by partitioning between EtOAc (1 L) and 1 M HCl (1 L). The aqueous layer was extracted again with EtOAc (2×0.5 L) and the combined organic layers washed with 1 M HCl (0.5 L), then brine (0.25 L), dried ($Na_2SO_4$) and concentrated in vacuo to give the title compound as a white solid (45.45 g).

Intermediate 5

(S)-4-(2-Bromo-4-carbamoyl-phenyl)-6-methyl-2-thioxo-1-(3-trifluoromethyl-phenyl)-1,2,3,4-tetrahydro-pyrimidine-5-carboxylic acid methyl ester

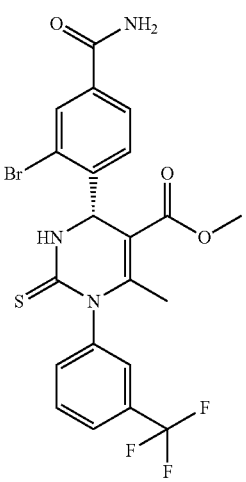 [SMILES: COC(=O)C1=C(C)N(c2cccc(C(F)(F)F)c2)C(=S)N[C@@H]1c1ccc(C(N)=O)cc1Br]

Intermediate 4 (93.8 g, 0.18 mol) was dissolved in THF (1 L) and 1,1'-carbonyldiimidazole (57.5 g, 0.35 mol, 2.0 eq.) was added portion-wise and left to stir at RT until gas evolution had ceased. Aqueous ammonia solution (33%, 330 mL) was then added drop-wise, ensuring the internal temperature did not exceed 10° C. (exotherm observed on initial addition). The reaction was left to stir at RT for 2 h, then brine was added and the layers were separated. The organic phase was washed with aqueous 1 M HCl (2×) and the acidic layer further extracted with EtOAc. The combined organic layers were washed with brine, dried ($Na_2SO_4$), filtered and concentrated in vacuo to afford the title compound as a colourless foam (87.3 g).

LCMS (Method 2): Rt 3.44 min, m/z 528, 530 [M+H]$^+$ $^1$H NMR (300 MHz, DMSO): δ 10.12 (1H, d, J=2.6 Hz), 8.12 (1H, s), 8.11 (1H, d, J=1.7 Hz), 7.96 (1H, dd, J=8.1, 1.7 Hz), 7.88-7.77 (2H, m), 7.75-7.63 (3H, m), 7.54 (1H, s), 5.78 (1H, s), 3.54 (3H, s), 2.07 (3H, s).

Intermediate 6

(S)-4-(2-Bromo-4-cyanophenyl)-6-methyl-2-thioxo-1-(3-trifluoromethylphenyl)-1,2,3,4-tetrahydropyrimidine-5-carboxylic acid methyl ester

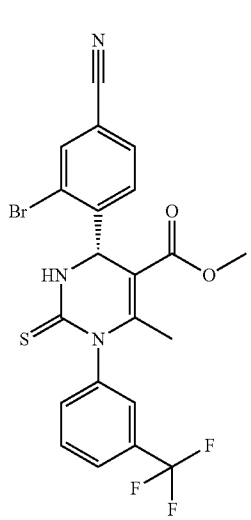 [SMILES: COC(=O)C1=C(C)N(c2cccc(C(F)(F)F)c2)C(=S)N[C@@H]1c1ccc(C#N)cc1Br]

Intermediate 5 (87.3 g, 0.165 mol) was dissolved in DMF (400 mL) and cooled to 0-5° C. in an ice bath. Phosphorous oxychloride (62.0 g, 37.0 mL, 2.5 eq.) was then added drop-wise, ensuring the internal temperature did not exceed 10° C. Once addition was complete, the yellow solution was stirred at 0-5° C. for 15 min, then poured into a mixture of solid 2 M $Na_2CO_3$ and ice. A yellow precipitate formed and the slurry was aged for 1 h, then the solid was filtered, washed with water and dried in a vacuum oven over $P_2O_5$ at 40-45° C. NMR analysis of the resultant product still showed starting material remaining so the reaction was repeated again using a further 20 mL phosphorous oxychloride. NMR of the resulting solid showed the product to be an adduct with $POCl_3$. Therefore, the solid was dissolved in absolute EtOH (1000 mL) and the suspension warmed to aid dissolution. Saturated aqueous $NaHCO_3$ solution (250 mL) was then added and the mixture was heated to 40° C. and stirred for 2 h. The resultant mixture was then poured into water (500 mL) and the resulting white solid filtered off, washed with water and air dried to afford the title compound (77.5 g).

LCMS (Method 2): Rt 3.94 min, m/z 510, 512 [M+H]$^+$ $^1$H NMR (300 MHz, DMSO): δ 10.18 (1H, d, J=2.7 Hz), 8.24 (1H, d, J=1.5 Hz), 7.96 (1H, dd, J=8.0, 1.6 Hz), 7.89-7.76 (3H, m), 7.74-7.64 (2H, m), 5.8 (1H, s), 3.53 (3H, s), 2.06 (3H, s).

Intermediate 7

(S)-5-(2-Bromo-4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester

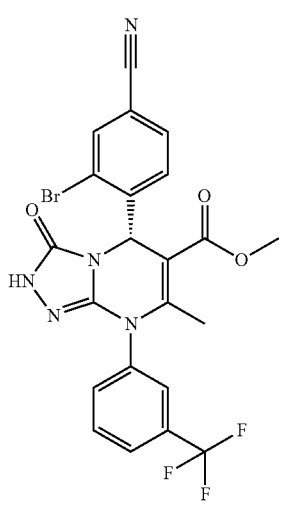 [SMILES: COC(=O)C1=C(C)N(c2cccc(C(F)(F)F)c2)c2n[nH]c(=O)n2[C@@H]1c1ccc(C#N)cc1Br]

Intermediate 6 (49.8 g, 98 mmol) was dissolved in DCM (830 mL), 2,6-lutidine (32.4 mL, 278 mmol, 2.85 eq.) was added and the solution was cooled to 2° C. While stirring, triphosgene (9.17 g, 30.9 mmol, 0.32 eq) was then added slowly over a period of 3 min. After 5 min, the reaction was warmed to RT and stirred for 25 min. The reaction was cooled to 8° C. and the solution was then transferred via cannula to a cooled (7° C.) mixture of hydrazine solution (1 M in THF, 278 mL) and MeCN (250 mL). The reaction was stirred at 7° C. for a further 10 min and then allowed to warm to RT. After 2.25 h, the reaction mixture was washed with water, then with 50% saturated brine and the organic phase was dried ($Na_2SO_4$), filtered and concentrated in vacuo. The resulting gum was azeotroped with toluene and triturated with $Et_2O$ (200 mL) to afford a solid which was filtered off, washed with $Et_2O$ and dried to afford the title compound as a cream colored solid (31.75 g).

LCMS (Method 5): Rt 3.51 min, m/z 534, 536 [M+H]$^+$ $^1$H NMR (300 MHz, $CDCl_3$): δ 8.36 (1H, s), 7.88 (1H, d, J=1.5 Hz), 7.83-7.79 (1H, m), 7.73 (1H, t, J=8.0 Hz), 7.65-7.60 (2H, m), 7.59-7.50 (2H, m), 6.39 (1H, d, J=1.0 Hz), 3.62 (3H, s), 2.25 (3H, d, J=1.0 Hz).

The chiral purity was analysed by Chiralpak IC chiral HPLC column (5 μm particle size, 5% MeOH/DCM, flow rate 5 mL/min) and gave Rt=5.83 min. (100% ee). A racemic sample gave Rt for first and second eluting enantiomers of 3.58 and 5.85 min, respectively.

Intermediate 8

(R)-5-(4-Cyano-2-vinyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

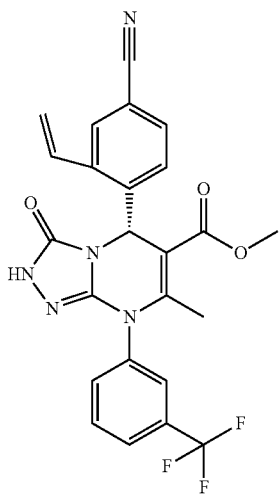 [SMILES: C=Cc1cc(C#N)ccc1[C@@H]1C(C(=O)OC)=C(C)N(c2cccc(C(F)(F)F)c2)c2n[nH]c(=O)n21]

Intermediate 7 (1.42 g, 2.66 mmol), tributylvinyl stannane and palladium-tetrakis(triphenylphosphine) were dissolved in dioxane (18 mL) and a few drops of DMF and the resulting solution was purged with $N_2$ for 5 minutes. The reaction mixture was then heated at 150° C. for 1 h using microwave irradiation. The reaction mixture was purified by silica-gel chromatography eluting with a gradient of 0-70% EtOAc in cyclohexane followed by trituration with $Et_2O$ to yield the title compound as an off-white solid (1.02 g).

LC-MS (Method 2): Rt=3.52 min, m/z=482 [M+1-1]$^+$

Intermediate 9

(R)-5-(4-Cyano-2-formyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

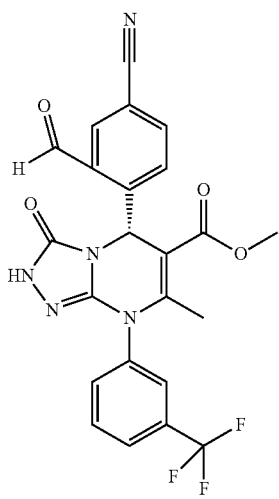 [SMILES: COC(=O)C1=C(C)N(c2cccc(C(F)(F)F)c2)c2n[nH]c(=O)n2[C@@H]1c1ccc(C#N)cc1C=O]

Intermediate 8 (0.8 g, 1.66 mmol) was suspended in acetone (4.5 mL) and water (0.5 mL). Potassium osmate dihydrate (31 mg, 0.08 mmol) was added, followed by NMO (0.39 g, 3.32 mmol) and the reaction mixture stirred vigorously at RT for 18 h. $Na_2S_2O_5$ (4 g, 21.06 mmol) was then added and the reaction diluted with DCM and stirred for a further 20 min. The resultant mixture was filtered through Celite and then evaporated in vacuo. The resultant residue was taken up in THF (8 mL) and water (8 mL) and then cooled to 0° C. before sodium periodate (0.71 g, 3.32 mmol) was added. The reaction mixture was allowed to warm to RT and then stirred for 3 h before being diluted with saturated aqueous $NaHCO_3$ and then extracted with EtOAc. The combined organic layers were washed with saturated aqueous $NaHCO_3$ then brine, dried ($Na_2SO_4$) and evaporated in vacuo. The resulting residue was purified by silica-gel chromatography eluting with a gradient of 50-70% EtOAc in cyclohexane to yield the title compound as a pink solid (0.56 g).

LC-MS (Method 1): Rt=2.98 min, m/z=484 [M+H]$^+$

Intermediate 10

(R)-5-(4-Cyano-2-hydroxymethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

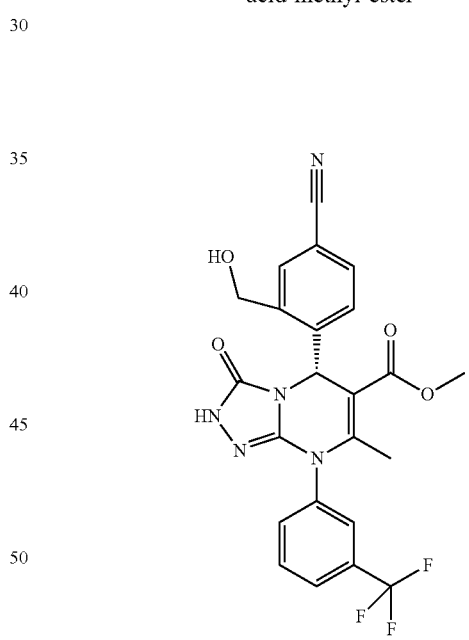

Intermediate 9 (273 mg, 0.57 mmol) was dissolved in MeOH (5 mL) and sodium borohydride (26 mg, 0.68 mmol) was added and the reaction stirred at RT for 2 h. The mixture was evaporated in vacuo and the residue partitioned between EtOAc and water and the phases separated. The organic layer was washed with brine, dried ($Na_2SO_4$) and evaporated in vacuo. The resulting residue was triturated with $Et_2O$, filtered and the solid collected to yield the title compound as an off-white solid (184 mg).

LC-MS (Method 2): Rt=3.24 min, m/z=486 [M+H]$^+$

Intermediate 11

(R)-5-(2-Bromomethyl-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

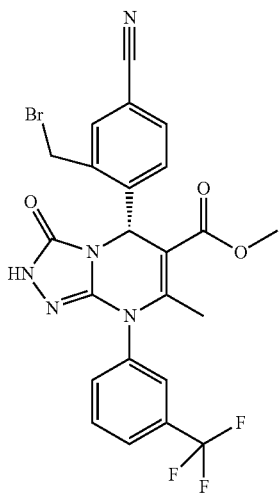 [SMILES: COC(=O)C1=C(C)N(c2cccc(C(F)(F)F)c2)c2n[nH]c(=O)n2[C@@H]1c1ccc(C#N)cc1CBr]

Intermediate 10 (approximately 0.1 mmol) was dissolved in DCM (1 mL) and the solution cooled to 0° C. Carbon tetrabromide (40 mg, 0.12 mmol) was added, followed by triphenylphosphine (29 mg, 0.11 mmol) and the reaction stirred at RT. After 5 h, further portions of carbon tetrabromide (53 mg, 0.16 mmol) and triphenylphosphine (42 mg, 0.16 mmol) were added and stirring continued at RT for 16 h. The reaction mixture was diluted with DCM and washed with water followed by brine, dried (Na$_2$SO$_4$) and evaporated in vacuo. The resulting residue was purified by silica-gel chromatography eluting with a gradient of 50-80% EtOAc in cyclohexane to give the title compound as a white solid (19 mg).

LC-MS (Method 1): Rt=3.12 min, m/z=548 [M+H]$^+$

Intermediate 12

Dimethyl-thiazol-4-ylmethylamine

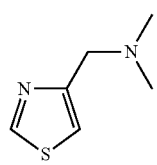

A solution of 1,3-thiazole-4-carboxaldehyde (0.50 g, 4.42 mmol) in DCM (45 mL) was treated with acetic acid (505 µL, 8.85 mmol) and dimethylamine (2 M in THF, 4.42 mL, 8.85 mmol) and stirred for 2 h. Sodium triacetoxyborohydride (1.88 g, 8.85 mmol) was added and the mixture stirred overnight. The reaction was quenched by pouring into saturated aqueous NaHCO$_3$ containing some 1 N NaOH to achieve pH 9, and extracted into EtOAc. The organic extract were washed with brine, dried and concentrated in vacuo to give a yellow residue. This was purified by chromatography eluting from 0-10% (2M NH$_3$ in MeOH) in DCM and afforded the title compound as a an amber oil (280 mg).

$^1$H NMR (300 MHz, CDCl$_3$): □8.77 (1H, d, J=2.0 Hz), 7.18 (1H, m), 3.66 (2H, s), 2.30 (6H, s).

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-thiazol-4-ylmethyl-ammonium formate (Example 1)

Intermediate 12 (153 mg, 1.08 mmol) was added to a solution of Intermediate 11 (100 mg, 0.18 mmol) in MeCN (0.3 mL) contained in a large microwave vial. This was sealed and heated at 50° C. with stirring for 18 h. Solvents were removed in vacuo and the crude product was diluted with EtOAc and extracted into water. These aqueous extracts were washed with EtOAc and then concentrated in vacuo. The resultant residue was purified by MDAP to yield the title compound as a white solid (74 mg).

LC-MS (Method 3): Rt=3.46 min, m/z=610.2 [M]$^+$

1H NMR (400 MHz, DMSO) δ 11.53 (1H, bs), 9.32 (1H, s), 8.44 (1.5H, s, formate), 8.25-8.14 (2H, m), 8.11 (1H, bs), 8.05-8.00 (1H, m), 7.95-7.79 (4H, m), 6.53 (1H, s), 5.25-5.08 (2H, m), 4.98 (2H, s), 3.51 (3H, s), 3.26-3.11 (6H, m), 2.07 (3H, s).

Example 2

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(1-methyl-1H-imidazol-4-ylmethyl)-ammonium formate

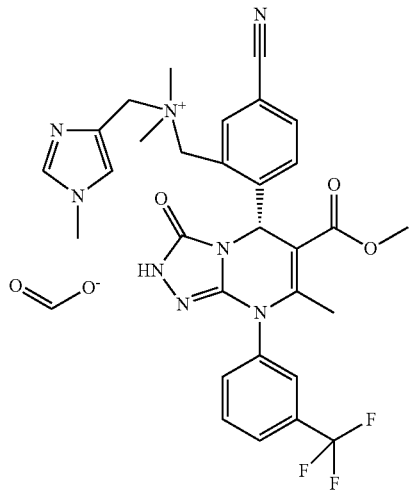

Intermediate 13

Dimethyl-(1-methyl)-1H-imidazol-4-ylmethyl)-amine

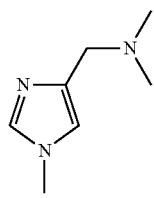

A solution of 1-methyl-1H-imidazole-4-carboxaldehyde (0.71 g, 6.45 mmol) in THF (60 mL) was treated with acetic acid (738 μL, 12.90 mmol) and dimethylamine (2 M in THF, 6.45 mL, 12.90 mmol) and stirred for 2 h. Sodium triacetoxyborohydride (2.74 g, 12.90 mmol) was added and the mixture stirred overnight. The reaction was diluted with EtOAc and poured into saturated aqueous NaHCO₃. The aqueous phase was concentrated in vacuo and the resultant residue suspended in MeOH-DCM. This was filtered and the filtrate concentrated in vacuo. The crude product was purified using an SCX-2 cartridge and the relevant eluent was concentrated in vacuo to give a residue which was further purified by chromatography eluting from 0-10% (2M NH₃ in MeOH) in DCM to afford the title compound as an amber oil (340 mg).

¹H NMR (300 MHz, DMSO): □7.44 (1H, s), 6.91 (1H, s), 3.60 (3H, s), 3.24 (2H, s), 2.11 (6H, s).

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(1-methyl-1H-imidazol-4-ylmethyl)-ammonium formate (Example 2)

The title compound was prepared from Intermediate 11 (100 mg, 0.18 mmol) using an analogous method to Example 1. Following MDAP purification the title compound was obtained as a white solid (43 mg).

LC-MS (Method 3): Rt=3.28 min, m/z=607.3 [M]⁺

1H NMR (400 MHz, DMSO) δ 11.25 (1H, very bs), 8.38 (1.9H, s, formate), 8.29-8.25 (1H, m), 8.11 (1H, bs), 8.04-7.99 (1H, m), 7.95-7.87 (2H, m), 7.87-7.77 (3H, m), 7.47 (1H, s), 6.54 (1H, s), 5.16-5.02 (2H, m), 4.71-4.61 (3H, s), 3.72 (2H, s, obscured), 3.51 (3H, s), 3.12 (3H, s), 3.10 (3H, s), 2.07 (3H, s).

Example 3

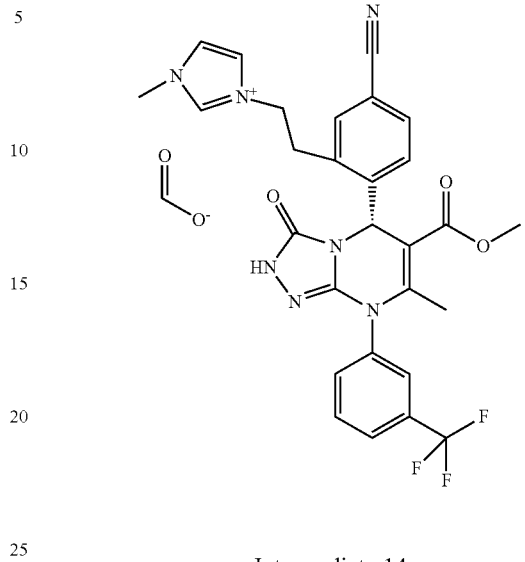

Intermediate 14

(R)-5-[2-(2-tert-Butoxy-vinyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

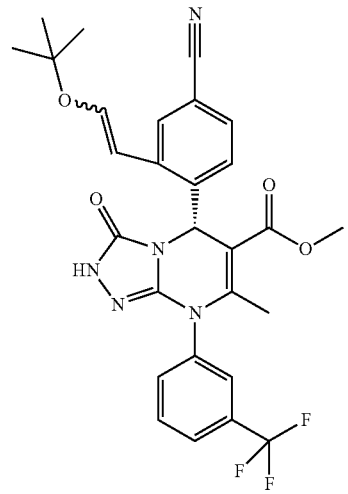 [SMILES: COC(=O)C1=C(C)N(c2cccc(C(F)(F)F)c2)c2n[nH]c(=O)n2[C@@H]1c1ccc(C#N)cc1C=COC(C)(C)C]

An autoclave was charged with a mixture of Intermediate 7 (10 g, 18.72 mmol), 2-methyl-2-vinyloxy-propane (6.55 g, 65.50 mmol), tri-tertiary-butyl phosphonium tetrafluoroborate (540 mg, 1.86 mmol), Herrmann-Beller catalyst (trans-di(μ-acetato)bis(0-di-o-tolyl-phosphino)benzyl)dipalladium (II)) (880 mg, 0.94 mmol), 1,2,2,6,6-pentamethylpiperidine (11.5 g, 74.20 mmol). Tetra-ethylene glycol (140 mL) was added and the resulting solution degassed under Argon. The mixture was then heated at 150° C. for 1 h. The mixture was cooled, diluted with EtOAc and aqueous 10% citric acid and the organic extract was washed with water and brine, then dried (Na₂SO₄) and concentrated in vacuo. The resultant residue was purified by chromatography, eluting with 25-75% EtOAc in cyclohexane to give the title compound as a [3:1] mixture of E/Z isomers and as a yellow foam (7.95 g).

LC-MS (Method 5): Rt=3.87 min, m/z=554.2 [M+H]⁺

Intermediate 15

(R)-5-[4-Cyano-2-(2-hydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

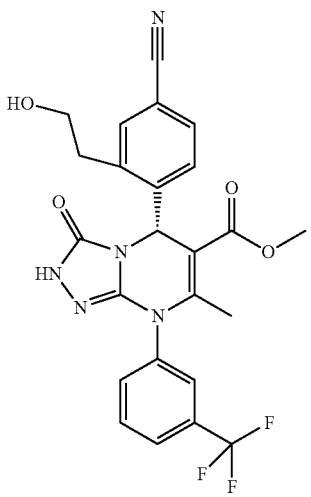 [SMILES: COC(=O)C1=C(C)N(c2cccc(C(F)(F)F)c2)c2n[nH]c(=O)n2[C@@H]1c1ccc(C#N)cc1CCO]

A solution of Intermediate 14 (5.83 g, 10.53 mmol) and water (568 EL, 31.59 mmol) in DCM (50 mL) was cooled to −10° C. using a salt/ice bath and treated drop-wise with TFA (4.03 mL, 52.66 mmol). After stirring at −10° C. for 1 h 45 min, the resulting solution was treated with an aqueous solution of potassium carbonate (1 g/mL, 30 mL). Sodium borohydride (2 g, 52.9 mmol) was then added in one portion, followed by MeOH (8 mL). The reaction was stirred at −10° C. for 15 min, then at RT for 2 h. The reaction was quenched with water and diluted with DCM. The aqueous phase was further extracted with DCM and the combined organic extracts were washed with brine, dried (MgSO₄) and concentrated in vacuo. The resultant residue was purified by chromatography, eluting with a gradient of 0-5% MeOH in DCM, to give the title compound as a white foam (4.25 g).

LC-MS (Method 5): Rt=3.17 min, m/z=500.1 [M+H]⁺

Intermediate 16

(R)-5-[2-(2-Bromo-ethyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

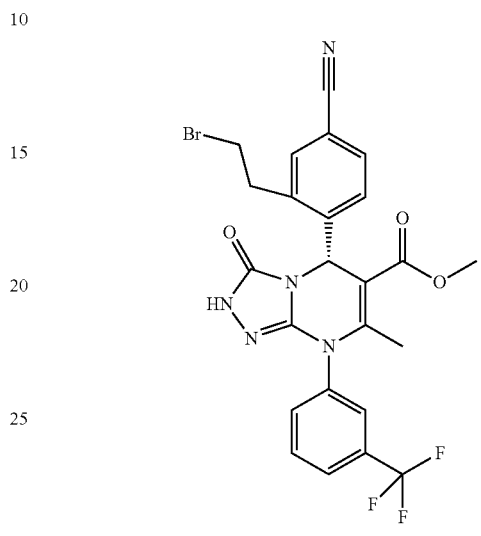

The title compound was prepared from Intermediate 15 (0.30 g, 0.60 mmol) using an analogous method to that used for Intermediate 11 and gave the desired compound as a white solid (0.24 g).

LC-MS (Method 4): Rt=3.83 min, m/z=562.1 [M(⁷⁹Br)+H]⁺

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-methyl-3H-imidazol-1-ium formate
(Example 3)

A solution of Intermediate 16 (75 mg, 0.133 mmol) and N-methyl-imidazole (160 mL, 2 mmol) in acetonitrile (1 mL) was heated in a sealed tube at 50° C. for 20 h. The reaction mixture was concentrated in vacuo and following MDAP purification afforded the title compound as a white solid (64 mg).

LC-MS (Method 3): Rt=3.50 min, m/z=564.2 [M]⁺

1H NMR (400 MHz, DMSO) δ 11.53 (1H, bs), 9.11 (1H, s), 8.38 (1.9H, s, formate), 8.14 (1H, bs), 7.93 (2H, m), 7.83 (1H, t, J=7.8 Hz), 7.78 (1H, m), 7.76 (1H, dd, J=8.1, 1.6 Hz), 7.74 (1H, m), 7.70 (1H, d, J=8.3 Hz), 7.67 (1H, d, J=1.2 Hz), 6.31 (1H, s), 4.76 (2H, m), 3.88 (3H, s, obscured), 3.81-3.71 (1H, m, obscured), 3.50 (3H, s), 3.46 (1H, m) 2.16 (3H, s).

The following examples were prepared from Intermediate 16 and the appropriately substituted basic heterocycles using an analogous method to that used in Example 3 (basic heterocycles were known or commercially available). Following purification by MDAP and lyophilisation, the title compounds were obtained as white electrostatic solids:

| Ex | Structure | Name | LC-MS (Method 3) | NMR |
|---|---|---|---|---|
| 4 | 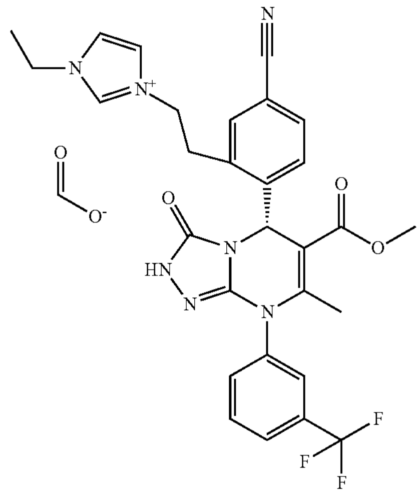 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-ethyl-3H-imidazol-1-ium formate | Rt = 3.59 min, m/z = 578.3 [M]$^+$ | $^1$H NMR (400 MHz, DMSO) δ 11.57 (1H, bs), 9.14 (1H, s), 8.44 (1.5H, bs, formate), 8.14 (1H, bs), 7.97-7.87 (2H, m), 7.86-7.82 (2H, m), 7.82-7.78 (1H, m), 7.78-7.68 (2H, m), 7.57 (1H, s), 6.32 (1H, s), 4.78 (2H, t, J = 8 Hz), 4.22 (2H, q, J = 7 Hz), 3.84-3.72 (2H, m), 3.51 (3H, s), 2.15 (3H, s), 1.43 (3H, t, J = 7 Hz). |
| 5 | 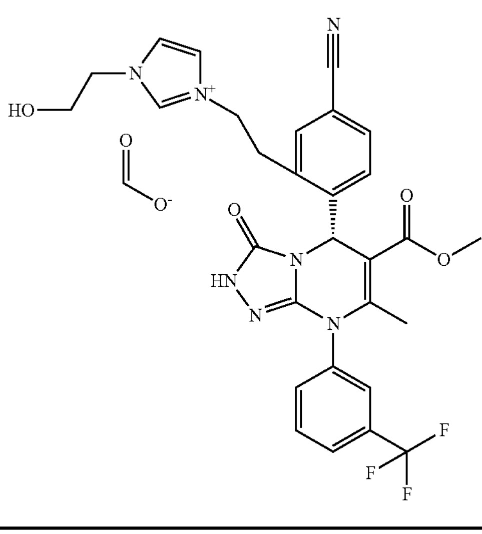 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-(2-hydroxy-ethyl)-3H-imidazol-1-ium formate | Rt = 3.45 min, m/z = 594.3 [M]$^+$ | $^1$H NMR (400 MHz, DMSO) δ 11.55 (1H, bs), 9.19 (1H, s), 8.50 (1.2H, bs, formate), 8.14 (1H, bs), 7.95-7.88 (2H, m), 7.86-7.82 (1H, m), 7.82-7.77 (2H, m), 7.77-7.73 (1H, m), 7.73-7.68 (1H, m), 7.67-7.64 (1H, m), 6.34 (1H, s), 4.87-4.70 (2H, m), 4.29-4.22 (2H, m), 3.83-3.71 (3H, m), 3.51 (3H, s), 3.53-3.38 (2H, m, obscured), 2.15 (3H, s). |

Example 6

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-pyridin-2-ylmethyl-ammonium formate

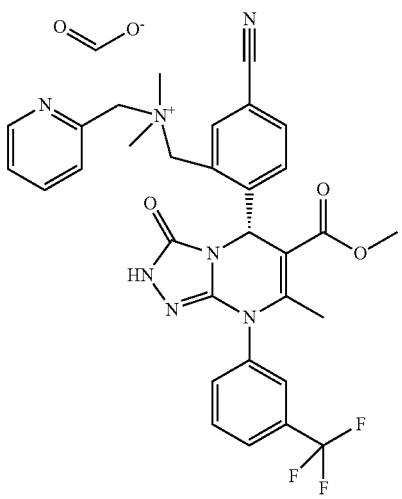

A stirred 2 M solution of dimethylamine in THF (3 mL) was treated with Intermediate 11 (600 mg, 1.10 mmol) and the RXN allowed to stir at RT for 2 h. The reaction mixture was concentrated in vacuo and the resultant residue was purified by chromatography, eluting from 0-6% (2M NH₃ in MeOH) in DCM and gave the title compound as a white foam (408 mg).

LC-MS (Method 2): Rt=2.77 min, m/z=513.2 [M+1]$^+$

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-pyridin-2-ylmethyl-ammonium formate (Example 6)

A solution of Intermediate 17 (150 mg, 0.29 mmol), 2-(bromomethyl)pyridine hydrobromide (178 mg, 0.7 mmol) and DIPEA (106 mg, 140 μL, 0.82 mmol) were dissolved in MeCN (2 mL) in a sealed tube and heated to 50° C. for 72 h. The reaction was cooled, concentrated in vacuo and purified by reverse phase HPLC using a gradient of 5-95% (+0.1% formic acid) MeCN in water to yield the title compound as a white electrostatic solid (60 mg).

LC-MS (Method 3): Rt=3.68 min, m/z 604.1 [M]$^+$ $^1$H NMR (400 MHz, DMSO) δ 11.55 (1H, br s), 8.78-8.74 (1H, m), 8.49 (1H, s), 8.24 (1H, d, J 1.7 Hz), 8.11 (1H, br s), 8.05-7.98 (2H, m), 7.95-7.79 (4H, m), 7.75-7.71 (1H, d), 7.61-7.55 (1H, m), 6.56 (1H, s), 5.24 (2H, s), 4.90 (2H, s), 3.51 (3H, s), 3.22 (6H, d, J 4.4 Hz), 2.07 (3H, s).

Intermediate 17

(R)-5-(4-Cyano-2-dimethylaminomethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

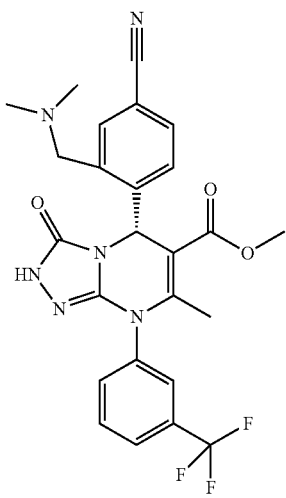

Example 7

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-pyridin-2-ylmethyl-ammonium bromide

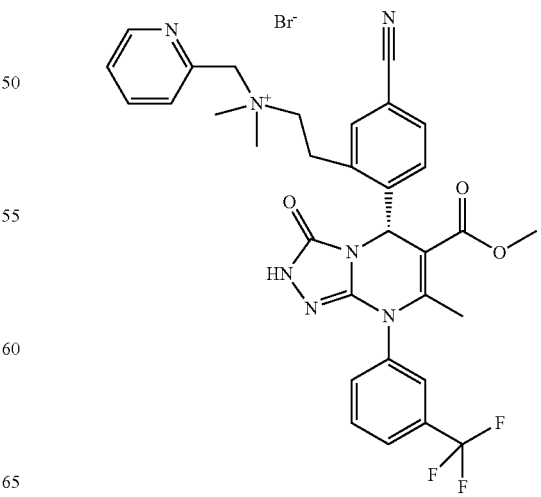

Intermediate 18

(R)-5-[4-Cyano-2-(2-dimethylamino-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

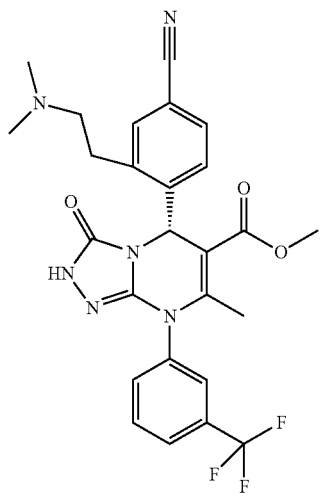

A stirred 2 M solution of dimethylamine in THF (40 mL) was treated with a solution in THF (10 mL) of Intermediate 16 (7.5 g, 13.35 mmol) and the RXN allowed to stir at RT for 2 h. The reaction mixture was concentrated in vacuo and then partitioned between EtOAc (30 mL)/water (30 mL) and the aqueous layer was back-extracted with EtOAc (30 mL) and the combined organic extracts dried (MgSO$_4$), filtered and concentrated in vacuo. The resultant residue was purified by chromatography, eluting from 0-8% (2M NH$_3$ in MeOH) in DCM and gave the title compound as a white foam (5.50 g).

LC-MS (Method 3): Rt=3.37 min, m/z=527.2 [M+1]$^+$ (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-pyridin-2-ylmethyl-ammonium bromide (Example 7)

A mixture of Intermediate 18 (30 mg, 53 μmmol) and 2-bromomethyl-pyridine (11.5 mg, 66 μmol) in MeCN (1 mL) was warmed to 50° C. in a sealed tube for 18 h then concentrated in vacuo. The crude product was partitioned between water and EtOAc and the aqueous layer separated and freeze dried to give the title compound as a white electrostatic solid (10 mg).

$^1$H NMR (400 MHz, DMSO) 11.40 (1H, s), 8.72 (1H, dd), 8.54 (1H, s), 8.13 (1H, s), 8.02-7.91 (3H, m), 7.87-7.80 (2H, m), 7.78-7.69 (3H, m), 7.58-7.54 (1H, m), 6.36 (1H, s), 4.76 (2H, d), 4.11-4.02 (1H, m), 3.90-3.81 (1H, m), 3.75-3.53 (2H, m), 3.51 (3H, s), 3.26 (3H, s), 3.24 (3H, s), 2.17 (3H, s);

LC-MS (Method 3): Rt=3.66 min, m/z=618.2 [M]$^+$

Example 8

4-Cyano-1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridinium bromide

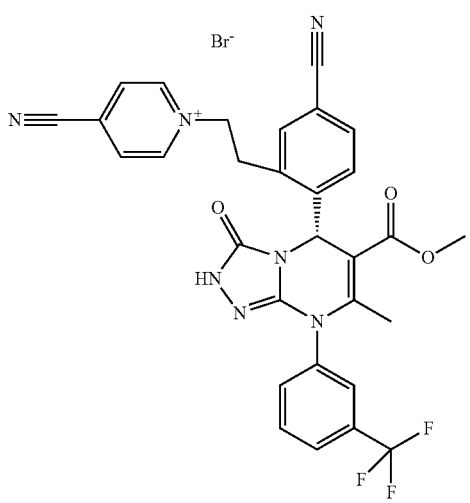

A mixture of Intermediate 16 (30 mg, 53 μmmol) and 4-cyano pyridine (17.5 mg, 160 μmol) in MeCN (1 mL) was warmed to 50° C. in a sealed tube for 18 h then concentrated in vacuo. The crude product was partitioned between water and EtOAc and the aqueous layer separated and freeze dried to give the title compound as a white electrostatic solid (10 mg).

LC-MS (Method 3): Rt=3.63 min, m/z=586.1 [M]$^+$

The following examples can be prepared either from Intermediate 18 and the appropriately substituted halomethyl-heterocycles using an analogous method to that used for Example 7 or from Intermediate 16 and the appropriately substituted nitrogen-containing heterocycles using an analogous method to that used for Example 8. These examples can be isolated following MDAP system or other chromatographic purification methods known by people skilled in the art:

| Ex | Structure | Name | Method | LC-MS (Method 3) | NMR |
|---|---|---|---|---|---|
| 9 | 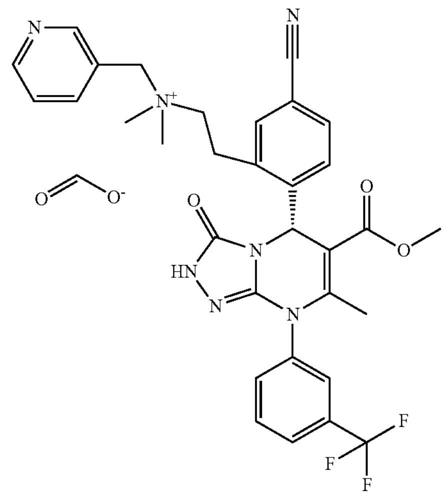 | (2-{5-Cyano-2-[(R)-6-methoxycarbonyl-7-methyl-3-oxo-8-(3-trifluoromethyl-phenyl)-2,3,5,8-tetrahydro[1,2,4]triazolo[4,3a]pyrimidin-5-yl]-phenyl}-ethyl)dimethyl-pyridin-3-ylmethyl-ammonium formate | A | Rt = 3.49 min, m/z = 618.1 [M]+ | ¹H NMR (400 MHz, DMSO) δ 11.47 (1H, br s), 8.84-8.81 (1H, m), 8.74-8.71 (1H, m), 8.52 (1H, s), 8.14 (1H, br s), 8.10-8.06 (1H, m), 7.96-7.88 (2H, m), 7.86-7.81 (2H, m), 7.78-7.75 (1H, m), 7.74-7.69 (1H, m), 7.59-7.54 (1H, m), 6.27 (1H, s), 4.76-4.68 (2H, m), 4.07-4.00 (1H, m), 3.53 (3H, s), 3.51-3.45 (1H, m, obscured), 3.17 (6H, s), 2.20 (3H, s). |
| 10 | 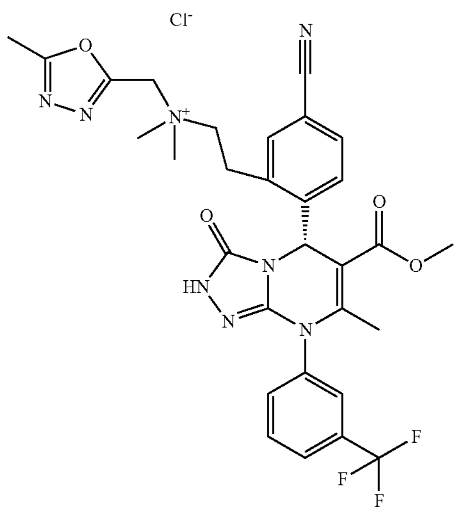 | (2-{5-Cyano-2-[(R)-6-methoxycarbonyl-7-methyl-3-oxo-8-(3-trifluoromethyl-phenyl)-2,3,5,8-tetrahydro[1,2,4]triazolo[4,3a]pyrimidin-5-yl]-phenyl}-ethyl)dimethyl-(5-methyl-[1,3,4]oxadiazol-2-ylmethyl)-ammonium chloride | A | Rt = 3.50 min, m/z = 623.2 [M]+ | |
| 11 | 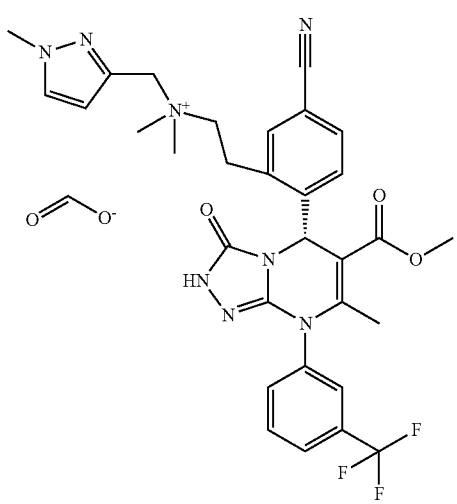 | (2-{5-Cyano-2-[(R)-6-methoxycarbonyl-7-methyl-3-oxo-8-(3-trifluoromethyl-phenyl)-2,3,5,8-tetrahydro[1,2,4]triazolo[4,3a]pyrimidin-5-yl]-phenyl}-ethyl)-dimethyl-(1-methyl-1H-pyrazol-3-ylmethyl)-ammonium chloride | A | Rt = 3.61 min, m/z = 621.2 [M]+ | ¹H NMR (400 MHz, DMSO) δ 11.44 (1H, br s), 8.53 (1H, s), 7.96-7.89 (2H, m), 7.88-7.80 (3H, m), 7.77-7.68 (2H, m), 6.57-6.56 (1H, m), 6.33 (1H, s), 4.65-4.57 (2H, m), 4.00-3.90 (1H, m), 3.88 (3H, s), 3.84-3.75 (1H, m), 3.60-3.48 (2H, m), 3.52 (3H, s), 3.18 (3H, s), 3.17 (3H, s), 2.17 (3H, s). |

-continued

| Ex | Structure | Name | Method | LC-MS (Method 3) | NMR |
|---|---|---|---|---|---|
| 12 | 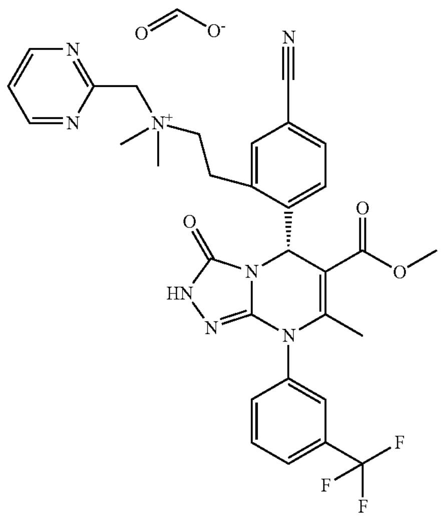 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-pyrimidin-2-ylmethyl-ammonium chloride | A | Rt = 3.56 min, m/z = 619.2 [M]+ | 1H NMR (400 MHz, DMSO) δ 11.45 (1H, br s), 8.99 (1H, s), 8.98 (1H, s), 8.50 (1H, s), 8.15 (1H, br s), 7.96-7.91 (2H, m), 7.86-7.80 (2H, m), 7.77-7.73 (1H, m), 7.70-7.65 (2H, m), 6.30 (1H, s), 4.92-4.84 (2H, m), 4.13-4.04 (1H, m), 3.91-3.82 (1H, m), 3.78-3.69 (1H, m), 3.59-3.51 (1H, m, obscured), 3.52 (3H, s), 3.44-3.28 (6H, s, obscured), 2.17 (3H, s). |
| 13 | 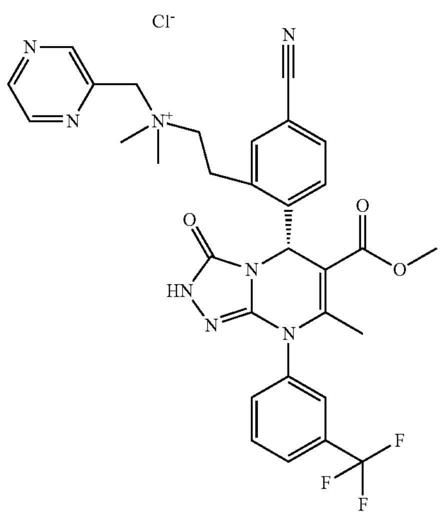 [SMILES: [Cl-] ; COC(=O)C1=C(C)N(c2cccc(C(F)(F)F)c2)c2n[nH]c(=O)n2[C@@H]1c1ccc(C#N)cc1CC[N+](C)(C)Cc1cnccn1] | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-pyrazin-2-ylmethyl-ammonium chloride | A | Rt = 3.55 min, m/z = 619.2 [M]+ | |
| 14 | 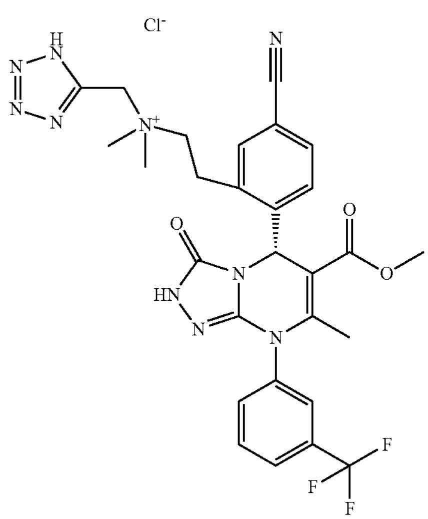 [SMILES: [Cl-] ; COC(=O)C1=C(C)N(c2cccc(C(F)(F)F)c2)c2n[nH]c(=O)n2[C@@H]1c1ccc(C#N)cc1CC[N+](C)(C)Cc1nnn[nH]1] | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-(1H-tetrazol-5-ylmethyl)-ammonium chloride | A | Rt = 3.80 min, m/z = 609.1 [M]+ | |

-continued

| Ex | Structure | Name | Method | LC-MS (Method 3) | NMR |
|---|---|---|---|---|---|
| 15 | 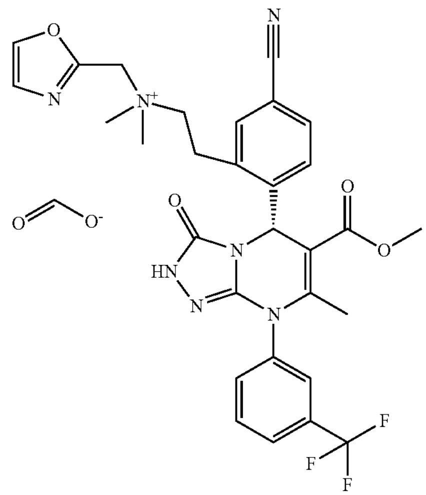 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)dimethyl[1,3,4]oxadiazol-2-ylmethyl-ammonium chloride | A | Rt = 3.56 min, m/z = 608.1 [M]⁺ | $^1$H NMR (400 MHz, DMSO) δ 11.43 (1H, br s), 8.55 (1H, s), 8.38 (1H, d), 8.13 (1H, br s), 7.98-7.89 (2H, m), 7.87-7.79 (2H, m), 7.78-7.73 (1H, m), 7.73-7.66 (1H, m), 7.48 (1H, d), 6.29 (1H, s), 4.98 (2H, s), 4.15-4.01 (1H, m), 3.88-3.66 (2H, m), 3.53 (3H, s), 3.53-3.43 (1H, m), 3.32 (6H, obscured by H₂O), 2.17 (3H, s). |
| 16 | 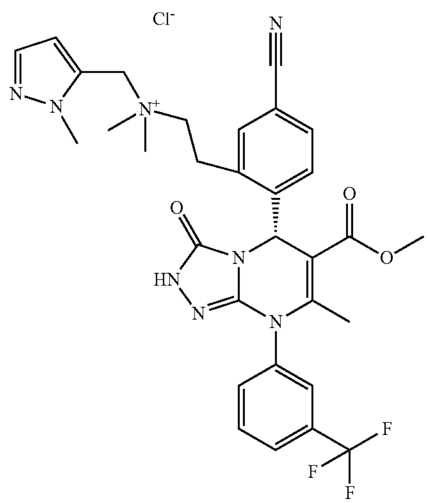 [SMILES: [Cl-] ; COC(=O)C1=C(C)N(c2cccc(C(F)(F)F)c2)c2n[nH]c(=O)n2[C@@H]1c1ccc(C#N)cc1CC[N+](C)(C)Cc1ccnn1C] | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-(2-methyl-2Hpyrazol-3-ylmethyl)-ammonium chloride | A | Rt = 2.99 min, m/z = 621.2 [M]⁺ | |
| 17 | 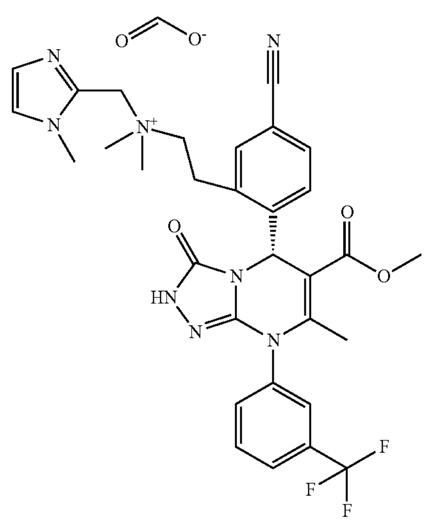 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-(1-methyl-1H-imidazol-2-ylmethyl)-ammonium chloride | A | Rt = 3.50 min, m/z = 621.2 [M]⁺ | $^1$H NMR (400 MHz, DMSO) δ 11.47 (1H, s), 8.52 (1H, s), 8.14 (1H, br s), 7.96-7.68 (6H, m), 7.37 (1H, m), 7.08 (1H, m), 6.45 (1H, s), 4.77 (2H, s), 4.10-4.00 (1H, m), 3.87-3.71 (5H, m), 3.62-3.53 (1H, m), 3.50 (3H, s), 3.22 (3H, s), 3.21 (3H, s), 2.16 (3H, s). |

-continued

| Ex | Structure | Name | Method | LC-MS (Method 3) | NMR |
|---|---|---|---|---|---|
| 18 | 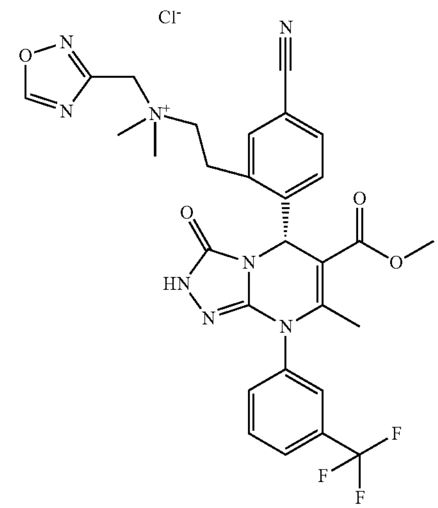 [SMILES: [Cl-] ; COC(=O)C1=C(C)N(c2cccc(C(F)(F)F)c2)c2n[nH]c(=O)n2[C@@H]1c1ccc(C#N)cc1CC[N+](C)(C)Cc1ncon1] | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)dimethyl[1,2,4]oxadiazol-3-ylmethyl-ammonium chloride | A | Rt = 3.57 min, m/z = 609.1 [M]⁺ | |
| 19 | 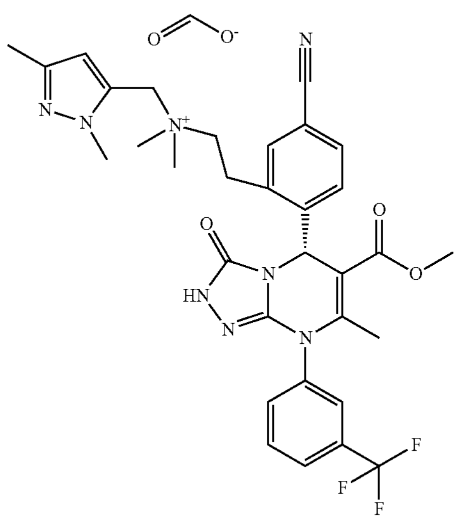 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-(2,5-dimethyl-2H-pyrazol-3-ylmethyl)-dimethyl-ammonium chloride | A | Rt = 3.60 min, m/z = 635.2 [M]⁺ | ¹H NMR (400 MHz, DMSO) δ 11.52 (1H, s), 8.51 (1H, s), 8.13 (1H, br s), 7.96-7.87 (2H, m), 7.87-7.80 (2H, m), 7.79-7.75 (1H, m), 7.74-7.69 (1H, m), 6.47 (1H, s), 6.27 (1H, s), 4.79-4.71 (2H, m), 4.18-4.00 (1H, m), 3.87 (3H, s), 3.83-3.73 (2H, m), 3.52 (3H, s), 3.50-3.48 (1H, m, obscured), 3.17 (3H, s), 3.15 (3H, s), 2.18 (3H, s), 2.16 (3H, s). |
| 20 | 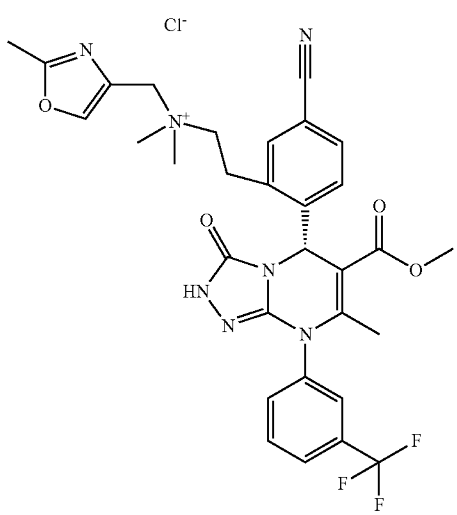 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)dimethyl-(2-methyl-oxazol-4-ylmethyl)-ammonium chloride | A | Rt = 3.67 min, m/z = 622.2 [M]⁺ | |

-continued

| Ex | Structure | Name | Method | LC-MS (Method 3) | NMR |
|---|---|---|---|---|---|
| 21 | 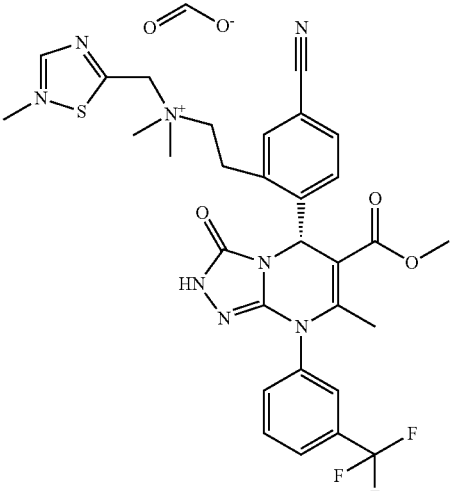 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-(5-methyl[1,3,4]thiadiazol-2-ylmethyl)-ammonium chloride | A | Rt = 3.53 min, m/z = 639.1 [M]$^+$ | $^1$H NMR (400 MHz, DMSO) δ 11.50 (1H, s), 8.53 (1H, s), 8.14 (1H, br s), 7.95-7.89 (2H, m), 7.85-7.80 (2H, m), 7.78-7.74 (1H, m), 7.73-7.69 (1H, m), 6.31 (1H, s), 5.30-5.21 (2H, m), 4.10-4.04 (1H, m), 3.86-3.75 (2H, m), 3.56-3.51 (1H, m, obscured), 3.53 (3H, s), 3.31 (6H, s), 2.81 (3H, s), 2.17 (3H, s). |
| 22 | 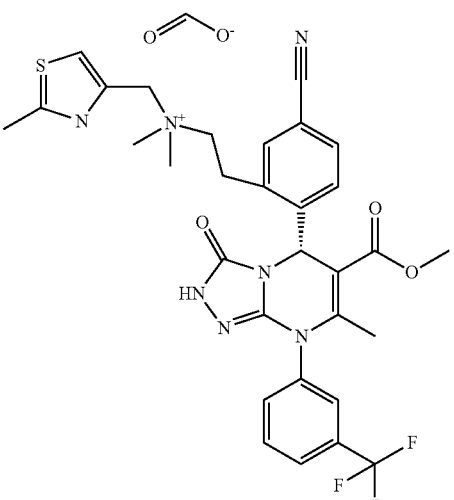 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-(2-methyl-thiazol-5-ylmethyl)-ammonium chloride | A | Rt = 3.73 min, m/z = 638.1 [M]$^+$ | $^1$H NMR (400 MHz, DMSO) δ 11.51 (1H, s), 8.52 (1H, s), 8.13 (1H, br s), 7.96-7.87 (4H, m), 7.86-7.80 (1H, m), 7.78-7.74 (1H, m), 7.73-7.67 (1H, m), 6.33 (1H, s), 4.77-4.70 (2H, m), 4.04-3.96 (1H, m), 3.86-3.78 (1H, m), 3.65-3.54 (2H, m), 3.52 (3H, s), 3.20 (6H, s), 2.70 (3H, s), 2.17 (3H, s). |
| 23 | 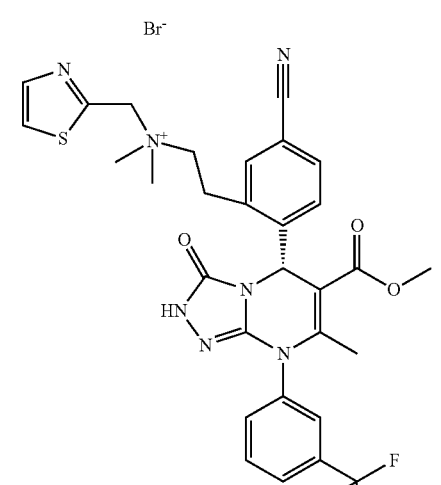 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-thiazol-2-ylmethyl-ammonium bromide | A | Rt = 3.67 min, m/z = 624.1 [M]$^+$ | |

| Ex | Structure | Name | Method | LC-MS (Method 3) | NMR |
|---|---|---|---|---|---|
| 24 | 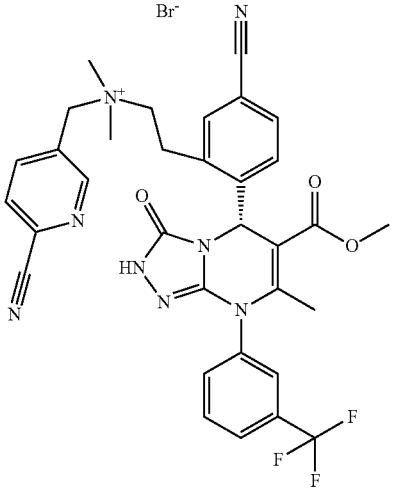 [SMILES: [Br-] ; COC(=O)C1=C(C)N(c2cccc(C(F)(F)F)c2)c2n[nH]c(=O)n2[C@@H]1c1ccc(C#N)cc1CC[N+](C)(C)Cc1ccc(C#N)nc1] | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-(6-cyano-pyridin-3-ylmethyl)-dimethyl-ammonium bromide | A | Rt = 3.71 min, m/z = 643.2 [M]+ | |
| 25 | 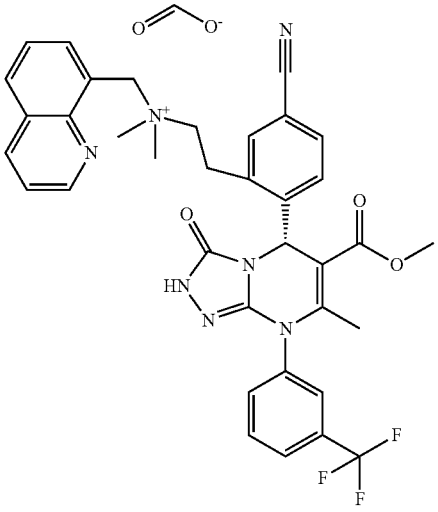 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-quinolin-8-yl methyl-ammonium bromide | A | Rt = 3.91 min, m/z = 668.2 [M]+ | $^1$H NMR (400 MHz, DMSO) 11.46 (1H, s), 9.02 (1H, dd), 8.52-8.48 (2H, m), 8.21 (1H, d), 8.15 (1H, d), 8.11 (1H, br s), 7.93-7.85 (2H, m), 7.83-7.63 (6H, m), 6.24 (1H, s), 5.35-5.23 (2H, m), 4.17-4.06 (1H, m), 3.89-3.83 (2H, m), 3.62-3.52 (1H, m), 3.53-3.46 (1H, m, obscured), 3.49 (3H, s), 3.17 (6H, s), 3.13 (6H, s), 2.13 (3H, s). |
| 26 | 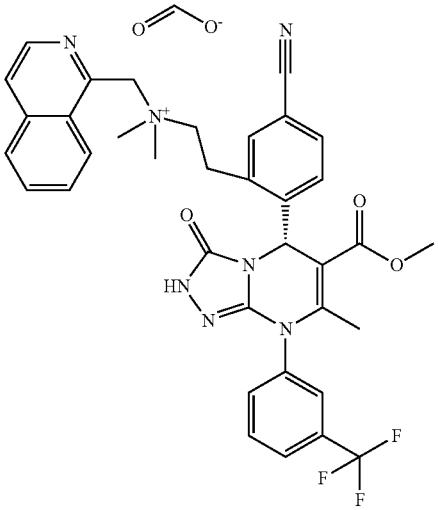 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-isoquinolin-1-ylmethyl-dimethyl-ammonium bromide | A | Rt = 3.90 min, m/z = 668.2 [M]+ | $^1$H NMR (400 MHz, DMSO) 11.40 (1H, br s), 8.69-8.63 (2H, m), 8.54 (1H, s), 8.16 (1H, br s), 8.13 (1H, d), 8.03 (1H, d), 7.97-7.87 (3H, m), 7.85-7.81 (3H, m), 7.77-7.74 (1H, m), 7.69-7.65 (1H, m), 6.08 (1H, s), 5.34 (2H, d), 4.27-4.19 (1H, m), 3.90-3.81 (2H, m), 3.65-3.58 (1H, m), 3.46 (3H, s), 3.41 (3H, s), 3.38 (3H, s), 2.16 (3H, s). |

-continued

| Ex | Structure | Name | Method | LC-MS (Method 3) | NMR |
|---|---|---|---|---|---|
| 27 | 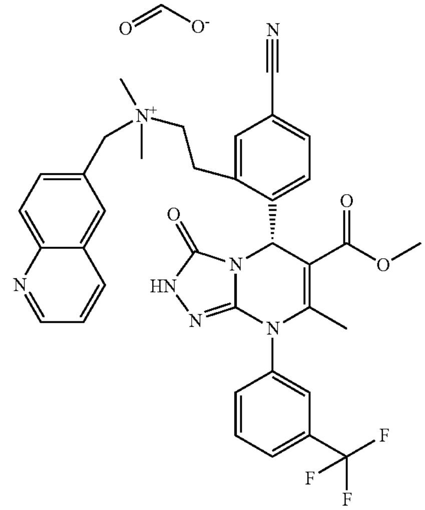 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-quinolin-5-ylmethyl-ammonium bromide | A | Rt = 3.56 min, m/z = 668.2 [M]+ | $^1$H NMR (400 MHz, DMSO) δ 11.53 (1H, br s), 8.99-9.03 (1H, m), 8.52 (1H, s), 8.46 (1H, m), 8.35-8.31 (1H, m), 8.17-8.10 (2H, m), 8.01-7.96 (1H, m), 7.96-7.88 (2H, m), 7.88-7.79 (2H, m), 7.79-7.74 (1H, m), 7.74-7.68 (1H, br d), 7.67-7.60 (1H, m), 6.25 (1H, s), 4.88 (2H, m), 4.19-4.08 (1H, m), 3.89-3.72 (2H, m), 3.49 (3H, s), 3.57-3.45 (1H, partly obscured, m), 3.23 (3H, s), 3.22 (3H, s), 2.16 (3H, s). |
| 28 | 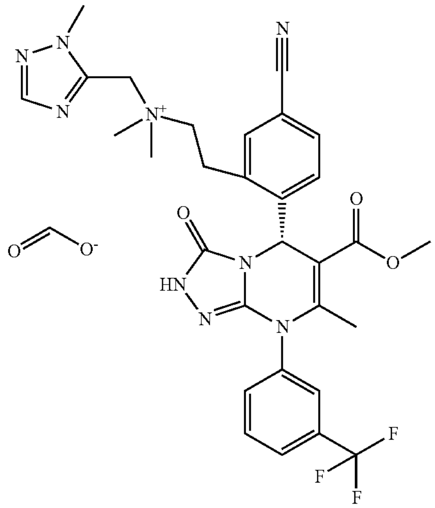 | Formate(2-{5-cyano-2-[(R)-6-methoxy carbonyl-7-methyl-3-oxo-8-(3-trifluoro-methyl-phenyl)-2,3,5,8-tetrahydro-[1,2,4]triazolo[4,3-a]pyrimidin-5-yl]-phenyl}-ethyl)-dimethyl-(2-meth-yl-2H-[1,2,4]triazol-3-ylmethyl)-ammonium; | A | Rt = 3.44 min, m/z = 622.3 [M]+ | $^1$H NMR (400 MHz, DMSO) δ 11.44 (1H, br s), 8.49 (1.3H, s), 8.17 (1H, s), 8.14 (1H, br s), 7.97-7.88 (2H, m), 7.88-7.79 (2H, m), 7.79-7.74 (1H, m), 7.71 (1H, br d), 6.37 (1H, s), 5.02-4.91 (2H, m), 4.15-4.05 (1H, m), 4.03 (3H, s), 3.88-3.75 (2H, m), 3.52 (3H, s), 3.59-3.47 (1H, m, obscured), 3.31 (6H, s), 2.16 (3H, s). |
| 29 | 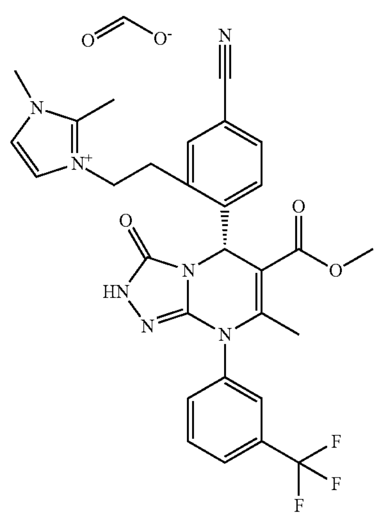 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2,3-dimethyl-3H-imidazol-1-ium bromide | B | Rt = 3.60 min, m/z = 578.1 [M]+ | $^1$H NMR (400 MHz, DMSO) δ 11.46 (1H, br s), 8.52 (1H, s), 8.13 (1H, br s), 7.97-7.87 (2H, m), 7.83 (1H, t), 7.77 (1H, s), 7.76-7.73 (1H, m), 7.73-7.68 (1H, m), 7.65 (2H, s), 6.28 (1H, s), 4.82-4.68 (1H, m), 4.68-4.56 (1H, m), 3.79 (3H, s), 3.71-3.58 (1H, m), 3.49 (3H, s), 2.68 (3H, s), 2.15 (3H, s). |

-continued

| Ex | Structure | Name | Method | LC-MS (Method 3) | NMR |
|----|-----------|------|--------|------------------|-----|
| 30 | 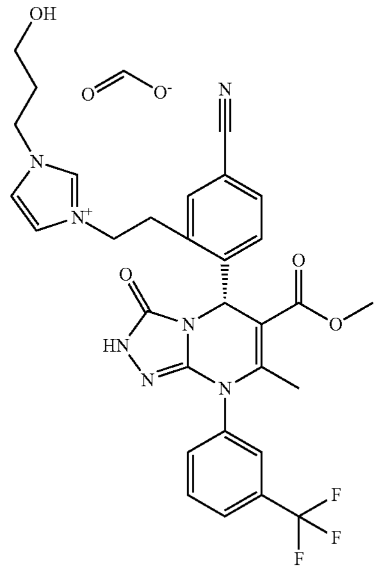 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-(3-hydroxy-propyl)-3H-imidazol-1-ium bromide | B | Rt = 3.49 min, m/z = 608.1 [M]$^+$ | $^1$H NMR (400 MHz, DMSO) δ 11.45 (1H, br s), 9.15 (1H, s), 8.55 (1H, s), 8.13 (1H, br s), 7.97-7.87 (2H, m), 7.86-7.78 (3H, m), 7.77-7.66 (2H, m), 7.57 (1H, s), 6.31 (1H, s), 4.79 (2H, t), 4.26 (2H, t), 3.84-3.73 (1H, m), 3.51 (3H, s), 3.51-3.38 (3H, m), 2.15 (3H, s), 1.98-1.89 (2H, m). |
| 31 | 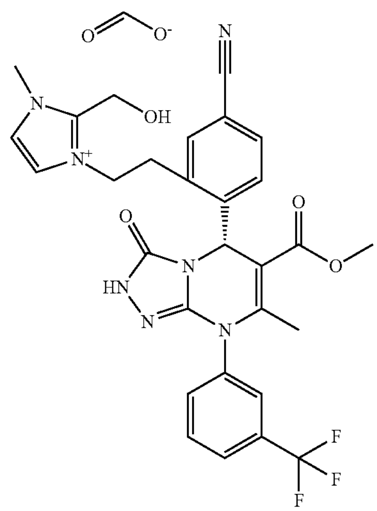 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]phenyl}-ethyl)-2-hydroxymethyl-3-methyl-3H-imidazol-1-ium bromide | B | Rt = 3.53 min, m/z = 594.1 [M]$^+$ | $^1$H NMR (400 MHz, DMSO) δ 11.44 (1H, br s), 8.53 (1H, s), 8.14 (1H, br s), 7.96-7.88 (2H, m), 7.86-7.78 (2H, m), 7.78-7.67 (4H, m), 6.61 (1H, br s), 6.34 (1H, s), 4.97-4.85 (3H, m), 4.74-4.61 (1H, m), 3.91 (3H, s), 3.79-3.67 (1H, m), 3.49 (3H, s), 3.46-3.34 (1H, m), 2.15 (3H, s). |
| 32 | 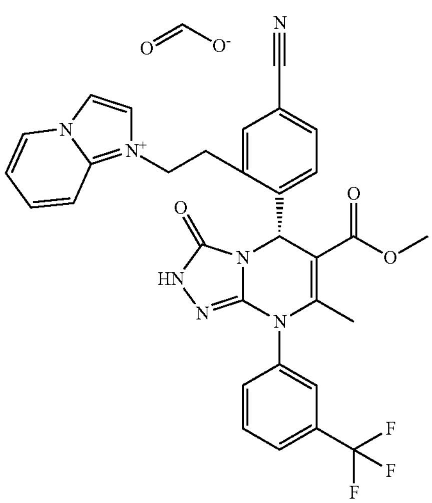 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)imidazo[1,2-a]pyridin-1-ium bromide | B | Rt = 3.64 min, m/z = 600.1 [M]$^+$ | $^1$H NMR (400 MHz, DMSO) δ 11.51 (1H, br s), 8.98 (1H, d, J = 7 Hz), 8.54 (1.2H, s), 8.49-8.44 (1H, m), 8.36-8.27 (2H, m), 8.14 (1H, br s), 8.07-7.98 (1H, m), 7.98-7.87 (2H, m), 7.87-7.79 (1H, m), 7.79-7.67 (3H, m), 7.60-7.54 (1H, m), 6.35 (1H, s), 5.14-5.02 (1H, m), 5.02-4.89 (1H, m), 3.86-3.73 (1H, m), 3.47 (3H, s), 3.51-3.37 (1H, partly obscured, m), 2.15 (3H, s). |

| Ex | Structure | Name | Method | LC-MS (Method 3) | NMR |
|---|---|---|---|---|---|
| 33 | 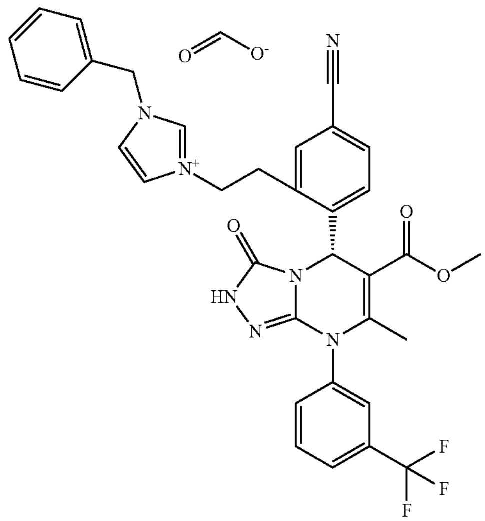 | 3-Benzyl-1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-3H-imidazol-1-ium bromide | B | Rt = 3.89 min, m/z = 640.2 [M]+ | $^1$H NMR (400 MHz, DMSO) δ 11.46 (1H, br s), 9.21 (1H, s), 8.53 (1H, s), 8.14 (1H, br s), 7.96-7.87 (2H, m), 7.86-7.79 (3H, m), 7.77-7.72 (1H, m), 7.72-7.66 (1H, br d), 7.58-7.55 (1H, m), 7.47-7.38 (3H, m), 7.38-7.34 (2H, m), 6.31 (1H, s), 5.45 (2H, s), 4.86-4.75 (2H, m), 3.85-3.74 (1H, m), 3.50 (3H, s), 3.54-3.42 (1H, m), 2.14 (3H, s). |
| 34 | 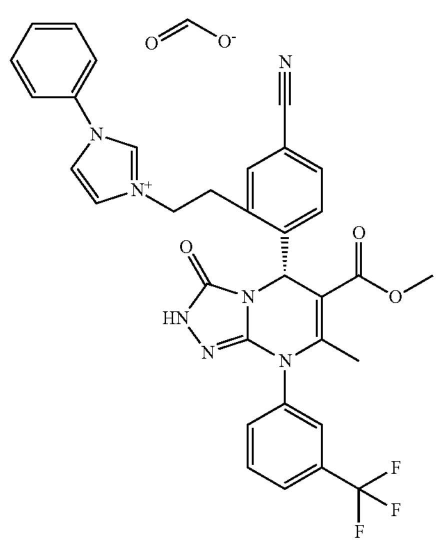 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-phenyl-3H-imidazol-1-ium bromide | B | Rt = 3.82 min, m/z = 626.1 [M]$^+$ | $^1$H NMR (400 MHz, DMSO) δ 11.49 (1H, br s), 9.83 (1H, s), 8.53 (1.1H, s), 8.35-8.32 (1H, m), 8.14 (1H, br s), 8.03-8.00 (1H, m), 7.96-7.88 (2H, m), 7.86-7.66 (8H, m), 7.64-7.58 (1H, m), 6.35 (1H, s), 4.98-4.87 (1H, m), 4.87-4.75 (1H, m), 3.94-3.83 (1H, m), 3.62-3.51 (1H, m), 3.51 (3H, s), 2.16 (3H, s). |

-continued

| Ex | Structure | Name | Method | LC-MS (Method 3) | NMR |
|---|---|---|---|---|---|
| 35 | 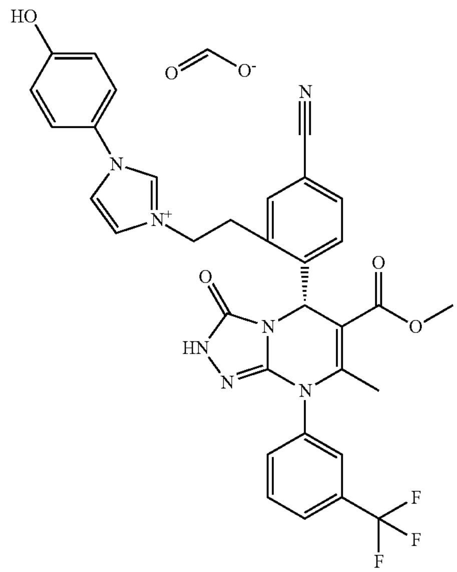 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-3-(4-hydroxy-phenyl)-3H-imidazol-1-ium bromide | B | Rt = 3.71 min, m/z = 642.1 [M]+ | $^1$H NMR (400 MHz, DMSO) δ 9.60 (1H, s), 8.55 (1H, s), 8.18-8.16 (1H, m), 8.14 (1H, br s), 7.97-7.88 (3H, m), 7.85-7.79 (1H, m), 7.78-7.74 (1H, m), 7.74-7.68 (2H, m), 7.55-7.49 (2H, m), 7.00-6.94 (2H, m), 6.34 (1H, s), 4.94-4.72 (2H, m), 3.93-3.81 (1H, m), 3.60-3.49 (1H, m), 3.51 (3H, s), 2.15 (3H, s). |
| 36 | 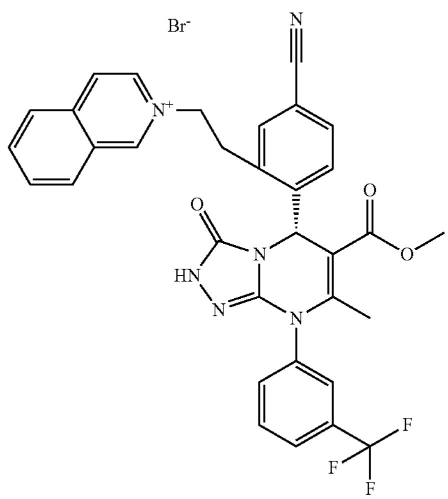 [SMILES: COC(=O)C1=C(C)N(c2cccc(C(F)(F)F)c2)c2n[nH]c(=O)n2[C@@H]1c1ccc(C#N)cc1CC[n+]1ccc2ccccc2c1 ; [Br-]] | 2-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-isoquinolinium bromide | B | Rt = 3.74 min, m/z = 611.1 [M]+ | |
| 37 | 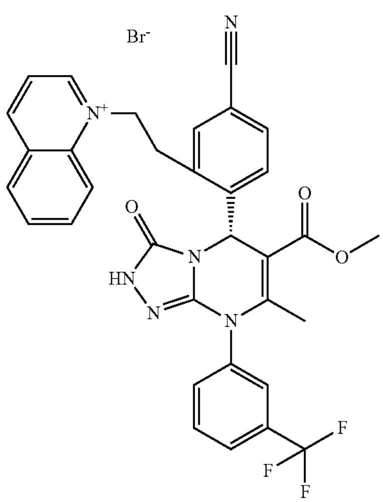 [SMILES: COC(=O)C1=C(C)N(c2cccc(C(F)(F)F)c2)c2n[nH]c(=O)n2[C@@H]1c1ccc(C#N)cc1CC[n+]1cccc2ccccc21 ; [Br-]] | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-quinolinium bromide | B | Rt = 3.76 min, m/z = 611.1 [M]+ | |

Biological Assay.

Compounds of this invention were tested for potency in a human neutrophil elastase (HNE) enzyme activity assay.

HNE Enzyme Assay:

Assays were performed in 96-well plates in a total assay volume of 100 μL. The final concentration of elastase enzyme (human leukocyte elastase, Sigma E8140) was 0.00072 U/mL. The peptide substrate (MeOSuc-Ala-Ala-Pro-Val-AMC, Calbiochem #324740) was used at a final concentration of 100 μM. The final concentration of DMSO was 1% in the assay buffer (0.05M Tris.HCl, 0.1M NaCl, 0.1M $CaCl_2$, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 μg/well. Fluorescence was measured using a Molecular Devices fluorescence plate reader using 380 nm excitation and 460 nm emission wavelengths.

A dose response to each compound was performed and the effect of compound in each experiment was expressed as a percentage inhibition of the control enzyme fluorescence. Dose response curves were plotted and compound potency ($IC_{50}$) was determined. Compounds were tested in at least two separate experiments.

$IC_{50}$s for tested Examples, representative of the invention, are shown in the following table:

| Example | HNE inhibition |
| --- | --- |
| 1-6, 7, 9, 11, 12, 17, 19, 21, 22, 25, 26, 27, 29, 30, 31-35 | ++++ |

In the table above, HNE enzyme inhibition ($IC_{50}$ values) are indicated as follows: >500 nM '+'; 100-500 nM '++'; 20-100 nM '+++'; <20 nM '++++'

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I), or a pharmaceutically acceptable salt thereof:

wherein
A, B and D are independently CH or N;
$R_1$ is:
  hydrogen;
  $(C_1-C_6)$alkyl;
  $NR_7R_8(C_1-C_6)$alkyl-;
  $(C_2-C_4)$alkenyl;
  phenyl$(C_1-C_6)$alkyl, wherein such phenyl ring is optionally substituted by a group $NR_{15}R_{16}(C_1-C_6)$alkyl- or by $N^+R_{15}R_{16}R_{17}(C_1-C_6)$alkyl-;
  —$CH_2(CH_2)OH$;
  —$(CH_2)_nCONR_5R_6$;
  —$(CH_2)_nSO_2NR_5R_6$;
  a group —$CH_2$—$(CH_2)_nNR_5SO_2R_6$;
  —$(CH_2)_r$—$(C_6H_4)$—$SO_2(C_1-C_4)$alkyl;
  —$(CH_2)_tSO_2(C_1-C_4)$alkyl wherein such $(C_1-C_4)$alkyl is optionally substituted by a group —$NR_{15}R_{16}$ or —$N^+R_{15}R_{16}R_{17}$;
  —$SO_2$-phenyl wherein such phenyl ring is optionally substituted by $NR_7R_8(C_1-C_6)$alkyl-; or
  a group —$(CH_2)_n$—W wherein W is a 5-6-membered heteroaryl ring which is optionally substituted by a group —$SO_2(C_1-C_4)$alkyl;
n is 1, 2 or 3;
t is 0, 1, 2 or 3;
r is 0, 1, 2, 3 or 4;
$R_5$ is hydrogen, $(C_1-C_6)$alkyl, $NR_{16}R_{15}(C_1-C_6)$alkyl- or $N^+R_{17}R_{15}R_{16}(C_1-C_6)$alkyl-;
$R_6$ is hydrogen or $(C_1-C_6)$alkyl;
$R_7$ is hydrogen, $(C_1-C_6)$alkyl, $(C_1-C_6)$alkylcarbonyl-, —$SO_2(C_1-C_4)$alkyl, or $NR_{16}R_{15}(C_1-C_6)$alkyl-;
$R_8$ is hydrogen or $(C_1-C_6)$alkyl;
alternatively, $R_7$ and $R_8$ with the nitrogen atom they are linked to can form a $(C_5-C_7)$heterocycloalkyl ring system optionally substituted by one or more $(C_1-C_6)$alkyl or oxo groups;
$R_{16}$ is hydrogen or $(C_1-C_6)$alkyl;
$R_{15}$ is hydrogen or $(C_1-C_6)$alkyl;
$R_{17}$ is hydrogen or $(C_1-C_6)$alkyl;
$R_3$ is a group cyano or a group $C(O)$—$XR_4$;
X is a divalent group selected from the group consisting of —O—, —$(CH_2)$— and —NH—;
$R_4$ is:
  hydrogen;
  $(C_1-C_6)$alkyl;
  a group of formula -[Alk$^1$]-Z wherein Alk$^1$ is a $(C_1-C_4)$alkylene radical and Z is:
    (i) —$NR_9R_{10}$ wherein $R_9$ and $R_{10}$ are independently hydrogen, $(C_1-C_6)$alkyl or $(C_3-C_6)$cycloalkyl, wherein $(C_1-C_6)$alkyl or $(C_3-C_6)$cycloalkyl groups are optionally substituted by one to four groups $R_{35}$ independently selected from the group consisting of $(C_1-C_6)$alkyl, $(C_1-C_6)$alkoxyl, hydroxyl, hydroxyl-$(C_1-C_6)$alkyl, halo, trifluoromethyl, trifluoromethoxy; or, $R_9$ and $R_{10}$ taken together with the nitrogen they are linked to, form a monocyclic $(C_5-C_7)$heterocyclic ring which can contain a further heteroatom selected from the group consisting of N, O, and S and which is optionally substituted by one to four groups $R_{35}$ independently selected from the group consisting of $(C_1-C_6)$alkyl, $(C_1-C_6)$alkoxyl, hydroxyl, hydroxyl-$(C_1-C_6)$alkyl, halo, trifluoromethyl, and trifluoromethoxy; or
    (ii) —$N^+R_{11}R_{12}R_{13}$ wherein $R_{11}$, $R_{12}$ and $R_{13}$ are each independently $(C_1-C_6)$alkyl or $(C_3-C_6)$cycloalkyl, wherein such (C$_1$-C$_6$)alkyl or (C$_3$-C$_6$) cycloalkyl groups are optionally substituted by one to four groups R$_{36}$ independently selected from the group consisting of (C$_1$-C$_6$)alkyl, (C$_1$-C$_6$)alkoxyl, hydroxyl, hydroxyl-(C$_1$-C$_6$)alkyl, halo, trifluoromethyl and trifluoromethoxy; or any two of R$_{11}$, R$_{12}$ and R$_{13}$, taken together with the nitrogen they are linked to, form a monocyclic (C$_5$-C$_7$)heterocyclic ring which can contain a further heteroatom selected from the group consisting of N, O and S and the other of R$_{11}$, R$_{12}$ and R$_{13}$ is a (C$_1$-C$_6$)alkyl or an optionally substituted (C$_3$-C$_6$)cycloalkyl, wherein such monocyclic (C$_5$-C$_7$)heterocyclic, (C$_1$-C$_6$) alkyl or (C$_3$-C$_6$)cycloalkyl groups are optionally substituted by one to four groups R$_{36}$ independently selected from the group consisting of (C$_1$-C$_6$)alkyl, (C$_1$-C$_6$)alkoxyl, hydroxyl, hydroxyl-(C$_1$-C$_6$)alkyl, halo, trifluoromethyl and trifluoromethoxy;

a radical of formula —(CH$_2$)$_q$-[Q]-(CH$_2$)$_p$ Z wherein Z is as above defined, q is 0 or an integer from 1 to 3, p is 0 or an integer from 1 to 3 and Q is a divalent group selected from the group consisting of —O—, phenylene, (C$_5$-C$_7$)heterocycloalkylene, (C$_3$-C$_6$)cycloalkyl and pyridinylene, wherein such phenylene, (C$_5$-C$_7$)heterocycloalkylene, (C$_3$-C$_6$)cycloalkyl and pyridinylene are optionally substituted by one to four groups R$_{37}$ independently selected from the group consisting of (C$_1$-C$_6$)alkyl, (C$_1$-C$_6$)alkoxyl, hydroxyl, hydroxyl-(C$_1$-C$_6$)alkyl, halo, trifluoromethyl and trifluoromethoxy;

R$_2$ is:

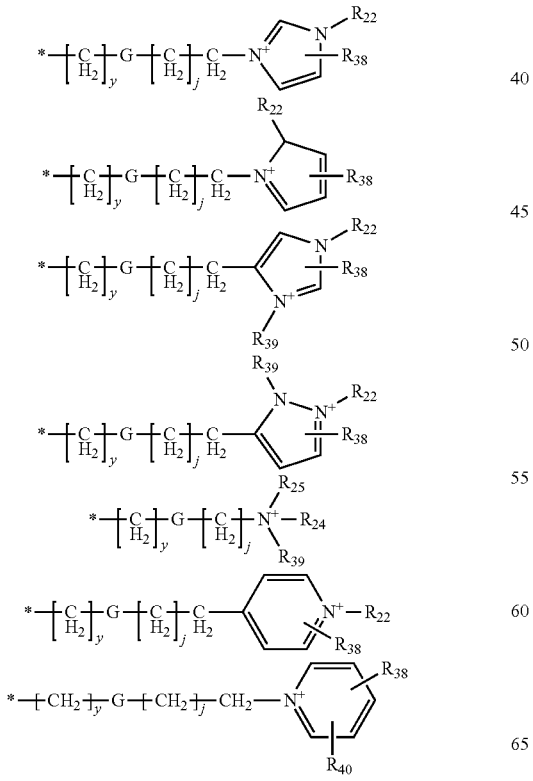

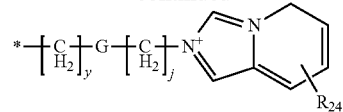

j is 0 or an integer from 1 to 4; y is 0 or an integer from 1 to 4;

G is a divalent linker selected from the group consisting of —O—, —(SO$_2$)—, NR$_{25}$, a bond, C$_2$-C$_6$-alkenylene, C$_2$-C$_6$-alkynylene, (C$_3$-C$_6$)cycloalkylene, mono or bicyclic heterocycloalkylene, —[CONR$_{25}$]— and —[NR$_{25}$CO]—;

R$_{24}$ is hydrogen or (C$_1$-C$_6$)alkyl which is optionally substituted by one or more groups selected from the group consisting of —OR$_{31}$, —SO$_2$R$_{31}$, —CO$_2$R$_{31}$, —CONR$_{31}$R$_{32}$ and —SO$_2$NR$_{31}$R$_{32}$;

R$_{25}$ is hydrogen or (C$_1$-C$_6$)alkyl;

R$_{22}$ is (C$_1$-C$_6$)alkyl, which is optionally substituted by one or more groups selected from the group consisting of (C$_3$-C$_6$)cycloalkyl, phenyl, benzyl, CN, —OR$_{26}$, —SO$_2$R$_{26}$, —CO$_2$R$_{26}$, —CONR$_{26}$R$_{27}$ and —SO$_2$NR$_{26}$R$_{27}$; (C$_3$-C$_{10}$)cycloalkyl, which is optionally substituted by one or more groups selected from the group consisting of —OR$_{26}$, —SO$_2$R$_{26}$, —CO$_2$R$_{26}$, —CONR$_{26}$R$_{27}$ and —SO$_2$NR$_{26}$R$_{27}$; (C$_4$-C$_7$)heterocycloalkyl, which is optionally substituted by one or more groups selected from the group consisting of —OR$_{26}$, —SO$_2$R$_{26}$, —CO$_2$R$_{26}$, —CONR$_{26}$R$_{27}$ and —SO$_2$NR$_{26}$R$_{27}$; aryl, which is optionally substituted with —OH; or heteroaryl, which is optionally substituted with —OH;

R$_{26}$ and R$_{27}$ are independently hydrogen or (C$_1$-C$_6$) alkyl;

alternatively, R$_{22}$ and R$_{38}$ with the nitrogen atom they are linked form a 5-11-membered saturated monocyclic or bicyclic heterocyclic or heteroaromatic ring system which is optionally substituted by one or more groups (C$_1$-C$_6$)alkyl, (C$_1$-C$_6$)alkoxyl, hydroxyl, hydroxyl-(C$_1$-C$_6$)alkyl, —OR$_{28}$, halo, —SO$_2$R$_{33}$, —CO$_2$R$_{33}$, —CONR$_{33}$R$_{34}$, —SO$_2$NR$_{33}$R$_{34}$, nitro, amino, acetamido, trifluoromethyl and trifluoromethoxy;

R$_{28}$, R$_{29}$, R$_{30}$, R$_{31}$, R$_{32}$, R$_{33}$ and R$_{34}$ are each independently hydrogen or (C$_1$-C$_6$)alkyl;

R$_{38}$ is —H or one or two substituents selected from the group consisting of (C$_1$-C$_6$)alkyl, (C$_1$-C$_6$)alkoxyl, hydroxyl, hydroxyl-(C$_1$-C$_6$)alkyl, halo, trifluoromethyl and trifluoromethoxy;

alternatively R$_{38}$ and R$_{40}$, when they are —(C$_1$-C$_6$) alkyl, are linked to form a 6-membered aryl ring;

R$_{39}$ is —(C$_1$-C$_6$)alkyl-heteroaryl, wherein the heteroaryl portion is optionally substituted with one or more substituents selected from the group consisting of —CN, —C(═O), (C$_1$-C$_6$)alkyl, (C$_1$-C$_6$)alkoxyl, hydroxyl, hydroxyl-(C$_1$-C$_6$)alkyl, —OR$_{28}$, halo, —SO$_2$R$_{33}$, —CO$_2$R$_{33}$, —CONR$_{33}$R$_{34}$, —SO$_2$NR$_{33}$R$_{34}$, nitro, amino, acetamido, trifluoromethyl and trifluoromethoxy;

R$_{40}$ is —CN, —(C$_1$-C$_6$)alkyl, —SO$_2$(C$_1$-C$_6$)alkyl or —SO$_2$NR$_{24}$R$_{25}$ wherein only two of A, B and D can be at the same time a nitrogen atom;

wherein if one or more groups $N^+R_{11}R_{12}R_{13}$— or $N^+R_{15}R_{16}R_{17}$— are present, they form quaternary salts with a pharmaceutically acceptable counter ion;

wherein groups $R_5$ to $R_{38}$, and n can have the same or different meanings, if present in more than one group and with the proviso that when $R_{40}$ is —$(C_1$-$C_6)$alkyl, then $R_{38}$ is two substituents which are both —$(C_1$-$C_6)$alkyl.

2. A compound or salt according to claim 1, wherein A is a group CH, B is a group CH and D is a group CH.

3. A compound or salt according to claim 1, wherein $R_2$ is a group —$[CH_2]_y$-G-$[CH_2]_j$—$CH_2$—$N^+R_{24}R_{25}R_{39}$.

4. A compound or salt according to claim 1, wherein $R_2$ is a group

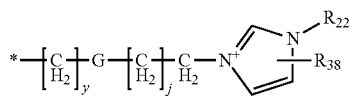

5. A compound or salt according to claim 1, wherein $R_3$ is a group —C(O)—$XR_4$.

6. A compound or salt according to claim 5, wherein X is a divalent group —O— and $R_4$ is $(C_1$-$C_6)$alkyl.

7. A compound or salt according to claim 1, wherein $R_1$ is hydrogen or a group —$(CH_2)_r SO_2(C_1$-$C_4)$alkyl.

8. A compound, which is selected from the group consisting of:

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-methyl-3H-imidazol-1-ium formate;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-ethyl-3H-imidazol-1-ium formate;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-(2-hydroxy-ethyl)-3H-imidazol-1-ium formate;

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-thiazol-4-ylmethyl-ammonium formate;

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(1-methyl-1H-imidazol-4-ylmethyl)-ammonium formate;

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-pyridin-2-ylmethyl-ammonium formate;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-pyridin-2-ylmethyl-ammonium bromide;

4-Cyano-1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridinium bromide;

(2-{5-Cyano-2-[(R)-6-methoxycarbonyl-7-methyl-3-oxo-8-(3-trifluoromethyl-phenyl)-2,3,5,8-tetrahydro[1,2,4]triazolo[4,3a]pyrimidin-5-yl]-phenyl}-ethyl)dimethyl-pyridin-3-ylmethyl-ammonium formate;

(2-{5-Cyano-2-[(R)-6-methoxycarbonyl-7-methyl-3-oxo-8-(3-trifluoromethyl-phenyl)-2,3,5,8-tetrahydro[1,2,4]triazolo[4,3a]pyrimidin-5-yl]-phenyl}-ethyl)dimethyl-(5-methyl-[1,3,4]oxadiazol-2-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro[1,2,4]triazolo[4,3a]pyrimidin-5-yl]-phenyl}-ethyl)-dimethyl-(1-methyl-1H-pyrazol-3-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-pyrimidin-2-ylmethyl-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-pyrazin-2-ylmethyl-ammonium chloride;

(2-{5-Cyano-2-[(R)-6-methoxycarbonyl-7-methyl-3-oxo-8-(3-trifluoromethyl-phenyl)-2,3,5,8-tetrahydro[1,2,4]triazolo[4,3a]pyrimidin-5-yl]-phenyl}-ethyl)-dimethyl-(1H-tetrazol-5-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)dimethyl[1,3,4]oxadiazol-2-ylmethyl-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-(2-methyl-2H pyrazol-3-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-di-methyl-(1-methyl-1H-imidazol-2-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)dimethyl[1,2,4]oxadiazol-3-ylmethyl-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-(2,5-dimethyl-2H-pyrazol-3-ylmethyl)-dimethyl-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)dimethyl-(2-methyl-oxazol-4-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-(5-methyl[1,3,4]thiadiazol-2-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-(2-methyl-thiazol-5-ylmethyl)-ammonium chloride;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-thiazol-2-ylmethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-

[1,2,4]triazolo[4,3a]pyrimidin-5-yl]-phenyl}-ethyl)-(6-cyano-pyridin-3-ylmethyl)-dimethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-quinolin-8-ylmethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-isoquinolin-1-ylmethyl-dimethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-quinolin-5-ylmethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-dimethyl-(2-methyl-2H-[1,2,4]triazol-3-ylmethyl)-ammonium chloride;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2,3-dimethyl-3 H-imidazol-1-ium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-(3-hydroxy-propyl)-3H-imidazol-1-ium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-hydroxymethyl-3-methyl-3H-imidazol-1-ium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl) imidazo[1,2-a]pyridin-1-ium bromide;

3-Benzyl-1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-3H-imidazol-1-ium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-phenyl-3H-imidazol-1-ium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-3-(4-hydroxy-phenyl)-3 H-imidazol-1-ium bromide;

2-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-isoquinolinium bromide; and 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-quinolinium bromide.

9. A compound or salt according to claim 1, which is a compound of formula (I)' where the absolute configuration of carbon (1) is that shown here below

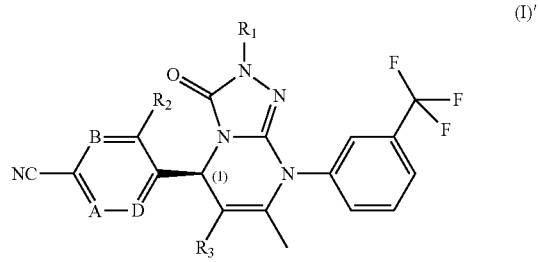

and wherein $R_1$, $R_2$, $R_3$, B and A are as defined for compounds of formula (I).

10. A compound or salt according to claim 1, which is in the form of a pharmaceutically acceptable salt.

11. A pharmaceutical composition, comprising at least one compound or salt according to claim 1 and a pharmaceutically acceptable carrier or excipient.

12. A pharmaceutical composition according to claim 11, which is in a form suitable for oral administration or administration by the pulmonary route.

13. A pharmaceutical composition, comprising at least one compound according to claim 8 and a pharmaceutically acceptable carrier or excipient.

14. A pharmaceutical composition according to claim 13, which is in a form suitable for oral administration or administration by the pulmonary route.

* * * * *

UNITED STATES PATENT AND TRADEMARK OFFICE
CERTIFICATE OF CORRECTION

PATENT NO. : 9,573,955 B2  
APPLICATION NO. : 14/571755  
DATED : February 21, 2017  
INVENTOR(S) : Lilian Alcaraz et al.

It is certified that error appears in the above-identified patent and that said Letters Patent is hereby corrected as shown below:

On the Title Page

Item (73), the Assignee's Information is incorrect. Item (73) should read:  
-- (73) Assignee: Chiesi Farmaceutici S.p.A., Parma (IT) --

Signed and Sealed this  
Seventeenth Day of April, 2018

Andrei Iancu  
*Director of the United States Patent and Trademark Office*